United States Patent
Aharoni et al.

(10) Patent No.: US 11,957,102 B2
(45) Date of Patent: *Apr. 16, 2024

(54) PLANT WITH ALTERED CONTENT OF STEROIDAL ALKALOIDS

(71) Applicant: YEDA RESEARCH AND DEVELOPMENT CO. LTD., Rehovot (IL)

(72) Inventors: Asaph Aharoni, Tel Aviv (IL); Prashant Sonawane, Rehovot (IL); Maxim Itkin, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/859,053

(22) Filed: Jul. 7, 2022

(65) Prior Publication Data
US 2022/0408679 A1  Dec. 29, 2022

Related U.S. Application Data

(60) Division of application No. 17/008,875, filed on Sep. 1, 2020, now Pat. No. 11,412,700, which is a division of application No. 16/123,248, filed on Sep. 6, 2018, now Pat. No. 10,806,119, which is a continuation-in-part of application No. 14/895,059, filed as application No. PCT/IL2014/050497 on Jun. 2, 2014, now Pat. No. 10,100,322.

(60) Provisional application No. 61/831,164, filed on Jun. 5, 2013.

(51) Int. Cl.
  *A01H 6/82* (2018.01)
  *C12N 9/10* (2006.01)
  *C12N 15/82* (2006.01)

(52) U.S. Cl.
  CPC ............ *A01H 6/82* (2018.05); *C12N 9/1059* (2013.01); *C12N 15/8218* (2013.01); *C12N 15/8243* (2013.01); *C12N 15/8247* (2013.01)

(58) Field of Classification Search
  None
  See application file for complete search history.

(56) References Cited

U.S. PATENT DOCUMENTS

| | | | |
|---|---|---|---|
| 4,987,071 A | 1/1991 | Cech et al. | |
| 5,959,180 A | 9/1999 | Moehs et al. | |
| 6,326,174 B1 | 12/2001 | Joyce et al. | |
| 7,375,259 B1 | 5/2008 | Mccue et al. | |
| 7,439,419 B1 | 10/2008 | Mccue et al. | |
| 9,718,850 B2 | 8/2017 | Gin et al. | |
| 9,994,883 B2 | 6/2018 | Goossens et al. | |
| 2005/0108791 A1* | 5/2005 | Edgerton | C12N 15/8247 800/284 |
| 2009/0070895 A1 | 3/2009 | Rae et al. | |
| 2009/0070897 A1 | 3/2009 | Goldman et al. | |
| 2011/0219476 A1 | 9/2011 | Ono et al. | |
| 2011/0265221 A1 | 10/2011 | Abad et al. | |
| 2012/0159676 A1 | 6/2012 | Umemoto et al. | |
| 2013/0167271 A1 | 6/2013 | Umemoto et al. | |

FOREIGN PATENT DOCUMENTS

| | | |
|---|---|---|
| EP | 2982752 | 2/2016 |
| WO | WO 2000/066716 | 11/2000 |
| WO | WO 2011/061656 A1 | 4/2011 |
| WO | WO 2012/095843 A1 | 7/2012 |
| WO | WO 2014/195944 A1 | 12/2014 |

OTHER PUBLICATIONS

Arendt et al. "An endoplasmic reticulum-engineered yeast platform for overproduction of triterpenoids" Metabolic engineering. Mar. 1, 2017;40:165-75.
Arnqvist et al. "Reduction of cholesterol and glycoalkaloid levels in transgenic potato plants by overexpression of a type 1 sterol methyltransferase cDNA" Plant Physiology. Apr. 1, 2003;131(4):1792-9.
Augustin et al. "Molecular activities, biosynthesis and evolution of triterpenold saponins" Phytochemistry. Apr. 1, 2011;72(6):435-57.
Belhaj "Plant genome editing made easy: targeted mutagenesis in model and crop plants using the CRISPR/Cas system. Plant methods" Oct. 11, 2013;9(1):1.
Biazzi et al. "CYP72A67 catalyzes a key oxidative step in Medicago truncatula hemolytic saponin biosynthesis" Molecular plant. Oct. 5, 2015;8(10):1493-506.
Camacho et al. "BLAST+: architecture and applications" BMC bioinformatics. Dec. 2009;10(1):421.
Cárdenas et al. "GAME9 regulates the biosynthesis of steroidal alkaloids and upstream isoprenoids in the plant mevalonate pathway" Nature communications. Feb. 15, 2016;7:10654.
Cárdenas et al. "The bitter side of the nightshades: Genomics drives discovery in Solanaceae steroidal alkaloid metabolism" Phytochemistry. May 1, 2015;113:24-32.
Casamitjana-Martinez et al. "Root-specific CLE19 overexpression and the sol1/2 suppressors implicate a CLV-like pathway in the control of *Arabidopsis* root meristem maintenance" Current Biology. Aug. 19, 2003;13(16):1435-41.
Chen et al. "Short-chain dehydrogenase/reductase catalyzing the final step of noscapine biosynthesis is localized to laticifers in opium poppy" The Plant Journal. Jan. 2014;77(2):173-84.

(Continued)

*Primary Examiner* — Brent T Page
(74) *Attorney, Agent, or Firm* — Mark S. Cohen; PEARL COHEN ZEDEK LATZER BARATZ LLP

(57) ABSTRACT

The present invention relates to key genes in the biosynthesis of steroidal alkaloids and saponins, including regulatory genes and enzyme-encoding genes, and to use thereof for altering the content of steroidal (glyco)alkaloids or phytosterols in plants. The present invention provides genetically modified plants or gene edited plants with altered content of steroidal (glyco)alkaloids, particularly to Solanaceous crop plants with reduced content of antinutritional steroidal glycoalkaloids and to the increase in phytosterols, including cholesterol or cholestanol in these plants. The present invention also provides methods of altering gene expression.

32 Claims, 24 Drawing Sheets

Specification includes a Sequence Listing.

(56) References Cited

OTHER PUBLICATIONS

Cheong et al. "Multicellular survival as a consequence of Parrondo's paradox" Proceedings of the National Academy of Sciences. Jun. 5, 2018;115(23):E5258-9.
Chitwood et al. "A quantitative genetic basis for leaf morphology in a set of precisely defined tomato introgression lines" The Plant Cell. Jul. 1, 2013;25(7):2465-81.
Christen et al. "Structural insights on cholesterol endosynthesis: Binding of squalene and 2, 3-oxidosqualene to supernatant protein factor" Journal of structural biology. Jun. 1, 2015;190(3):261-70.
Database NCBI "Predicted: ethylene-responsive transcription factor 1-like [Solanum lycopersicum]" GeneBank accession No. XP_004229751. URL: http:www.ncbi.nlm.nih.gov/protein/460367786?report=genbank&log$=prottop&blast_rank=2&RID=ZUTPRBJX01R. originally accessed Nov. 23, 2016.
Database NCBI "Predicted: transcription factor BIM2-like [Solanum lycopersicum]" GeneBank accession No. XP_004234703.1. URL: http:www.ncbi.nlm.nih.gov/protein/460377857?report=genbank&log$=prottop&blast_rank=1&RID=TE9A3KF01R. originally accessed Mar. 12, 2013.
Database UniProt [Online], Oct. 1, 2000 (Oct. 1, 2000), "SubName: Full=Putative alcohol dehydrogenase {EC0:0000313:EMBL:CAB91875.I, EC0:0000313:Ensembl Plants:Solyc01g073640.2 1};", XP00' 2779764, retrieved from EBI accession No. UNIPROT:Q9LEG3 Database accession No. Q9LEG3.
Database Protein [Online], Dec. 23, 2015 (Dec. 23, 2015), "Predicted short-chain dehydrogenase reductase 3b-like (xanthoxin dehydrogenase)", XP002779765, retrieved from NCBI Database accession No. XP 015062676.
Database UniProt [Online] Apr. 3, 2013 (Apr. 3, 2013), "SubName: Full=Uncharacterized protein {EC0:0000313:Ensembl Plants:PGSC0003DMT400079897};", XP002779766, retrieved from EBI accession No. UNIPROT:M1D2N5 Database accession No. M1D2N5.
Database NCBI [online], Apr. 15, 2005 (Apr. 15, 2005), Lycopersicon esculentum mRNA for putative alcohol dehydrogenase (yfe37 gene) GenBank:AJ277945.1, https://www.ncbi.nlm.nih.gov/nuccore/7981381.
Database NCBI [online], Nov. 22, 2016 (Nov. 22, 2016), PREDICTED: probable 2-oxoglutarate-dependent dioxygenase AOP1 isoform X1 [Solanum lycopersicum], NCBI Reference Sequence: XP_004233541.1, https://www.ncbi.nlm.nih.gov/protein/460375495?report=genbank.&log$=protalign&blast_rank=1&RID=UWXRDWSA016.
De Carolis et al. "2-Oxoglutarate-dependent dioxygenase and related enzymes: biochemical characterization" Phytochemistry. Aug. 10, 1994;36(5):1093-107.
De Carolis et al. "Isolation and characterization of a 2-oxoglutarate dependent dioxygenase involved in the second-to-last step in vindoline biosynthesis" Plant physiology. Nov. 1, 1990;94(3):1323-9.
Dinesh-Kumar et al. "Virus-induced gene silencing" In Plant Functional Genomics 2003 (pp. 287-293). Humana Press.
Eckert et al. "DNA polymerase fidelity and the polymerase chain reaction" Genome Research. Aug. 1, 1991;1(1):17-24.
Eich, Eckart. "Solanaceae and Convolvulaceae: Secondary metabolites: Biosynthesis, chemotaxonomy, biological and economic significance" (a handbook), pp. 414, 416, 420, 422, 434, 441-445. Springer Science & Business Media, 2008.
Eshed et al. "An introgression line population of Lycopersicon pennellii in the cultivated tomato enables the identification and fine mapping of yield-associated QTL" Genetics. Nov. 1, 1995;141(3):1147-62.
Estornell et al. "A multisite gateway-based toolkit for targeted gene expression and hairpin RNA silencing in tomato fruits" Plant biotechnology journal. Apr. 2009;7(3):298-309.
Expósito-Rodríguez et al. "Selection of internal control genes for quantitative real-time RT-PCR studies during tomato development process" BMC plant biology. Dec. 2008;8(1):131.

Fernandez et al. "Flexible tools for gene expression and silencing in tomato" Plant Physiology. Dec. 1, 2009;151(4):1729-40.
Fernandez-Pozo et al. "The Sol Genomics Network (SGN)—from genotype to phenotype to breeding" Nucleic acids research. Nov. 26, 2014:43(D1):D1036-41.
Finsterbusch et al. "Δ5-3β-Hydroxysteroid dehydrogenase from Digitalis lanata Ehrh.—a multifunctional enzyme in steroid metabolism?" Planta. Oct. 1, 1999;209(4):478-86.
Fire et al. Potent and specific genetic interference by double-stranded RNA in Caenorhabditis elegans. nature. Feb. 1998;391(6669):806.
Friedman et al. "Potato glycoalkaloids: chemistry, analysis, safety, and plant physiology" Critical Reviews in Plant Sciences. Jan. 1, 1997;16(1):55-132.
Friedman M. "Tomato glycoalkaloids: role in the plant and in the diet. Journal of agricultural and food chemistry" Oct. 9, 2002;50(21):5751-80.
Friedman M. "Potato glycoalkaloids and metabolites: roles in the plant and in the diet" Journal of Agricultural and Food Chemistry. Nov. 15, 2006;54(23):8655-81.
Friedman et al. "Dehydrotomatine content in tomatoes" Journal of agricultural and food chemistry. Nov. 16, 1998;46(11):4571-6.
Friedman et al. "Anticarcinogenic effects of glycoalkaloids from potatoes against human cervical, liver, lymphoma, and stomach cancer cells" Journal of agricultural and food chemistry. Jul. 27, 2005;53(15):6162-9.
Friedman M. "Anticarcinogenic, cardioprotective, and other health benefits of tomato compounds lycopene, α-tomatine, and tomatidine in pure form and in fresh and processed tomatoes" Journal of agricultural and food chemistry. Oct. 9, 2013;61(40):9534-50.
Gantasala et al. "Selection and validation of reference genes for quantitative gene expression studies by real-time PCR in eggplant (*Solanum melongena* L)" BMC research notes. Dec. 2013;6(1):312.
Garai S. "Triterpenoid saponins" Nat. Prod. Chem. Res. Sep. 14, 2014;2.
Gatto et al. "Activity of extracts from wild edible herbs against postharvest fungal diseases of fruit and vegetables" Postharvest Biology and Technology. Jul. 1, 2011;61(1):72-82.
Gavidia et al. "Plant progesterone 5β-reductase is not homologous to the animal enzyme. Molecular evolutionary characterization of P5βR from Digitalis purpurea" Phytochemistry. Mar. 1, 2007;68(6):853-64.
Ginzberg et al. "Potato steroidal glycoalkaloids: biosynthesis and genetic manipulation" Potato Research. Feb. 1, 2009;52(1):1-5.
Guo et al. "par-1, a gene required for establishing polarity in C. elegans embryos, encodes a putative Ser/Thr kinase that is asymmetrically distributed" Cell. May 19, 1995;81(4):611-20.
Haralampidis et al. "Biosynthesis of triterpenoid saponins in plants" In History and Trends in Bioprocessing and Biotransformation 2002 (pp. 31-49). Springer, Berlin, Heidelberg.
Hasemann et al. "Structure and function of cytochromes P450: a comparative analysis of three crystal structures" Structure. Jan. 1, 1995;3(1):41-62.
Heim et al. "The basic helix-loop-helix transcription factor family in plants: a genome-wide study of protein structure and functional diversity" Molecular biology and evolution. May 1, 2003;20(5):735-47.
Heinig et al. "Analysis of steroidal alkaloids and saponins in Solanaceae plant extracts using UPLC-qTOF mass spectrometry" In Plant Isoprenoids 2014 (pp. 171-185). Humana Press, New York, NY.
Henry M. "Saponins and phylogeny: example of the "gypsogenin group" saponins" Phytochemistry Reviews. Jul. 1, 2005;4(2-3):89-94.
Herl et al. "Δ5-3β-Hydroxysteroid dehydrogenase (3BHSD) from Digitalis lanata. Heterologous expression and characterisation of the recombinant enzyme" Planta medica. Jun. 2007;73(07):704-10.
Herl et al. "Molecular cloning and heterologous expression of progesterone 5β-reductase from Digitalis lanata Ehrh" Phytochemistry. Feb. 1, 2006;67(3):225-31.
Hérold, M. C., & Henry, M. (2001). UDP-glucuronosyltransferase activity is correlated to saponin production in Gypsophila paniculata root in vitro cultures. Biotechnology letters, 23(5), 335-337.

(56) References Cited

OTHER PUBLICATIONS

Higuchi R. Recombinant PCR. PCR Protocols: A Guide to Methods and Applications. 1990:177-83 (Ch. 22).
Huhman et al. "Metabolic profiling of saponins in Medicago sativa and Medicago truncatula using HPLC coupled to an electrospray ion-trap mass spectrometer" Phytochemistry. Feb. 1, 2002;59(3):347-60.
Ingelbrecht et al. Different 3'end regions strongly influence the level of gene expression in plant cells. The Plant Cell. Jul. 1, 1989;1(7):671-80.
International search Report for PCT Application No. PCT/IL2018/050142 dated Jul. 10, 2018.
International Search Report for PCT Application No. PCT/IL2019/051000 dated Dec. 12, 2019.
Itkin et al. "Biosynthesis of antinutritional alkaloids in solanaceous crops is mediated by clustered genes. Science" Jul. 12, 2013;341(6142):175-9.
Itkin et al. "Glycoalkaloid METABOLISM1 is required for steroidal alkaloid glycosylation and prevention of phytotoxicity in tomato" The Plant Cell. Dec. 1, 2011;23(12):4507-25.
Jarvis et al. "The genome of Chenopodium quinoa" Nature. Feb. 2017;542(7641):307.
Kai et al. Scopoletin is biosynthesized via ortho-hydroxylation of feruloyl CoA by a 2-oxoglutarate-dependent dioxygenase in *Arabidopsis thaliana*. The Plant Journal. Sep. 2008;55(6):989-99.
Kaken "Elucidation of steroid saponin biosynthesis mechanism" Search for research topics, (2016), pp. 1-4, https://kaken.nii.ac.jp/ja/grant/KAKENHI-PROJECT-13J02443 (Search Date: Apr. 8, 2022)—machine translation.
Kallberg et al. "Short-chain dehydrogenases/reductases (SDRs) Coenzyme-based functional assignments in completed genomes" European Journal of Biochemistry. Sep. 2002;269(18):4409-17.
Källberg et al. "Template-based protein structure modeling using the RaptorX web server" Nature protocols. Aug. 2012;7(8):1511.
Karimi M. et. al. "GATEWAY™ vectors for Agrobacterium-mediated plant transformation" Trends Plant Sci. Jul. 2002, 193-195.
Kavanagh et al. "Medium- and short-chain dehydrogenase/reductase gene and protein families" Cellular and Molecular Life Sciences. Dec. 1, 2008;65(24):3895.
Kawai et al. "Evolution and diversity of the 2-oxoglutarate-dependent dioxygenase superfamily in plants" The Plant Journal. Apr. 2014;78(2):328-43.
Kitaoka et al. "Investigating inducible short-chain alcohol dehydrogenases/reductases clarifies rice oryzalexin biosynthesis" The Plant Journal. Oct. 2016;88(2):271-9.
Kundu S. Distribution and prediction of catalytic domains in 2-oxoglutarate dependent dioxygenases. BMC research notes. Dec. 2012;5(1):410.
Kurosawa et al. "UDP-glucuronic acid: soyasapogenol glucuronosyltransferase involved in saponin biosynthesis in germinating soybean seeds" Planta. Aug. 1, 2002;215(4):620-9.
Laurila et al. "Formation of parental-type and novel glycoalkaloids in somatic hybrids between Solanum brevidens and S. tuberosum" Plant Science. Aug. 16, 1996;118(2):145-55.
Li et al. "ESI-QqTOF-MS/MS and APCI-IT-MS/MS analysis of steroid saponins from the rhizomes of Dioscorea panthaica". Journal of Mass Spectrometry. Jan. 1, 2006;41(1):1-22.
Lin et al. "Putative genes involved in salkosaponin biosynthesis in *bupleurum* species" International journal of molecular sciences. Jun. 2013;14(6):12806-26.
Linscott et al. "Mapping a kingdom-specific functional domain of squalene synthase" Biochimica et Biophysica Acta (BBA)—Molecular and Cell Biology of Lipids. Sep. 1, 2016;1861(9):1049-57.
Liu et al. "Eight new triterpenold saponins with antioxidant activity from the roots of Glycyrrhiza uralensis Fisch" Fitoterapia. Mar. 1, 2019;133:186-92.
Louveau et al. "Analysis of Two New Arabinosyltransferases Belonging to the Carbohydrate-Active Enzyme (CAZY) Glycosyl Transferase Family1 Provides Insights into Disease Resistance and Sugar Donor Specificity" The Plant Cell. Dec. 1, 2018;30(12):3038-57.
Marciani DJ. "Is fucose the answer to the immunomodulatory paradox of Quillaja saponins?" International immunopharmacology. Dec. 1, 2015;29(2):908-13.
McCue et al. "Metabolic compensation of steroidal glycoalkaloid biosynthesis in transgenic potato tubers: using reverse genetics to confirm the in vivo enzyme function of a steroidal alkaloid galactosyltransferase" Plant Science. Jan. 1, 2005;168(1):267-73.
McKibbin et al. "Production of high-starch, low-glucose potatoes through over-expression of the metabolic regulator SnRK1" Plant biotechnology journal. Jul. 2006;4(4):409-18.
Meitinger et al. "Purification of $\epsilon$5-3-ketosteroid isomerase from Digitalis lanata" Phytochemistry. Jan. 1, 2015;109:6-13.
Meitinger et al. "The catalytic mechanism of the 3-ketosteroid isomerase of Digitalis lanata involves an intramolecular proton transfer and the activity is not associated with the 3$\neq$-hydroxysteroid dehydrogenase activity" Tetrahedron Letters. Apr. 6, 2016;57(14):1567-71.
Meng et al. "Studies on triterpenoids and flavones in *Glycyrrhiza uralensis* Fisch. by HPLC-ESI-MSn and FT-ICR-MSn" Chinese Journal of Chemistry. Feb. 2009;27(2):299-305.
Mikołajczyk-Bator et al. "Identification of saponins from sugar beet (*Beta vulgaris*) by low and high-resolution HPLC-MS/MS" Journal of Chromatography B. Sep. 1, 2016;1029:36-47.
Milner et al. "Bioactivities of glycoalkaloids and their aglycones from *solanum* species" Journal of Agricultural and Food Chemistry. Mar. 14, 2011;59(8):3454-84.
Mintz-Oron et al. "Gene expression and metabolism in tomato fruit surface tissues" Plant Physiology. Jun. 1, 2008;147(2):823-51.
Moses et al. "Metabolic and functional diversity of saponins, biosynthetic intermediates and semi-synthetic derivatives" Critical reviews in biochemistry and molecular biology. Nov. 1, 2014;49(6):439-62.
Mroczek et al. "Triterpene saponin content in the roots of red beet (*Beta vulgaris* L.) cultivars" Journal of agricultural and food chemistry. Dec. 11, 2012;60(50):12397-402.
Murakami et al. "Medicinal Foodstuffs. XXIII. 1) Structures of New Oleanane-Type Triterpene Oligoglycosides, Basellasaponins A, B, C, and D, from the Fresh Aerial Parts of *Basella rubra* L" Chemical and pharmaceutical bulletin. 2001;49(6):776-9.
Netala et al. "Triterpenoid saponins: a review on biosynthesis, applications and mechanism of their action" Int J Pharm Pharm Sci. 2015;7(1):24-8.
Nomura et al. "Functional specialization of UDP-glycosyltransferase 73P12 in licorice to produce a sweet triterpenoid saponin, glycyrrhizin" The Plant Journal. May 16, 2019.
Ochoa-Villarreal et al. "Plant cell culture strategies for the production of natural products" BMB reports. Mar. 31, 2016;49(3):149.
Ofner et al. "Solanum pennellii backcross inbred lines (BIL s) link small genomic bins with tomato traits" The Plant Journal. Jul. 2016;87(2):151-60.
Oka et al. "Reconstruction of de novo pathway for synthesis of UDP-glucuronic acid and UDP-xylose from intrinsic UDP-glucose in *Saccharomyces cerevisiae*" The FEBS journal. Jun. 2006;273(12):2645-57.
Okamoto et al. "A short-chain dehydrogenase involved in terpene metabolism from Zingiber zerumbet" The FEBS journal. Aug. 2011;278(16):2892-900.
Orzaez e al. "A visual reporter system for virus-induced gene silencing in tomato fruit based on anthocyanin accumulation". Plant physiology. Jul. 1, 2009;150(3):1122-34.
Pollier et al. "Metabolite profiling of triterpene saponins in Medicago truncatula hairy roots by liquid chromatography Fourier transform ion cyclotron resonance mass spectrometry" Journal of natural products. May 26, 2011;74(6):1462-76.
Richmond T. "Higher plant cellulose synthases" Genome biology. Aug. 2000;1(4):reviews3001-1.
Ringer et al. "Monoterpene metabolism. Cloning, expression, and characterization of (−)-isopiperitenol/(−)-carveol dehydrogenase of peppermint and spearmint" Plant physiology. Mar. 1, 2005;137(3):863-72.

(56) References Cited

OTHER PUBLICATIONS

Robinson et al. "Integrative genomics viewer" Nature biotechnology. Jan. 1, 2011;29(1):24-6.
Rocha-Sosa et al. "Both developmental and metabolic signals activate the promoter of a class I patatin gene". The EMBO journal. Jan. 1989;8(1):23.
Roddick JG. "The acetylcholinesterase-inhibitory activity of steroidal glycoalkaloids and their aglycones" Phytochemistry. Jan. 1, 1989;28(10):2631-4.
Roddick JG. "Steroidal glycoalkaloids: nature and consequences of bioactivity" In Saponins used in traditional and modern medicine 1996 (pp. 277-295). Springer, Boston, MA.
Sawai et al. "Triterpenoid biosynthesis and engineering in plants" Frontiers in plant science. Jun. 30, 2011;2:25.
Sayama et al. "The Sg-1 glycosyltransferase locus regulates structural diversity of triterpenold saponins of soybean" The Plant Cell. May 1, 2012;24(5):2123-38.
Schilmiller et al. "Mass spectrometry screening reveals widespread diversity in trichome specialized metabolites of tomato chromosomal substitution lines" The Plant Journal. May 2010;62(3):391-403.
Schwahn et al. "Metabolomics-assisted refinement of the pathways of steroidal glycoalkaloid biosynthesis in the tomato clade" Journal of integrative plant biology. Sep. 2014;56(9):864-75.
Sethaphong et al. "Tertiary model of a plant cellulose synthase" Proceedings of the National Academy of Sciences. Apr. 30, 2013;110(18):7512-7.
Shakya et al. "LC-MS analysis of solanidane glycoalkaloid diversity among tubers of four wild potato species and three cultivars (*Solanum tuberosum*)" Journal of agricultural and food chemistry. Jul. 11, 2008;56(16):6949-58.
Shannon et al. "Cytoscape: a software environment for integrated models of biomolecular interaction networks" Genome research. Nov. 1, 2003;13(11):2498-504.
Sievers et al. "Fast, scalable generation of high-quality protein multiple sequence alignments using Clustal Omega. Molecular systems biology" Jan. 1, 2011;7(1), Article No. 539.
Sonawane et al. "Plant cholesterol biosynthetic pathway overlaps with phytosterol metabolism" Nature plants. Jan. 2017;3(1):16205.
Supplementary European Search Report for European Application No. 14808414.8 dated Oct. 10, 2016.
Tamura et al. "MEGA6: molecular evolutionary genetics analysis version 6.0" Molecular biology and evolution. Oct. 16, 2013;30(12):2725-9.
Thoma et al. "Insight into steroid scaffold formation from the structure of human oxidosqualene cyclase" Nature. Nov. 2004;432(7013):118.
Tiwari et al. "Plant secondary metabolism linked glycosyltransferases: an update on expanding knowledge and scopes" Blotechnology Advances. Sep. 1, 2016;34(5):714-39.
Tonfack et al. "The plant SDR superfamily: involvement in primary and secondary metabolism" Current Topics in Plant Biology. (2011) 12. 41-53.
Trapnell et al. "Differential gene and transcript expression analysis of RNA-seq experiments with TopHat and Cufflinks" Nature protocols. Mar. 2012;7(3):562.
Umemoto et al. "Two cytochrome P450 monooxygenases catalyze early hydroxylation steps in the potato steroid glycoalkaloid biosynthetic pathway" Plant physiology. Aug. 1, 2016:171(4):2458-67.
Unger et al. "Applications of the Restriction Free (RF) cloning procedure for molecular manipulations and protein expression" Journal of structural biology. Oct. 1, 2010;172(1):34-44.
Unger et al. "Recombinant protein expression in the baculovirus-infected insect cell system" In Chemical Genomics and Proteomics 2012 (pp. 187-199). Humana Press.
Vincken et al. "Saponins, classification and occurrence in the plant kingdom" Phytochemistry. Feb. 1, 2007;68(3):275-97.
Vuppaladadiyam et al. "Microalgae cultivation and metabolites production: a comprehensive review" Biofuels, Bioproducts and Biorefining. Mar. 2018;12(2):304-24.
Wang et al. "Identification of isoliquiritigenin as an activator that stimulates the enzymatic production of glycyrrhetinic acid monoglucuronide" Scientific reports. Oct. 2, 2017;7(1):12503.
Wu et al. A new liquid chromatography-mass spectrometry-based strategy to integrate chemistry, morphology, and evolution of eggplant (solanum) species. Journal of Chromatography A. Nov. 1, 2013;1314:154-72.
Wu Ed., 1993 Meth. In Enzymol. vol. 217, San Diego: Academic Press.
Xu et al. "A novel glucuronosyltransferase has an unprecedented ability to catalyse continuous two-step glucuronosylation of glycyrrhetinic acid to yield glycyrrhizin" New Phytologist. Oct. 2016;212(1):123-35.
Yang et al. "Isolation and functional analysis of a strong specific promoter in photosynthetic tissues" Science in China Series C: Life Sciences. Dec. 1, 2003;46(6):651-60.

\* cited by examiner

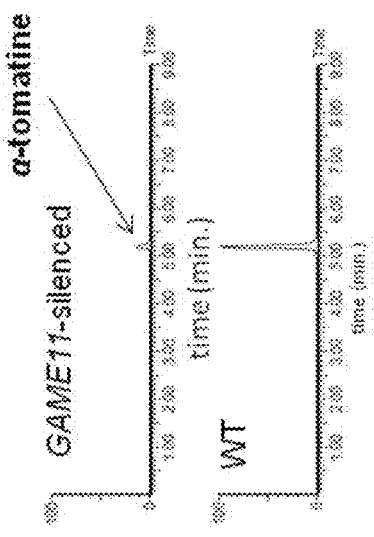
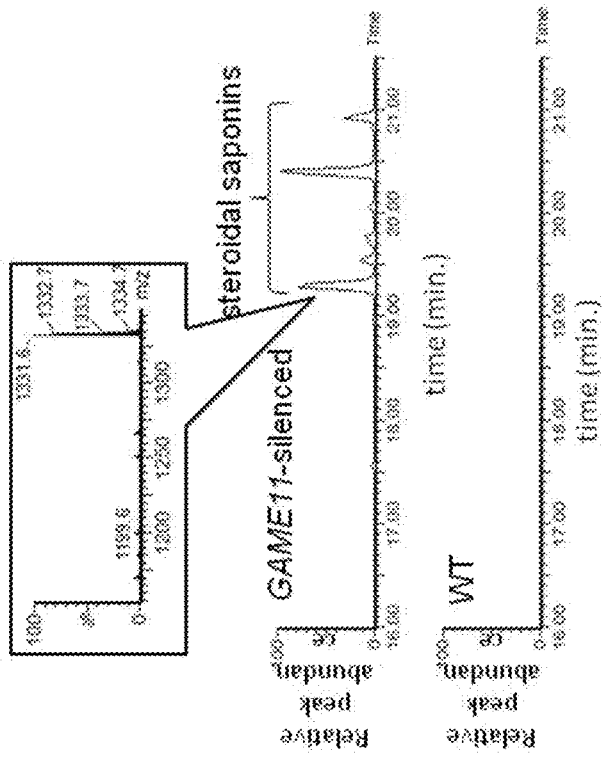
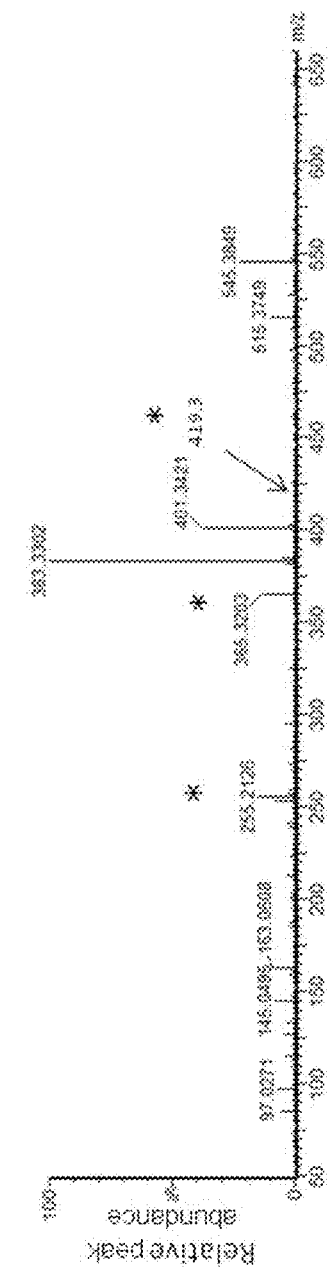
FIGURE 8A
FIGURE 8B
FIGURE 8C

SEQUENCE LISTING

```
Sequence total quantity: 46
SEQ ID NO: 1            moltype = AA  length = 222
FEATURE                 Location/Qualifiers
source                  1..222
                        mol_type = protein
                        organism = Solanum tuberosum
SEQUENCE: 1
MNIAIDDDEI FSLPSLDELE SITHLLYDDD SDFFETLSPM SLDSTTLLPN NPTPNSLESP   60
VRPEGTKETF VAREHEESAP QDWRRFIGVR RRQWGTFSAE IRDPNRRGAR LWLGTYESPQ  120
DAALAYDQAA YKIRGTKARL NFPDLIGSDV PMPPRVTARR RTRSRSRSPE PSTTSSSSSS  180
SSSSSSSSSM ENGTKKRKID LINSIAKAKL LCGVNLQMLI QM                    222

SEQ ID NO: 2            moltype = AA  length = 219
FEATURE                 Location/Qualifiers
source                  1..219
                        mol_type = protein
                        organism = Solanum lycopersicum
SEQUENCE: 2
MSIVIDDDEI FSLPSLDELE SITHLLYDDD SDFFETLSPM SLDVTTLLPN IPTSNSIESP   60
VTPEETKEPS VACEDAPQDW RRFIGVRRRQ WGTFSAEIRD PNRRGARLWL GTYESPRDAA  120
LAYDQAAYKI RGTKVRLNFP DLIGSDVPMP PRVTARRRTR SRSRSPEPLT TSSSSSSSSS  180
SSSSSSSENG TKKRKIDLIN SIAKSKLLCG MDLQMLIQM                        219

SEQ ID NO: 3            moltype = DNA  length = 754
FEATURE                 Location/Qualifiers
source                  1..754
                        mol_type = genomic DNA
                        organism = Solanum tuberosum
SEQUENCE: 3
gaaaatttca ttcatccaaa agaagaatga atattgcaat tgatgatgat gaaatcttct   60
ctttacctag cctcgatgaa cttgaatcta tcacacatct tctttatgat gatgattccg  120
attttttttga aactctttca ccaatgagtt tagatagcac aacattattg cctaataatc  180
ctactccaaa ttcacttgaa tccccccgtaa gaccggaggg aacaaaggaa acatttgtgt  240
cgcgcgaaca cgaagaaagc gcgccacaag attggaggcg gttcatagga gtgaggcgaa  300
ggcagtgggg cacgttttca gccgaaataa gagatccaaa taggagaggc gcgaggctgt  360
ggctaggaac ttatgagtcc ccgcaggatg cagcattggc ttatgaccaa gctgcttaca  420
agattcgggg taccaaagct cggctcaatt ttccggactt aattggctcg gacgtgccta  480
tgccaccaag agtaacggct aggcgtcgta ctcgctcacg ctcgcgctca cccgagccat  540
caacaacttc ttcgtcctca tcctcgtcct cgtcctcatc ctcgtcctcg tccatggaaa  600
atgggacgaa aaaaaggaaa atagatttga taaactcaat agccaaagcc aaattactct  660
gtggtgtgaa tttacaaatg ttgatacaaa tgtgagaaaa gagcaaaggt ttatttttttt  720
cttcgtttaa caattaagta ttacgtataa ttaa                              754

SEQ ID NO: 4            moltype = DNA  length = 754
FEATURE                 Location/Qualifiers
source                  1..754
                        mol_type = genomic DNA
                        organism = Solanum tuberosum
SEQUENCE: 4
gaaaatttca ttcatccaaa agaagaatga atattgcaat tgatgatgat gaaatcttct   60
ctttacctag cctcgatgaa cttgaatcta tcacacatct tctttatgat gatgattccg  120
attttttttga aactctttca ccaatgagtt tagatagcac aacattattg cctaataatc  180
ctactccaaa ttcacttgaa tccccccgtaa gaccggaggg aacaaaggaa acatttgtgt  240
cgcgcgaaca cgaagaaagc gcgccacaag attggaggcg gttcatagga gtgaggcgaa  300
ggcagtgggg cacgttttca gccgaaataa gagatccaaa taggagaggc gcgaggctgt  360
ggctaggaac ttatgagtcc ccgcaggatg cagcattggc ttatgaccaa gctgcttaca  420
agattcgggg taccaaagct cggctcaatt ttccggactt aattggctcg gacgtgccta  480
tgccaccaag agtaacggct aggcgtcgta ctcgctcacg ctcgcgctca cccgagccat  540
caacaacttc ttcgtcctca tcctcgtcct cgtcctcatc ctcgtcctcg tccatggaaa  600
atgggacgaa aaaaaggaaa atagatttga taaactcaat agccaaagcc aaattactct  660
gtggtgtgaa tttacaaatg ttgatacaaa tgtgagaaaa gagcaaaggt ttatttttttt  720
cttcgtttaa caattaagta ttacgtataa ttaa                              754

SEQ ID NO: 5            moltype = DNA  length = 988
FEATURE                 Location/Qualifiers
source                  1..988
                        mol_type = genomic DNA
                        organism = Solanum lycopersicum
```

```
SEQUENCE: 5
taatattaca ttacattcat cacatattat tcatccaaaa caagaatgag tattgtaatt      60
gatgatgatg aaatcttctc tttacctagc cttgatgaac ttgaatccat cacacatctt     120
ctttatgacg acgattccga ttttttcgaa actctttccc caatgagttt agatgttaca     180
acattattgc ctaatattcc tacctccaat tcaattgaat cccccgtaac accgaggaa      240
acaaaagaac catctgtggc gtgtgaggac gcgccacaag attggaggcg gttcataggg     300
gtgaggcgga ggcagtgggg cacgttttca gccgaaataa gagatccaaa taggagagga     360
gcgaggctgt ggctcggaac ttatgagtcc ccgagggatg cagcattagc ttatgaccaa     420
gccgcttaca agattcgggg aaccaaagtt cggcttaatt ttcctgacct gattggctca     480
gacgtaccta tgccacctag agtaacggct aggcgtcgta cacgctcacg ctcacgctca     540
cccgagccat taacaacttc gtcctcgtca tcctcatcat cctcgtcctc gtcctcgtcc     600
tcgtcggaaa atgaacgaa gaaaaggaaa atagatttga taaactcaat agcaaaatcc      660
aaattacttt gtgggatgga tttacaaatg ttaatacaaa tgtaataaaa gagcaaaggt     720
ttattttttct tcgtttgaca attaagtact acgtcgtata attaataagc tcatcaaggt    780
cattgtgtaa atgcacttct ttcacgacct tctcctttat gagattgtta tgaatttttac   840
attatttcct ttatcaacta tatttatc gttttcatac gcggtggagt tcatctgaat       900
ttctcttcct aaggttatat atagagaagg atgttgaatt tttcgtcttc tttttttttat   960
taaataaaaa atctatcttc tacatcag                                         988

SEQ ID NO: 6              moltype = DNA  length = 988
FEATURE                   Location/Qualifiers
source                    1..988
                          mol_type = genomic DNA
                          organism = Solanum lycopersicum
SEQUENCE: 6
taatattaca ttacattcat cacatattat tcatccaaaa caagaatgag tattgtaatt      60
gatgatgatg aaatcttctc tttacctagc cttgatgaac ttgaatccat cacacatctt     120
ctttatgacg acgattccga ttttttcgaa actctttccc caatgagttt agatgttaca     180
acattattgc ctaatattcc tacctccaat tcaattgaat cccccgtaac accgaggaa      240
acaaaagaac catctgtggc gtgtgaggac gcgccacaag attggaggcg gttcataggg     300
gtgaggcgga ggcagtgggg cacgttttca gccgaaataa gagatccaaa taggagagga     360
gcgaggctgt ggctcggaac ttatgagtcc ccgagggatg cagcattagc ttatgaccaa     420
gccgcttaca agattcgggg aaccaaagtt cggcttaatt ttcctgacct gattggctcg     480
gacgtaccta tgccacctag agtaacggct aggcgtcgta cacgctcacg ctcacgctca     540
cccgagccat taacaacttc gtcctcgtca tcctcatcat cctcgtcctc gtcctcgtcc     600
tcgtcggaaa atgaacgaa gaaaaggaaa atagatttga taaactcaat agcaaaatcc      660
aaattacttt gtgggatgga tttacaaatg ttaatacaaa tgtgagaaaa gagcaaaggt     720
ttattttttct tcgtttgaca attaagtact acgtcgtata attaatagac tcatcaaggt    780
cattgtgtaa atgcacttct ttcacgacct tctcctttat gagattgtta tgaatttttac   840
attatttcct ttatcaacta tatttatc gttttcatac gcggtggagt tcatctgaat       900
ttctcttcct aaggttatat atagagaagg atgttgaatt tttcgtcttc tttttttttat   960
taaataaaaa atctatcttc tacatcag                                         988

SEQ ID NO: 7              moltype = AA  length = 341
FEATURE                   Location/Qualifiers
source                    1..341
                          mol_type = protein
                          organism = Solanum tuberosum
SEQUENCE: 7
MADLLSNWSS TLEAVPPSHC IPVHERPSDP VEIVDNIPVI DLGKANGEER SVVVKELLKA      60
FEEYGFFQII NHGVPVDLMD EAMKVYKEFF SLPAAEKAEY AKDAANDTNR GAATLYSSSA     120
KHYDSEEHRY WRDVLEHSCN LDGKDKKTWP SNPPRYREVI GAYGDELRRV SKVILGLLAE     180
GLGLEAGFFD TELGQRMLVN HYPACPDPSL TLGVGGHCDP NLITIIQQEV YGLQILKDDK     240
WIGVQPIRNA FVVNSGLPIT VVSNGKLTSV AHRVVTNTTH SRTSIGTFIC PHDIVEPAKA     300
LVGPENPPQF KSFNWGIDFM PHYLSKKSVY HASLEPFKID A                          341

SEQ ID NO: 8              moltype = AA  length = 342
FEATURE                   Location/Qualifiers
source                    1..342
                          mol_type = protein
                          organism = Solanum lycopersicum
SEQUENCE: 8
MADLLSNWSS TLEAVPKSHC IPEHERPSDP VEIGDSIPVI DLGKANGEER SVVVKDLLKA      60
FEEYGFFQII NHGVPVDLMD EAMKVYKEFF SLPAEEKENY AKDAANNTNR GAATLYSSSA     120
KHYDSEEHRY WRDVLEHSCN LDGEDKKTWP DNPPRYREVI GAYGDELRRV SKVILGMLSE     180
GLGLEAGFFD KELGQRMLVN HYPACPNPSL TLGVGGHCDP NLITIIQQEV YGLQILKDDK     240
WIGVQPIRNA FVVNSGLPIT VYSNGKLTSV AHRVVTNTTE SRTSIGTFIC PHEIVEPAKA     300
LVGPENPPQF KPFHWGIDFM PHYLSKKSVY HASLEPFKTE AN                         342

SEQ ID NO: 9              moltype = DNA  length = 1619
FEATURE                   Location/Qualifiers
source                    1..1619
                          mol_type = genomic DNA
                          organism = Solanum tuberosum
SEQUENCE: 9
ctttgttatg caatttctctt ccctataaat ggcctccat agctcaaatg agatatcaga       60
caatttaaag aagtactatt aacatttaga agatttcttt ctttcccagg taaataaatc     120
atttccctc tttccttctt gctctttctt tgttatttg ttcagatttt taccctttt        180
gttttggtta gattcattga caatggcgga ccttcttcca aactggtcaa gcacattaga     240
```

```
agcagttcct ccaagtcatt gcatcccagt gcatgaaaga ccatcggatc cagttgaaat    300
tgtggacaat attccagtca ttgatttggg aaaagctaat ggtgaagaac gaagtgttgt    360
tgttaaagaa cttttgaaag cttttgaaga atatgggttt tttcaggttt attatttata    420
caatagtaca actctgttct ttttttcttt ttttcttat  tgtatttaaa aatgatctga    480
aattgaaatg atgaaataga taatcaatca tggagtaccc gtagatctaa tggatgaagc    540
aatgaaagtg tacaaagaat ttttcagtct gccagcagca gagaaagcag aatatgcaaa    600
ggatgcagct aatgatacaa ataggggtgc agctacactg tacagtagca gcgctaagca    660
ttatgattca gaggagcatc gttactggag agatgtcttg gaacatagct gcaatcttga    720
tgggaaagac aaaaaaactt ggcctagtaa ccctccaaga tataggtacc tacctaaact    780
atgcttagca aaattccctc ttgttatttt tcttacctag tatttgcttg tccttcaggg    840
aggttattgg tgcatatgga gatgaattga gaagggtgag caaagttatc ttgggtctgt    900
tagctgaagg gctaggtttg gaggcagggt tctttgacac agaacttggg cagagaatgc    960
ttgtgaatca ctatccagca tgcccagatc caagtttaac cttgggagtt ggtggacatt   1020
gtgatcctaa tctcataacc attatccaac aagaagtgta tggtcttcaa atattgaagg   1080
atgacaaatg gattggtgtg cagcctatcc gcaatgcatt tgtggtcaat tctggtttac   1140
caattacggt aggtgtaaca cttctctctta attttcatgg tctacaagcg attctcttat   1200
tgctctgttt tttttgtata aatacaggta gttagcaatg aaagctaac  tagtgttgca   1260
catcgtgtgg tgacaaacac aactcattca cgaacctcca ttggtacttt tatttgccca   1320
cacgatattg ttgagcctgc aaaagcactt gttggtccgg agaatcctcc acagttcaaa   1380
tcctttaatt ggggaattga ttttatgcca cattacctca gcaagaaatc agttaccac    1440
gcatcattgg agcccttcaa aatcgatgct taagcatttg tgtgccagaa ggatcaagtc   1500
tatgctgcta ctttaatttt ccactaaaat aagagcttta atttacaatg tctttctagt   1560
ttgtatccta cctttgttac ctatttcatg aataagaatc tttctttcct attctcttc    1619

SEQ ID NO: 10               moltype = DNA   length = 1292
FEATURE                     Location/Qualifiers
source                      1..1292
                            mol_type = genomic DNA
                            organism = Solanum tuberosum
SEQUENCE: 10
ctttgttatg caattttctt ccctataaat ggccctccat agctcaaatg agatatcaga     60
caatttaaag aagtactatt aacatttaga agatttcttt ctttcccaga ttcattgaca    120
atggcggacc ttcttttcaaa ctggtcaagc acattagaag cagttcctcc aagtcattgc    180
atcccagtgc atgaaagacc atcggatcca gttgaaattg tggacaatat tccagtcatt    240
gatttggaa aagctaatgg tgaagaacga agtgttgttg ttaaagaact tttgaaagct    300
tttgaagaat atgggttttt tcagataatc aatcatggag tacccgtaga tctaatggat    360
gaagcaatga agtgtacaa agaatttttc agtctgccag cagcagagaa agcagaatat    420
gcaaaggatg cagctaatga tacaatagg ggtgcagcta cactgtacag tagcagcgct    480
aagcattatg attcagagga gcatcgttac tggagagatg tcttggaaca tagctgcaat    540
cttgatggga agacaaaaa aacttggcct agtaaccctc caagatatag ggaggttatt    600
ggtgcatatg gagatgaatt gagaagggtg agcaaagtta tcttgggtct gttagctgaa    660
gggctaggtt tggaggcagg gttctttgac acagaacttg gcagagaat gcttgtgaat    720
cactatccag catgcccaga tccaagttta accttggaca ttgtgatcct                780
aatctcataa ccattatcca acaagaagtg tatggtcttc aaatattgaa ggatgacaaa    840
tggattggtg tgcagcctat ccgcaatgca tttgtggtca attctggttt accaattacg    900
gtagttagca atggaaagct aactagtgtt gcacatcgtg tggtgacaaa cacaactcat    960
tcacgaacct ccattggtac ttttatttgc ccacacgata ttgttgagcc tgcaaaagca   1020
cttgttggtc cggagaatcc tccacagttc aaatccttta attggggaat tgattttatg   1080
ccacattacc tcagcaagaa atcagtttac acgcatcat tggagccctt caaaatcgat   1140
gcttaagcat tgtgtgcca gaaggatcaa gtctatgctg ctactttaa tttccactaa    1200
aataagagct ttaattttaca atgtctttct agtttgtatc ctacctttgt tacctatttc   1260
atgaataaga atctttcttt cctattctct tc                                 1292

SEQ ID NO: 11               moltype = DNA   length = 1726
FEATURE                     Location/Qualifiers
source                      1..1726
                            mol_type = genomic DNA
                            organism = Solanum lycopersicum
SEQUENCE: 11
aaaaaatatt tgttttttaaa atgtgtaatt tttagtggca tgctctaaaa aaaaataaaa     60
ttatctgagc atcagttttg gttatgcaat ttccttccct ataaatggcc tccatatct    120
caaatgagat atcaaacaat ttgcagaagt agtagtatta acatttagaa gataactttg    180
tttcccaggt aaataaatca ataaatcctc cttttctttg tttgtttgtt tatttgtga    240
gatatttatg attttttggt ttggtttaga ttgattggca atggcggatc ttctctcgaa    300
ctggtcaagc acattagaag cagttcctaa aagtcattgc atcccagagc atgaaagacc    360
atcagatcca gttgaaattg gcgacagtat tccagtcatt gatttgggaa aagctaatgg    420
tgaagaacga agtgttgttg ttaaagatct gttgaaagct tttgaagaat atgggttttt    480
tcaggtacgc aactctgttt ctttttttt  tgttcccgtt aatgtgaaat tgaaatgcaa    540
atatatgaac aaacagataa tcaatcatgg agtacctgta gatctaatgg atgaagcaat    600
gaaagtgtac aaagaatttt tcagtcttcc agctgaagaa aaagaaatt atgcaaaaga    660
tgcagctaat ataccaata ggggtgcagc tacactgtac agtagcagtg ctaagcatta    720
tgattcagag gagcatcgtt actggagaga tgtgttggaa catagctgca atcttgatgg    780
agaagacaaa aaaacttggc ccgataaccc tccaagatat aggtacctac ctatctaaac    840
tatgtatgct ttagcaatta atttccctct ttgttcttaca atgtattttg gttgtacttc    900
agggaggtta ttggtgccta tggtgatgaa ttgagaaggg tgagcaaagt tatcttgggt    960
atgttaagtg aagggctagg tttggaggca gggttctttg acaaagaact tgggcagaga   1020
atgcttgtga atcactatcc agcatgtcca aatccaagtt taactttggg agttggtgga   1080
cattgtgatc ctaatctcat aaccattatc caacaagaag tctatggtct tcaaatattg   1140
aaggatgaca aatggattgg tgtgcagcct attcgcaatg catttgtggt taattctggt   1200
```

```
ttaccaatta cggtatgtat gtgtgtaggt cttctctaac accccctttt tttcttctct  1260
tataatgttt gctatgcata caggtatata gcaatggaaa gctaactagt gttgcacatc  1320
gtgtggtgac aaacacaact gagtcacgaa cctccattgg tactttttatt tgcccacatg  1380
agattgttga acctgcaaaa gcacttgttg gtcctgagaa tcctcacag ttcaaaccct   1440
tccattgggg aatcgatttt atgccacatt acctcagcag gaaatcagtg taccacgctt  1500
cattggagcc cttcaaaaca gaagctaatt aagcattaag gatatatcaa atctatgctg  1560
ctgctgctac tacttctttt aatttccact gaaataagag ctttaattca aaatgtcttt  1620
ctagtttgta ttctacttac ttcatgaata agaaacttcc aatcctattc tctactggtt  1680
tcgatctaca tgaatatttt attatttcca ttgcattttc aatcag              1726

SEQ ID NO: 12           moltype = DNA   length = 1422
FEATURE                 Location/Qualifiers
source                  1..1422
                        mol_type = genomic DNA
                        organism = Solanum lycopersicum
SEQUENCE: 12
aaaaaatatt tgttttttaaa atgtgtaatt tttagtggca tgctctaaaa aaaaataaaa  60
ttatctgagc atcagtttg gttatgcaat ttccttccct ataaatggcc ctccatatct   120
caaatgagat atcaaacaat ttgcagaagt agtagtatta acatttagaa gataactttg  180
tttcccagat tgattgtcaa tggcggatct tctctcgaac tggtcaagca cattagaagc  240
agttcctaaa agtcattgca tcccagagca tgaaagacca tcagatccag ttgaaattgg  300
cgacagtatt ccagtcattg atttgggaaa agctaatgct gaagaacgaa gtgttgttgt  360
taaagatctg ttgaaagctt tgaagaata tgggtttttt cagataatca atcatggagt   420
acctgtagat ctaatggatg aagcaatgaa agtgtacaaa gaattttca gtcttccagc   480
tgaagaaaaa gaaaattatg caaaagatgc agctaataat accaatagggg gtgcagctac  540
actgtacagt agcagtgcta agcattatga ttcagacgag catcgttact ggagagatgt  600
gttggaacat agctgcaatc ttgatggaga agacaaaaaa acttggcccg ataaccctcc  660
aagatataggg gaggttattg gtgccatgg tgatgaattg agaagggtga gcaaagttat  720
cttgggtatg ttaagtgaag ggctaggttt ggaggcaggg ttcttgaca aagaacttgg   780
gcagagaata cttgtgaatc actatccagc atgtccaaat ccaagtttaa ctttgggagt  840
tggtggacat tgtgatccta atctcataac cattatccaa caagaagtct atggtcttca  900
aatattgaag gatgacaaat ggattggtgt gcagccatt cgcaatgcat ttgtggttaa   960
ttctggttta ccaattacgg tatatagcaa tggaaagcta actagtgttg cacatcgtgt  1020
ggtgacaaac acaactgagt cacgaacctc cattggtact tttatttgcc cacatgagat  1080
tgttgaacct gcaaaagcac ttgttggtcc tgagaatcct ccacagttca aacccttcca  1140
ttggggaatc gattttatgc cacattacct cagcaagaaa tcagtgtacc acgcttcatt  1200
ggagcccttc aaaacagaag ctaattaagc attaaggata tatcaaatct atgctgctgc  1260
tgctactact tcttttaatt tccactgaaa taagagcttt aattcaaaat gtcttctag   1320
tttgtattct acttacttca tgaataagag acttccaatc ctattctcta ctggtttcga  1380
tctacatgaa tattttatta tttccattgc attttcaatc ag                    1422

SEQ ID NO: 13           moltype = AA    length = 224
FEATURE                 Location/Qualifiers
source                  1..224
                        mol_type = protein
                        organism = Solanum lycopersicum
SEQUENCE: 13
MPSLGVFSIL ISRMACYIIV NLSSLIAISR STPGPVEGSV EHSQIIRNGS THEDDIVINP   60
TLLASVQSFV EPNLTAAALY RATHDSHMAA DEAIAFNMPL QPNLFENASV EPSPDAEHPS  120
QTQSLCWPDK RDTIESEVLS YGRNDQEEVK FDGEAVGRSH AYSQRLLNII NQTLASVGVD  180
PSLADVRVQL DISKKTSSGA TTTRLSSGEN YGGAPKRLRT EGSM                   224

SEQ ID NO: 14           moltype = DNA   length = 2497
FEATURE                 Location/Qualifiers
source                  1..2497
                        mol_type = genomic DNA
                        organism = Solanum lycopersicum
SEQUENCE: 14
atgccaagtt tagggggtgtt ttcaatactc atctctagaa tggcttgcta tatcattgtt   60
aatttaagtt ctcttattgc tatttctgct gttgagtaaa aagcatagta gttccttgca  120
tcatttgcac tttcatctgt ttgatgttat gctgtggatt cttttcctaa gtgttgacttt 180
tttctctacc tccctatta ggaaaaagag gcaatagtat tttaagtcca tctcttaagg   240
aatggctaat gttgaaatat aacaaagaac ttccttcttt ggcaacacat ggttggcttc  300
ttgtccttta gctatgtgat tttctgtact tcgattttat tccctcctcc acttccttat  360
tggcagttta gttgtagcat taaaatagat tcattctaac cagatggctt acttatgaa   420
tcttcaactc tttaataata gtaatggaaa attatgaagt cagtgcacca tgagaaagaa  480
gacattgttt gacccaagag aagtaaactg agctatataa aattggattg agcgcttaa   540
ttactgcaga tattaccctc tgaaaagtac tggatcaag aaaaaaatgt tctctgatgt   600
tacctatacc tgtatgcccc agttgctgta cagtaaaggt ataattcagt agtcatttcg  660
tatgcttgcc aaatacagaa aaatgcagac gttagctgta tttctaggg aaactcctcg   720
cctacagttc aaacaaaggt tttacattg cttataattt cctccctcca aagcaaagtg  780
accggatttt gggctctttt aggaggagag ttgggcacaa ctttaggatg gaagcagtaa  840
tgcttttctg gaagtaaaac taatgctctt ctcttattat tgcagagaa gtactcctgg   900
gcccgtgaa ggctctgttg aacattctca aataatcaga aaggctcta ctcatgagga    960
tgatattgtc attaacccaa cattgcttgc aagtgtccag agctttgtag aaccgaactt  1020
gactgctgct gctttatata gagcaacaca cgattctcat atggcagcgg atgaggcaat  1080
tgcctttaac atgccactgc aacctaattt atttgaaaat gcatctgttg aaccatctcc  1140
tgatgctgag caccccttctc agacacaatc attatgttgg ccagataaac gagatacaat  1200
tgagtcggag gttctgagct atggcagaaa tgatcaagaa gaagtgaaat tcgatggtga  1260
```

```
agcagttgga agatcacatg catatagtca aaggtaagat gatttatcag gagttcaata    1320
gctatgactt gatgtccttg taaggtggaa attcaaattt atttcttcta tgacccatg    1380
acttgctaat ttctgtaatg atgccaaact tgtattacac ctacgaagta ggcatgtgat    1440
acagtatcac tttaagtccc ttggaccag tgggcctagt ggcagtcacg gtcttagaag    1500
aattatccta tggttgtcaa gtgcatgaaa tagatttgaa ctagttaatg tttctcgtgg    1560
ttattagctg gttggctaga atgcaaagtg tagcctttt aagcccctc cagcatgagt    1620
tttttttgtaa aacctgctgt aacttgtggg tttgcattt ttttgtgaat aaaattgcca    1680
gttcaacaaa gatttcagtg gcttgaagga agtcatttta tatgacccgg catggtttac    1740
ctgttgaagg ttaataacaa gcggaaccct ggatttcgag atttgagtct cactttagga    1800
tttttcagac ttcccattaa cacaaagtca tgtataacac acatgttcgt atcattctta    1860
cttgtgcagt tgtcctctgt accttaggc acatttaat ctgaactcgg ttgatctgaa    1920
attatattat gatgccagta aactactgat tttggattct atttatgtga catattgggt    1980
cttggtattg agcaggttgc ttaatatcat aaaccagact ctagcatctg tgggagtgga    2040
tccgtcactg gccgatgtta gagtacagct tgatatcagc aaaaaaacaa gcagtggagc    2100
cacaactaca agattaagca gtggagagaa ctatggtggt gctcctaaaa ggcttaggac    2160
agaaggtagt atgtgattat taatctagca tggctccact cctaatttt ctgcatcttg    2220
tcatcgtttt gatggggaga tagttgaagt ggttggtctc cgtggatgag gtggtgcaca    2280
aacagcttat ggttgtccag ttaggttcc atttaaatat gagaagctgc attgtcattc    2340
ttaagggtat ttagtttga attgagataa gtcgactttg atagtctgt cagtgtgata    2400
tggttatgcc tatcgatttg ccatggatct gttttcgtag ttgatattta aacagggaaa    2460
tttgaagttg tttcaaatgt tagcatgaag aatttta                            2497

SEQ ID NO: 15           moltype = DNA   length = 996
FEATURE                 Location/Qualifiers
source                  1..996
                        mol_type = genomic DNA
                        organism = Solanum lycopersicum
SEQUENCE: 15
atgccaagtt tagggtgtt ttcaatactc atctctagaa tggcttgcta tatcattgtt      60
aattttaagtt ctcttattgc tatttctaga agtactcctg ggccgtgga aggctctgtt    120
gaacattctc aaataatcag aaacggctct actcatgagg atgatattgt cattaaccca    180
acattgcttg caagtgtcca gagctttgta gaaccgaact tgactgctgc tgcttttatat    240
agagcaacac acgattctca tatggcagcg gatgaggcaa ttgcctttaa catgccactg    300
caacctaatt tatttgaaaa tgcatctgtt gaacctctc ctgatgctga gcacccttct    360
cagacacaat cattatgttg gccagataaa cgagatacaa ttgagtcgga ggttctgagc    420
tatgcagaaa atgatcaaga agaagtgaaa ttcgatggtg aagcagttgg aagatcacat    480
gcatatagtc aaaggttgct taatatcata aaccagactc tagcatctgt gggagtggat    540
ccgtcactgg ccgatgttag agtacagctt gatatcagca aaaaacaag cagtggagcc    600
acaactacaa gattaagcag tggagagaac tatggtggtg ctcctaaaag gcttaggaca    660
gaaggtagta tgtgattatt aatctagcat ggctccactc ctaatttttc tgcatcttgt    720
catcgttttg atggggagat agttgaagtg gttggtctcc gtggatgagg tggtgcacaa    780
acagcttatg gttgtccagt taggtttcca ttaaatatg agaagctgca ttgtcattct    840
taagggtatt tagttttgaa ttgagataag tcgactttga tagtctgtc agtgtgatat    900
ggttatgcct atcgatttgc catggatctg ttttcgtagt tgatatttaa acagggaaat    960
ttgaagttgt ttcaaatgtt agcatgaaga atttta                              996

SEQ ID NO: 16           moltype = DNA   length = 3899
FEATURE                 Location/Qualifiers
source                  1..3899
                        mol_type = genomic DNA
                        organism = Solanum tuberosum
SEQUENCE: 16
tttttttaca aaaactttt tatccaacac caccgagtag cttgactcgc cccctaaaa       60
aattatttta aaaataaat atttttttt tcttatccca ctcctctccc ctaaaaaaaa     120
aataagttca aaagaattct ttttgggggt gagtgggtga tgaggtggga ggctaggggg    180
ggtactgggt agaggatggg gtgggtgata agaaaaaata aatcttcaaa aagaaaaaaa    240
agttctttta tcttcttaaa ttgctaaatt cttaacattt aattatttaa atgttcttta    300
aaaaaatttc tattacatat atttatgtgt acacaccatt accattttca aaaaaaataa    360
atatttatgt atacacaacg tcaacagaaa attctacata tatgcccatg tggcataaga    420
agggtgtttt taaattcact taatcaagta aaggggtgtt tttaaggctg ttaatagttg    480
gaggattaaa gtaataattc atgccaagtt tagggtgtt ttcaatactt atctctagaa    540
tggtctccct attccttgct atattgtgt taatttaagt tctcttattg ctattctgct    600
atgttgagta aaaagcacag tagttcctg catcatttgc acttctcatc tgtttgatgg    660
tgctgtggg atctttttt caagtggtgt tggacttgt tgcttggatg ataatcttc       720
atgtttactc cttattgttg aactttttt ctacctccct attaaggaaa aaggcaat      780
agtattttca gtccatctct taaggaatgg ctaatgttga agataatg aagaacttcc    840
ttctttggca acacatggtt ggcttcttgt cctctagcta tgtgatattt tatacttcga    900
tttttattcc ctccttcact tcttgttttg cagtttagtt atagcattaa atagattca    960
ttataaccag atgccttact gaaggaatct tctactcttt aataatagta ttaaattagg    1020
tcttaggcct aactcacacc ccaaaagcta gctcaaaggg aggaggattg ttcaagcctt    1080
gtaaggagtc cacccatctc aaagggaga ggctgttca agcctataa ggagtccacc      1140
catctcatta accaccgatg tgggactttt gtcattcttt aacaaatagt attagaaaat    1200
tatgaagtca gtgcaccatg agaaagaaga cattgtttga cccaagagaa gtaaactgag    1260
ctatataaaa tcggattgag actttaattt actgcagata taaccctctg aaaagtactg    1320
gattaagaa aaaaatgttc tctgatgtta ccctacct gtgtgcccca gttactgtac      1380
agtaaagtca taattcagta gttattttgg atgcttccca aatacagaaa atgcagacg    1440
ttagctgttt ttgtagggga aactcctcgc ctatggttca aacaaggct ttacatttgt    1500
ttttaatttt ctccctccaa agcaaagtta ccggatttca ggctgtttta ggaggagagt    1560
tgggcacaac tttaggatgg aagcagtagt gttttttctga agtaaaaact aatgctcttc    1620
```

```
tcttattatt gacagagaag cactcctggg cccgtggaag gctctgttga acattctcaa  1680
ataatcagaa acggctctac tcatgaggat gatattgtca ttaacgcaac attgcttcg   1740
agtgcccaga gctttgtaga accgaacttg actgctgctg ctttatatag agcaacacac  1800
gattctcata tggcagcgga tgaagcaatt gcctttaaca tgccactgca acctaattta  1860
tttgaaaatg catctgttga accatctcct gatgctgagc cccttccca gccacaatca   1920
ttatgttggc caggtaaacg agataccaatt gagtcggagg ttctgagcta tggcagaaat  1980
gatcaggaag aagtgaaatg cgatggtgaa gcagttgcaa gatcacatgc gtatactcaa  2040
aggtaagatg atttatcacg agttcaatag ctatgacttg atgtcctggt aaggtggaaa  2100
ttcaaattta tttcttctac gcccccatga cttgctaatt tctgtaatga tgccaaactt  2160
gtattacacc tacgaaatag gcatgtgata cagaatcact ttaagtacct tggacccagt  2220
gggcctagtg gcagtcaagg tcttagaaga attacctgta gtgttccaat tcttattgt   2280
cctgtgattg ccaagtgcat gaaatagatt cagactaggt aatgtttctc gtggttatta  2340
gctggttggt tgaaatgcag attgtagcct tctgagccc cttccagtat agtttttttt   2400
gtaaaacctg ctgcaacttg tgggtttgca ttttttttgtg aataaaattg ccaattcaaa  2460
aaagatttca gtggcttgaa ggaagtcatt tatatgaccc ggcattgttt acccgagcaa  2520
tcaaatatca atcaggttc cctgcatggc ttcccccaac ttttctacct gacccatcaa  2580
atggaaatct aagttgaagg ttaataacaa gcggatctct ggatttcgag gtttgagtct  2640
cacttaagga tttcccagac ttcccattaa aacgaagaaa tgtataacaa acatgtacat  2700
atcattctga cttgagcagt tgtcctctga acctttaggc acattctgat ctgatttcag  2760
ttgatctgaa attatattat gatgctagta tactactgat tttggattct atttatgta   2820
catattgagt cttggtattg agcaggttgc ttaatatcat aaaccagaca ctagcatctg  2880
tgggagtgga tccttcactg gccgatgtta gagtacagct tgatatcagc aaaaaaccaa  2940
gcagtggagc cacaactaca acattaagca gtgaagagaa ctatgatggt gctcctaaaa  3000
ggcttaggac agaaggtagt atgtgattgt caatctagca tggttccact cctaattttt  3060
ctgcatcttg tcattgtttc gatggggaga tacttgaagt ggttggtctc tgtggatgag  3120
gtggtgcaca acagcttat ggttgtccag ttaggtttcc atttaaatat gagaagctgc  3180
attgtcattc ttaagggtat ttagatagtc gactttgaa attctgtcag tgtgatgtgg  3240
ttatgcctat cgatttgaga tgcctccatg gatctggttt catagttgat atttaaacag  3300
ggaaatttga agttgtttca aatgtcagca tgaagaattt tatgtacatt accaaatctt  3360
ttccttttca gtattttgtg attagttcac ttaaacagga tgctggcttt tcaattgtgt  3420
tttcagaaat aaaagtcagc acttgtatca ttgtgaaaaa ctgaaaattt tggtcttta   3480
gtcgaatcaa caacataatg caagtattta ctgataacgg cgtttggtca gatgaatacg  3540
gcagtttcac aatgattgca tatgaatatg ctcatgttag tccatggtat atattgtaat  3600
tttatcctaa agatatcgta atgagaagtt agatgagttt gatgcgatga actgatgaag  3660
cattggtaat gggttattgg tttagcagtt ttgctaattc tcatttatat ttgggatatc  3720
cgttgtcaaa tgtttgaggt tcttttctta acacattaat cgaattaata aattaaactc  3780
tcggctattc tactaggtgc caatatttgc ttttgagcaa gatgcaatat gtcgttcatt  3840
tggtttgtca ccttgtttct aagtgagttt taatctataa cagaatgttt gttggtaaa   3899

SEQ ID NO: 17           moltype = DNA   length = 990
FEATURE                 Location/Qualifiers
source                  1..990
                        mol_type = genomic DNA
                        organism = Solanum tuberosum
SEQUENCE: 17
atgccaagtt taggggtgtt ttcaatactt atctctagaa tggcttgcta tattgttgtt  60
aatttaagtt ctcttattgc tattagaagc actcctgggc ccgtggaagg ctctgttgaa  120
cattctcaaa taatcagaaa cggctctact catgaggatg atattgtcat taacgcaaca  180
ttgctttcga gtgcccagag ctttgtagaa ccgaacttga ctgctgctgc tttatataga  240
gcaacacacg attctcatat ggcagcggat gaagcaattg cctttaacat gccactgcaa  300
cctaatttat ttgaaaatgc atctgttgaa ccatctcctg atgctgagca cccttcccag  360
ccacaatcat tatgttggcc aggtaaacga gataccaatt agtcggaggt tctgagctat  420
ggcagaaatg atcaggaaga agtgaaatgc gatggtgaag cagttgcaag atcacatgcg  480
tatactcaaa ggtaggttgc ttaatatcat aaaccagaca ctagcatctg tgggagtgga  540
tccttcactg gccgatgtta gagtacagct tgatatcagc aaaaaaccaa gcagtggagc  600
cacaactaca acattaagca gtgaagagaa ctatgatggt gctcctaaaa ggcttaggac  660
agaaggtagt atgtgattgt caatctagca tggttccact cctaattttt ctgcatcttg  720
tcattgtttc gatggggaga tacttgaagt ggttggtctc tgtggatgag gtggtgcaca  780
aacagcttat ggttgtccag ttaggtttcc atttaaatat gagaagctgc attgtcattc  840
ttaagggtat ttagagtcga ctttggaaat tctgtcagtg tgatgtggtt atgcctatcg  900
atttgagatg cctccatgga tctggtttca gttgatatt taaacagggg aaatttgaag  960
ttgtttcaaa tgtcagcatg aagaatttta                                   990

SEQ ID NO: 18           moltype = DNA   length = 220
FEATURE                 Location/Qualifiers
source                  1..220
                        mol_type = other DNA
                        organism = synthetic construct
                        note = syn. polynucl.
SEQUENCE: 18
atgagtattg taattgatga tgatgaaatc ttctctttac ctagccttga tgaacttgaa  60
tccatcacac atcttcttta tgacgacgat tccgattttt cgaaactct ttccccaatg  120
agtttagatg ttacaacatt attgcctaat attcctacct ccaattcaat tgaatccccc  180
gtaacaccgg aggaaacaaa agaaccatct gtggcgtgtg                        220
```

```
SEQ ID NO: 19              moltype = DNA   length = 251
FEATURE                    Location/Qualifiers
source                     1..251
                           mol_type = other DNA
                           organism = synthetic construct
                           note = syn. polynucl.
SEQUENCE: 19
cggatcttct ctcgaactgg tcaagcacat tagaagcagt tcctaaaagt cattgcatcc    60
cagagcatga aagaccatca gatccagttg aaattggcga cagtattcca gtcattgatt   120
tgggaaaagc taatggtgaa gaacgaagtg ttgttgttaa agatctgttg aaagcttttg   180
aagaatatgg gttttttcag ataatcaatc atggagtacc tgtagatcta atggatgaag   240
caatgaaagt g                                                       251

SEQ ID NO: 20              moltype = DNA   length = 35
FEATURE                    Location/Qualifiers
source                     1..35
                           mol_type = other DNA
                           organism = synthetic construct
                           note = syn. polynucl.
SEQUENCE: 20
aaaaagaatt ccggatcttc tctcgaactg gtcaa                              35

SEQ ID NO: 21              moltype = DNA   length = 39
FEATURE                    Location/Qualifiers
source                     1..39
                           mol_type = other DNA
                           organism = synthetic construct
                           note = syn. polynucl.
SEQUENCE: 21
aaaaagaatt ccactttcat tgcttcatcc attagatct                          39

SEQ ID NO: 22              moltype = DNA   length = 37
FEATURE                    Location/Qualifiers
source                     1..37
                           mol_type = other DNA
                           organism = synthetic construct
                           note = syn. polynucl.
SEQUENCE: 22
aaaaagaatt ccttagctta tggccacatc acacctt                            37

SEQ ID NO: 23              moltype = DNA   length = 37
FEATURE                    Location/Qualifiers
source                     1..37
                           mol_type = other DNA
                           organism = synthetic construct
                           note = syn. polynucl.
SEQUENCE: 23
aaaaagaatt cactcaagat ttggtgaagc tgtggtt                            37

SEQ ID NO: 24              moltype = DNA   length = 36
FEATURE                    Location/Qualifiers
source                     1..36
                           mol_type = other DNA
                           organism = synthetic construct
                           note = syn. polynucl.
SEQUENCE: 24
aaaaaggcgc gccaatcata gagaagaaag aagacg                             36

SEQ ID NO: 25              moltype = DNA   length = 38
FEATURE                    Location/Qualifiers
source                     1..38
                           mol_type = other DNA
                           organism = synthetic construct
                           note = syn. polynucl.
SEQUENCE: 25
aaaaagcggc cgcactcctg caggaattgt catttctc                           38

SEQ ID NO: 26              moltype = DNA   length = 43
FEATURE                    Location/Qualifiers
source                     1..43
                           mol_type = other DNA
                           organism = synthetic construct
                           note = syn. polynucl.
SEQUENCE: 26
aaaaagcggc cgcatgagta ttgtaattga tgatgatgaa atc                     43
```

```
SEQ ID NO: 27              moltype = DNA   length = 33
FEATURE                    Location/Qualifiers
source                     1..33
                           mol_type = other DNA
                           organism = synthetic construct
                           note = syn. polynucl.
SEQUENCE: 27
aaaaggcgcg cccacacgcc acagatggtt ctt                                 33

SEQ ID NO: 28              moltype = DNA   length = 59
FEATURE                    Location/Qualifiers
source                     1..59
                           mol_type = other DNA
                           organism = synthetic construct
                           note = syn. polynucl.
SEQUENCE: 28
ggggacaagt ttgtacaaaa aagcaggcta tgagtattgt aattgatgat gatgaaatc     59

SEQ ID NO: 29              moltype = DNA   length = 54
FEATURE                    Location/Qualifiers
source                     1..54
                           mol_type = other DNA
                           organism = synthetic construct
                           note = syn. polynucl.
SEQUENCE: 29
ggggaccact ttgtacaaga aagctgggtt catactacct tctgtcctaa gcct          54

SEQ ID NO: 30              moltype = DNA   length = 55
FEATURE                    Location/Qualifiers
source                     1..55
                           mol_type = other DNA
                           organism = synthetic construct
                           note = syn. polynucl.
SEQUENCE: 30
ggggacaagt ttgtacaaaa aagcaggcta tgaatattgc aattgatgat gatga         55

SEQ ID NO: 31              moltype = DNA   length = 59
FEATURE                    Location/Qualifiers
source                     1..59
                           mol_type = other DNA
                           organism = synthetic construct
                           note = syn. polynucl.
SEQUENCE: 31
ggggaccact ttgtacaaga aagctgggtt catttgtatc aacatttgta aattcacac     59

SEQ ID NO: 32              moltype = DNA   length = 2142
FEATURE                    Location/Qualifiers
source                     1..2142
                           mol_type = genomic DNA
                           organism = Solanum lycopersicum
SEQUENCE: 32
atgaaaaaaa ccatggagct caacaaaagc actgttccac aacctatcac caccgtatac    60
cgactccaca tgttcatcca ctcaataatc atgcttgcat taatatacta ccgtgtatct   120
aatttgttta aattcgaaaa cattctcagt ttacaagcac ttgcttgggc gctcatcact   180
tttggtgaat ttagtttcat tctcaagtgg ttcttcgaca aggtactcg ttggcgcaaa    240
gttgaacgag atgttttccc tgaaaacatt acttgcaaag attccgatct accgccaatt   300
gacgtaatgg tattcactgc caatcctaag aaagagccaa ttgtagatgt catgaacact   360
gtgatatccg caatggctct tgattatccc accgataaat tggctgtgta tctcgctgat   420
gatggaggat gtccattgtc gttgtacgcc atggaacaag cgtgtttgtt tgcaaagcta   480
tggttacctt tctgtagaaa ctatgagaat aaaacgagat gcccaaaagc attttttct    540
ccgttaggag atgatgaccg tgttcttaag aatgatgatt tgctgctga aatgaaagaa    600
attaaattga aatatgaaga gttccagcag aaggtggaac atgctggtga atctggaaaa   660
atcaatggta acgtagtgcc tgatagagct tcgcttatta aggtaataaa cgagagggag   720
aacgaaaaga gtgtggatga tatgacgaaa atgccctgc tagtttatgt atcccgtgaa    780
agaagattca accgtcttca tcatttcaag ggtggatctg caaatgctct acttcgagtt   840
tctggaataa tgagtaatgc cccctatgta ctggtgttag attgtgattt cttctgtcat   900
gatccaatat cagctaggaa ggcaatgtgt tttcatcttg atccaaagct atcatctgat   960
ttagcctatg ttcagttccc tcaagtcttt tacaatgtca gcaagtcaga tatttatgat  1020
gtcaaaatta gacaggctta caagacaata tggcatggaa tggatggtat ccaaggccca  1080
gtgttatctg ggactggtta ttttctcaag aggaaagcgt tatacacaag tccaggagta  1140
aaagaggcgt atcttagttc accggaaaag cattttggaa ggagtaaaag gtttcttgct  1200
tcattagagg agaaaaatgg ttatgttaag gcagataaag tcatatcaga agatatcata  1260
gaggaagcta agatgttagc tacttgtgca tatgaggatg gcacacattg gggtcaagag  1320
attggttatt catacgattg tcatttggag agcacttta ctggttatct attacactgc   1380
aaagggtgga catctactta tttgtatcca gacaggccat cttttcttgg ttgtgcccca  1440
gttgatatgc aaggtttctc atcacagctc atcaaatggg ttgctgcact tacacaagct  1500
ggtttatcac atctcaatcc catcacttat ggtttgagta gtaggatgag gactctccaa  1560
tgcatgtgct atgcctattt gatgtatttc actctttatt cttggggaat ggttatgtat  1620
gctagtgttc cttctattgg cctttgtttt gacttccaag tctatcctga ggtacatgat  1680
```

```
ccgtggtttg cagtgtatgt gattgctttc atatcgacaa ttttggagaa tatgtcggag  1740
tcaattccag aagggggatc agttaaaacg tggtggatgg aatacagggc attgatgatg  1800
atgggagtta gcgcaatatg gttaggagga ttgaaagcta tatatgacaa gatagtcgga  1860
acacaaggag agaaattgta tttgtcggac aaggcaattg acaaggaaaa gctcaagaaa  1920
tacgagaagg gcaaatttga tttccaagga atagggatac ttgctctgcc actgatagca  1980
ttttccgtgt tgaacctcgt aggcttcatt gttggagcta atcatgtctt tattactatg  2040
aactacgcag gcgtgctggg ccaactcctc gtatcatcgt tcttcgtctt tgttgtcgtc  2100
actgttgtca ttgatgttgt atctttctta aaggtttctt aa                      2142

SEQ ID NO: 33          moltype = AA   length = 713
FEATURE                Location/Qualifiers
source                 1..713
                       mol_type = protein
                       organism = Solanum lycopersicum
SEQUENCE: 33
MKKTMELNKS TVPQPITTVY RLHMFIHSII MLALIYYRVS NLFKFENILS LQALAWALIT    60
FGEFSFILKW FFGQGTRWRP VERDVFPENI TCKDSDLPPI DVMVFTANPK KEPIVDVMNT   120
VISAMALDYP TDKLAVYLAD DGGCPLSLYA MEQACLFAKL WLPFCRNYGI KTRCPKAFFS   180
PLGDDDRVLK NDDFAAEMKE IKLKYEEFQQ KVEHAGESGK INGNVVPDRA SLIKVINERE   240
NEKSVDDMTK MPLLVYVSRE RRFNRLHHFK GGSANALLRV SGIMSNAPYV LVLDCDFFCH   300
DPISARKAMC FHLDPKLSSD LAYVQFPQVF YNVSKSDIYD VKIRQAYKTI WHGMDGIQGP   360
VLSGTGYFLK RKALYTSPGV KEAYLSSPEK HFGRSKRFLA SLEEKNGYVK ADKVISEDII   420
EEAKMLATCA YEDGTHWGQE IGYSYDCHLE STFTGYLLHC KGWTSTYLYP DRPSFLGCAP   480
VDMQGFSSQL IKWVAALTQA GLSHLNPITY GLSSRMRTLQ CMCYAYLMYF TLYSWGMVMY   540
ASVPSIGLLF DFQVYPEVHD PWFAVYVIAF ISTILENMSE SIPEGGSVKT WWMEYRALMM   600
MGVSAIWLGG LKAIYDKIVG TQGEKLYLSD KAIDKEKLKK YEKGKFDFQG IGILALPLIA   660
FSVLNLVGFI VGANHVFITM NYAGVLGQLL VSSFFVFVVV TVVIDVVSFL KVS          713

SEQ ID NO: 34          moltype = DNA   length = 2142
FEATURE                Location/Qualifiers
source                 1..2142
                       mol_type = genomic DNA
                       organism = Solanum pennellii
SEQUENCE: 34
atgaaaaaaa ccatggagct caacaaaagc actgttccac aacctatcac caccgtatac    60
cgactccaca tgttcatcca ctcaataatc atgcttgcat taatatacta ccgtgtatct   120
aatttgttta aattcgaaaa cattctcagt ttacaagcac ttgcttggct actcatcact   180
tttggtgaat ttagtttcat tctcaagtgg ttcttcggac aaggaactcg ttggcgcccc   240
gttgaacgag atgttttccc tgaaaacatt acttgcaaag attccgatct accgccaatt   300
gacgtaatgg tgttcactgc caatcctaag aaagagccaa ttgtagatgt catgaacact   360
gtgatatccg caatggctct tgattatccc accgataaat tggctgtgta tctggccgat   420
gatggaggat gtccattgtc cttgtacgcc atggaacaag catgttttgt tgcaaagcta   480
tggttacctt tctgtagaaa tgtatggaat aaaacgaagc gcccaaaagc attttttcct   540
ccgttaggag atgatgaccg tgttcttaag aatgatgatt ttgctgctga atgaaaagaa   600
attaaattga aatatgaaga gttccagcag aacgtggaac atgctggtga atctggaaaa   660
atcaatggca acgtagtgcc tgacagagct tcgcttatta aggtaataaa cgagagggag   720
aacgaaaaga gtgtcgatga tttaacgaaa atgccctttgc tagtttatgt atcccgtgaa   780
agaagattca accgtcttca tcatttcaag ggtggatctg caaatgctct acttcgagtt   840
tctggaataa tgagtaatgc ccccatgta ctggtgttag attgtgatt cttctgtcat   900
gatccgtatt cagctaggaa agcaatgtgt tttcatcttg atccaaagct atcatctgat   960
ttagcctatg ttcagttccc tcaagtcttt tacaatgtca gcaagtccga tatttatgat  1020
gtcaaaatta gacaggctta caagacaata tggcatggaa tggatggtat ccaaggccca  1080
gtgttatctg gaactggtta ttttctcaag aggaaggcgt tatacacaag tccaggagta  1140
aaagaggcgt atcttagttc accggaaaag catttttgga ggagtaaaaa gttccttgct  1200
tcattagagg agaaaaatgg ttatgttaag gcagataaga tcatatcaga agatatcata  1260
gaggaagcta agatcttagc tacttgtgca tatgaggatg gcacacattg gggtcaaagc  1320
attggttatt catacgattg tcatttggag agcacttttta ctggttatct attacactgc  1380
aaagggtgga catctactta tttgtatcca gacaggccat cttttcttgg ttgtgcccca  1440
gttgatatgc aaggtttctc atcacagctc ataaaatggg ttgctgcact tacacaagct  1500
ggtctatcac atctcaatcc catcacttat ggtttagta gtaggatgag aactctccaa  1560
tgcatgtgct atgccatttt gatgtatttc actctttatt cttggggaat ggttatgtat  1620
gctagtgttc cttctattgg ccttttgttt ggcttccaag tctaccctga ggtacatgat  1680
ccatggtttg cagtgtatgt gattgctttc atatcgacaa ttttggagaa tatgtcggag  1740
tcaattccag aagggggatc agttaaaacg tggtggatgg aatacagggc attgatgatg  1800
atgggagtta gcgcaatatg gttaggagga ttgaaagcta tatatgacaa gatagtcgga  1860
acacaaggag agaaattgta tttgtcggac aaggcaattg acaaggaaaa gctcaagaaa  1920
tacgagaagg gcaaatttga tttccaagga atagggatac ttgctctgcc attgatagca  1980
ttttccgtgt tgaacctcgt aggcttcatt gttggagcta atcatgtctt tattactatg  2040
aactacgcag gcgtgctggg ccaactcctc gtatcatcat tcttcgtctt tgttgtcgtc  2100
actgttgtca ttgatgttgt atctttctta aaggtttctt aa                      2142

SEQ ID NO: 35          moltype = AA   length = 713
FEATURE                Location/Qualifiers
source                 1..713
                       mol_type = protein
                       organism = Solanum pennellii
SEQUENCE: 35
MKKTMELNKS TVPQPITTVY RLHMFIHSII MLALIYYRVS NLFKFENILS LQALAWLLIT    60
FGEFSFILKW FFGQGTRWRP VERDVFPENI TCKDSDLPPI DVMVFTANPK KEPIVDVMNT   120
```

```
VISAMALDYP TDKLAVYLAD DGGCPLSLYA MEQACLFAKL WLPFCRKYGI KTRCPKAFFS    180
PLGDDDRVLK NDDFAAEMKE IKLKYEEFQQ NVEHAGESGK INGNVVPDRA SLIKVINERE    240
NEKSVDDLTK MPLLVYVSRE RRFNRLHHFK GGSANALLRV SGIMSNAPYV LVLDCDFFCH    300
DPISARKAMC FHLDPKLSSD LAYVQFPQVF YNVSKSDIYD VKIRQAYKTI WHGMDGIQGP    360
VLSGTGYFLR RKALYTSPGV KEAYLSSPEK HFGRSKKFLA SLEEKNGYVK ADKVISEDII    420
EEAKILATCA YEDGTHWGQE IGYSYDCHLE STFTGYLLHC KGWTSTYLYP DRPSFLGCAP    480
VDMQGFSSQL IKWVAALTQA GLSHLNPITY GLSSRMRTLQ CMCYAYLMYF TLYSWGMVMY    540
ASVPSIGLLF GFQVYPEVHD PWFAVYVIAF ISTILENMSE SIPEGGSVKT WWMEYRALMM    600
MGVSAIWLGG LKAIYDKIVG TQGEKLYLSD KAIDKEKLKK YEKGKFDFQG IGILALPLIA    660
FSVLNLVGFI VGANHVFITM NYAGVLGQLL VSSFFVFVVV TVVIDVVSFL KVS           713

SEQ ID NO: 36           moltype = DNA   length = 2148
FEATURE                 Location/Qualifiers
source                  1..2148
                        mol_type = genomic DNA
                        organism = Solanum tuberosum
SEQUENCE: 36
atgaaaaaaa ccatggagct caacaaaagc actgttccac aacctatcac caccatatac    60
cgactccaca tgtttatcca ctctataatc atggttgcat taatatacta ccgtgtatct    120
aatttgttta aattcgaaaa cattctgagt ttacaagcac ttgcttgggt actcatcact    180
tttggtgaat ttagtttcat tctccaagtgg ttccttcgga caaggaactcg ttatcgccct    240
gttgaaagag atgttttccc tgaaaacata acttgcaaag attccgatct accaccaatt    300
gacgtaatgg tattcactgc caatcctaag aaagagccaa ttgtggatgt catgaaccat    360
gtgatatccg caatggctct tgattatcct acggataaat tggctgtgta tctggctgat    420
gatgaggat gtcctttgtc attgtacgcc atggaagagg catgtgtgtt tgcaaagctg    480
tggctacctt tctgtaggaa gtatggaatt aaaactagat gccctaaagc gttttttcct    540
cctttaggag atgatgaacg tgttcttaag aatgatgatt ttgatgctga atgaaagaa    600
attaaattga aatatgaaga gttccagcag aatgtggaac gtgctggtga atctggaaaa    660
atcaatggta acgtagtgcc tgatagagcc tcgtttatta aggtaataaa cgacagaaaa    720
gcggagagcg aaaagagtgc cgatgattta acgaaaatgc ccttgctagt ttatgtatcc    780
cgtgaaagaa gattcaaccg tcttcatcac ttcaagggtg gatctgcaaa tgctcttctt    840
cgagtttctg gaataatgag taatgccccc tatatactgg tgttagattg tgatttcttc    900
tgtcatgatc caatatcagc taggaaggca atgtgttttc atcttgatcc aaagctatca    960
tctgatttag cttatgttca gttccctcaa gtcttttaca atgtcagcaa gtccgatatt    1020
tatgatgtca aaattagaca ggcttacaag acaatatggc atggaatgga tggtatccaa    1080
ggcccagtgt tatcaggaac tggttatttt ctgaagagga aggcgttata cacgagtcca    1140
ggagtaaagg aggagtatct tagttcaccg gaaaagcatt ttggaaggag taaaaagttc    1200
cttgcttcac tagaggagaa aaatggttat gttaaggcag agaaagtcat atcagaagat    1260
atcgtagagg aagctaagac cttagctact tgtgcatatg aggatggcac acattgggt    1320
caagagattg ttattcata cgattgtcat tggagagca cttttactgg ttatctatta    1380
cactgcaaag ggtggagatc gacttatttg tatccagaca ggccatcttt cttgggttgt    1440
gccccagttg atatgcaagg tttctcctca cagctcataa aatgggttgc tgcacttaca    1500
caagctggtt tatcacatct caatcccatc acttatggct tagtagcag gatgaaaact    1560
ctccaatgca tgtgctatgc ctattttgata tatttcactc tttattcttg gggaatggtt    1620
ctatatgcta gtgttccttc tattggcctt ttgtttggct tccaagtcta tcccgatgta    1680
catgatccat ggttttgcagt gtatgtgatt gctttcatat cggcaatttt ggagaatatg    1740
tcggagtcaa ttcctgatgg gggatcattt aaatcttggt ggatggaata cagggcactg    1800
atgatgatgg gagttagtgc aatatggtta ggaggattga agctatatt agacaggata    1860
atcggaacag aaggagagaa attgtattta tcggacaagg caattgacaa ggaaaagctc    1920
aagaaatacg agaaggggaa atttgatttc aaggaatag gatacttgc tgtaccattg    1980
atagcatttt ccttgttgaa cctcgtaggc ttcattgttg gagctaatca tgtctttatt    2040
actatgaact acgcaggtgt gcttggccaa ctcctcgtat catccttctt cgtctttgtc    2100
gtggtcactg ttgtcattga tgtcgtttct ttcttaaagg tttcttaa                2148

SEQ ID NO: 37           moltype = AA   length = 711
FEATURE                 Location/Qualifiers
source                  1..711
                        mol_type = protein
                        organism = Solanum tuberosum
SEQUENCE: 37
MELNKSTVPQ PITTIYRLHM FIHSIIMVAL IYYRVSNLFK FENILSLQAL AWVLITFGEF    60
SFILKWFFGQ GTRYRPVERD VFPENITCKD SDLPPIDVMV FTANPKKEPI VDVMNTVISA    120
MALDYPTDKL AVYLADDGGC PLSLYAMEEA CVFAKLWLPF CRKYGIKTRC PKAFFSPLGD    180
DERVLKNDDF DAEMKEIKLK YEEFQQNVER AGESGKINGN VVPDRASFIK VINDRKAESE    240
KSADDLTKMP LLVYVSRERR FNRLHHFKGG SANALLRVSG IMSNAPYILV LDCDFFCHDP    300
ISARKAMCFH LDPKLSSDLA YVQFPQVFYN VSKSDIYDVK IRQAYKTIWH GMDGIQGPVL    360
SGTGYFLKRK ALYTSPGVKE EYLSSPEKHF GRSKKFLASL EEKNGYVKAE KVISEDIVEE    420
AKTLATCAYE DGTHWGQEIG YSYDCHLEST FTGYLLHCKG WRSTYLYPDR PSFLGCAPVD    480
MQGFSSQLIK WVAALTQAGL SHLNPITYGF SSRMKTLQCM CYAYLIYFTL YSWGMVLYAS    540
VPSIGLLFGF QVYPDVHDPW FAVYVIAFIS AILENMSESI PDGGSFKSWW MEYRALMMG    600
VSAIWLGGLK AILDRIIGTE GEKLYLSDKA IDKEKLKKYE KGKFDFQGIG ILAVPLIAFS    660
LLNLVGFIVG ANHVFITMNY AGVLGQLLVS SFFVFVVVTV VIDVVSFLKV S             711
```

```
SEQ ID NO: 38            moltype = DNA  length = 2148
FEATURE                  Location/Qualifiers
source                   1..2148
                         mol_type = genomic DNA
                         organism = Solanum chacoense
SEQUENCE: 38
atgaaaaaaa ccatggagct caacaaaagc actgttccac aacctatcac caccatatac   60
cgactccaca tgttcgtcca ttctataatc atggctgcat taatatacta ccgtgtatct  120
aatttgttta aattcgaaaa cattctgagt ttacaagcac ttgcttgggt actcatcact  180
tttggtgaat ttagtttcat tctcaagtgg ttcttcggac aaggaactcg ttggcgccct  240
gttgaaagag atgttttccc tgaaaacata acttgcaaag attccgatct accaccaatt  300
gacgtaatgg tattcactgc caatcctaag aaagagccaa ttgtggatgt catgaacact  360
gtgatatccg caatggctct agattatcct acggataaat tggctgtgta tctggctgat  420
gatggaggat gtcctttgtc attgtacgcc atggaagaag catgtgttaa ttgcaaagctg  480
tggctacctt tctgtaggaa gtatggaatt aaaaccagat gccctaaagc gtttttttct  540
cctttaggag atgatgaccg tgttcttaag aatgatgatt ttgatgctga atgaaagaa   600
attaaattga aatatgaaga gttccagcag aatgtggaac gtgctggtga atctggaaaa  660
atcaatggta acgtagtgcc tgatagagcc tcgtttatta aggtaataaa cgacagaaa  720
acggagagcg aaaagagtgc cgatgattta acgaaaatgc ccttgctagt ttatgtatcc  780
cgtgaaagaa gattcaaccg tcttcatcac ttcaagggtg gatctgcaaa tgctcttctt  840
cgagtttctg gaataatgag taatgcccc tatatactgg tgttagattg tgattcttc    900
tgtcatgatc caatatcagc taggaaggca atgtgtttc atcttgatcc aaagctatca  960
tctgatttag cttatgttca gttccctcaa gtcttttaca atgtcagcaa gtccgatatt 1020
tatgatgtca aaattagaca ggcttacaag acaatatggc atggaatgga tggtatccaa 1080
ggcccagtgt tatcaggaac tggttatttt ctgaagagga aggcgttata cacgagtcca 1140
ggagtaaagg aggagtatct tagttcaccg gaaaagcatt ttggaaggag taaaaagttc 1200
cttgcttcac tagaggagaa aaatggttat gttaaggcag agaaagtcat atcagaagat 1260
atcgtagagg aagctaagac cttagctact tgtgcatatg aggatggtac acattggggt 1320
caagagatcg gttattcata cgattgtcat ttggagagca cttttactgg ttatctatta 1380
cactgcaaag ggtgacatc gacttatttg tatccagaca gccatctttt cttgggttgt 1440
gctccagttg atatgcaagg tttctcctca cagctcataa aatggggttgc tgcacttaca 1500
caagctggtt tatcacatct caatcccatc acttatggct tgagtagcag gatgaaaact 1560
ctccaatgca tgtgctatgc ctatttgata tatttcactc tttattcttg gggaatggtt 1620
ctatatgca gtattccttc tattggtctt ttgtttggct tccaagtcta tccggaggta 1680
catgatccat ggtttgcagt gtatgtgatt gctttcatat cgacaattt ggagaatatg 1740
tcggagtcaa ttccagaagg gggatcattt aaatcgtggt ggatggaata cagggcactg 1800
atgatgatgg gagttagtgc aatatggta ggaggattga agctatatt agacaagata 1860
atcggaacag aaggagagaa attgtatttg tcagacaagg caattgacaa ggaaaagctc 1920
aagaaatacg agaagggaa atttgatttc caaggaactg gatacttgc tgtaccattg 1980
atagcatttt ccctgttgaa cctggtaggc ttcattgttg gagctaatca tgtctttatt 2040
actatgaact acgcaggtgt gcttggccaa ctcctcgtat catccttctt cgtctttgtc 2100
gtggtcactg ttgtcattga tgtcgtttct ttcttaaagg tttcttaa              2148

SEQ ID NO: 39            moltype = AA  length = 715
FEATURE                  Location/Qualifiers
source                   1..715
                         mol_type = protein
                         organism = Solanum chacoense
SEQUENCE: 39
MKKTMELNKS TVPQPITTIY RLHMFVHSII MAALIYYRVS NLFKFENILS LQALAWVLIT   60
FGEFSFILKW FFGQGTRWRP VERDVFPENI TCKDSDLPPI DVMVFTANPK KEPIVDVMNT  120
VISAMALDYP TDKLAVYLAD DGGCPLSLYA MEEACVFAKL WLPFCRKYGI KTRCPKAFFS  180
PLGDDDRVLK NDDFDAEMKE IKLKYEEFQQ NVERAGESGK INGNVVPDRA SFIKVINDRK  240
TESEKSADDL TKMPLLVYVS RERRFNRLHH FKGGSANALL RVSGIMSNAP YILVLDCDFF  300
CHDPISARKA MCFHLDPKLS SDLAYVQFPQ VFYNVSKSDI YDVKIRQAYK TIWHGMDGIQ  360
GPVLSGTGYF LKRKALYTSP GVKEEYLSSP EKHFGRSKKF LASLEEKNGY VKAEKVISED  420
IVEEAKTLAT CAYEDGTHWG QEIGYSYDCH LESTFTGYLL HCKGWTSTYL YPDRPSFLGC  480
APVDMQGFSS QLIKWVAALT QAGLSHLNPI TYGLSSRMKT LQCMCYAYLI YFTLYSWGMV  540
LYASIPSIGL LFGFQVYPEV HDPWFAVYVI AFISTILENM SESIPEGGSF KSWWMEYRAL  600
MMMGVSAIWL GGLKAILDKI IGTEGEKLYL SDKAIDKEKL KKYEKGKFDF QGIGILAVPL  660
IAFSLLNLVG FIVGANHVFI TMNYAGVLGQ LLVSSFFVFV VVTVVIDVVS FLKVS        715

SEQ ID NO: 40            moltype = DNA  length = 2058
FEATURE                  Location/Qualifiers
source                   1..2058
                         mol_type = genomic DNA
                         organism = Solanum melongena
SEQUENCE: 40
atgaaaaaac aaatggagct caacagaagt gttgtaccgc aacctatcac caccatttac   60
cgtctccaca tgtttatcca tgccctaatc atgctagcac taatatacta ccgtgtctct  120
aatttggcca aattcgaaaa catcctcagt ttacaagcac ttgcttgggc tcttatcacg  180
ttaggtgaac tttgtttcat agtcaagtgg ttcttcggac aagggactcg ttggcgtcct  240
gttgataggg atgtcttccc tgaaaacatc acttgtccag attccgagct accccccatt  300
gatgtcatgg ttttcactgc aaatcctaag aaagagccta ttgtggatgt catgaacact  360
gtcatatccg caatggctct tgattacccg accgacaaat tggccgttta tttgtctgat  420
gatggaggat gcccccttga cgttgtacgca atggaggaag cttgttccctt tgccaagttg  480
tggctaccctt tttgtaggaa gtatggaatc aaaaacaaggt gccctaaggc gtttttttct  540
ccattaggag aagatgaccg tgtattgaag agtgatgact tgtttctga atgaaagaa   600
atgaagtcaa aatatgaaga gttccagcag aacgtggacc gtgctggtga atccggaaaa  660
```

| atcaaaggtg | acgtagtgcc | tgatagaccc | gcgtttctta | aggtactaaa | tgacaggaag | 720 |
| acggagaacg | agaagagtgc | agacgattta | actaaaatgc | ctttgctagt | atacgtatcc | 780 |
| cgtgaaagaa | gaactcaccg | tcgccatcac | ttcaagggtg | gatctgcaaa | tgctcttctt | 840 |
| cgagtttctg | gataatcag | taatgccccc | tatatactgg | ttttagattg | tgatttcttc | 900 |
| tgtcatgatc | caatatcagc | tcggaaggca | atgtgtttcc | atctgatcc | aaaactatca | 960 |
| cctgacttag | cttacgtgca | gttccctcaa | gtgttttaca | atgttagcaa | gtccgatatt | 1020 |
| tacgacgtca | aaattagaca | ggcttacaag | acaatatggc | acgggatgga | tggtatccaa | 1080 |
| ggcccagtgt | tatcgggaac | tggttatttt | ttaaaaaaga | aggcgttgta | cacgagtcca | 1140 |
| ggtctaaaag | atgagtatct | tagttcaccg | gaaaagcatt | cggaaccgag | tagaaagttc | 1200 |
| attgcttcac | tagaggagaa | taattatgtt | aagcaagaga | aagtcatatc | agaagatatc | 1260 |
| atagaggaag | ctaagagact | ggctacttgt | gcatacgagg | atggcacaca | ttgggggtcaa | 1320 |
| gaggcaaaca | ggccatcttt | cttgggttgt | gccccagttg | atatgcaagg | tttctcctca | 1380 |
| cagctcataa | aatgggttgc | tgcactcaca | caagcaggtc | tatccatcat | caatcccatc | 1440 |
| acttacggct | tcaagagcag | aatgaaact | ctccaagtct | tgtgttatgc | ctatttgatg | 1500 |
| tatttctctc | tttattcttg | gggaatggtt | ctacatgcta | gtgttccttc | tattggcctt | 1560 |
| ctctctggca | ttaaaatcta | cccgagggtg | tatgatccat | ggtttgttgt | gtatgtgatt | 1620 |
| gctttcatat | caacaatttt | ggagaatatg | tcggaatcaa | ttccgaagg | gggatcggtt | 1680 |
| aaaacgtggt | ggatggaata | cagggcactg | atgatgatgg | gagttagtgc | aaatatggcta | 1740 |
| ggaggagtga | aagccatagt | agacaagatc | atcggaacgc | aaggagagaa | attgtatttg | 1800 |
| tcggacaaag | caattgacaa | ggaaaagctc | aagaaatacg | agaagggaa | atttgatttc | 1860 |
| caaggaatag | gaatacttgc | tgtaccattg | ataacatttt | ctgtgttgaa | cctggtaggc | 1920 |
| ttcttggttg | gaattaatca | agtgttgata | acgatgaagt | tcgcaggcgt | gctgggcaa | 1980 |
| ctcctcgtat | catccttctt | cgtctttgtc | gtcgttactg | ttgtcattga | tgtcgtatct | 2040 |
| ttcttaaagg | attcttaa | | | | | 2058 |

| SEQ ID NO: 41 | moltype = AA length = 685 |
| FEATURE | Location/Qualifiers |
| source | 1..685 |
| | mol_type = protein |
| | organism = Solanum melongena |

SEQUENCE: 41

| MKKQMELNRS | VVPQPITTIY | RLHMFIHALI | MLALIYYRVS | NLAKFENILS | LQALAWALIT | 60 |
| LGELCFIVKW | FFGQGTRWRP | VDRDVFPENI | TCPDSELPPI | DVMVFTANPK | KEPIVDVMNT | 120 |
| VISAMALDYP | TDKLAVYLSD | DGGCPLTLYA | MEEACSFAKL | WLPFCRKYGI | KTRCPKAFFS | 180 |
| PLGEDDRVLK | SDDFVSEMKE | MKSKYEEFQQ | NVDRAGESGK | IKGDVVPDRP | AFLKVLNDRK | 240 |
| TENEKSADDL | TKMPLLVYVS | RERRTHRRHH | FKGGSANALL | RVSGIISNAP | YILVLDCDFF | 300 |
| CHDPISARKA | MCFHLDPKLS | PDLAYVQFPQ | VFYNVSKSDI | YDVKIRQAYK | TIWHGMDGIQ | 360 |
| GPVLSGTGYF | LKKKALYTSP | GLKDEYLSSP | EKHFGTSRKF | IASLEENNYV | KQEKVISEDI | 420 |
| IEEAKRLATC | AYEDGTHWGQ | EANRPSFLGC | APVDMQGFSS | QLIKWVAALT | QAGLSHLNPI | 480 |
| TYGFKSRMRT | LQVLCYAYLM | YFSLYSWGMV | LHASVPSIGL | LSGIKIYPEV | YDPWFVVYVI | 540 |
| AFISTILENM | SESIPEGGSV | KTWWMEYRAL | MMMGVSAIWL | GGVKAIVDKI | IGTQGEKLYL | 600 |
| SDKAIDKEKL | KKYEKGKFDF | QGIGILAVPL | ITFSVLNLVG | FLVGINQVLI | TMKFAGVLGQ | 660 |
| LLVSSFFVFV | VVTVVIDVVS | FLKDS | | | | 685 |

| SEQ ID NO: 42 | moltype = DNA length = 2136 |
| FEATURE | Location/Qualifiers |
| source | 1..2136 |
| | mol_type = genomic DNA |
| | organism = Capsicum annuum |

SEQUENCE: 42

| atggagctca | acagatgtac | ggtgcagcaa | cctaccactg | ccatataccg | actacacatg | 60 |
| tttctccact | ctctaatcat | gcttgcatta | gtatactatc | gtttgtctaa | tctgttttac | 120 |
| ttcgaaaacg | tcctcacttt | acaagcattt | gcatgggggc | ttatcacctt | aggtgaaatt | 180 |
| tgtttcattg | tcaagtggtt | ctttggtcaa | gggactcgtt | ggcgcccgt | tgtcaggaa | 240 |
| gtgttcctgg | acaatattac | ttgccaagat | tccgagctgc | ccgactacga | tgtgatggtt | 300 |
| ttcactgcca | atcccaagaa | agagccaatt | gtggatgtca | tgaacactgt | gatatccgca | 360 |
| atggctcttg | attacccgac | ggataaattg | gctgtgtatc | tggctgatga | tggaggatgc | 420 |
| cccttgacgt | tgtacgccat | ggaggaggcc | tgttcttttg | ccaagttgtg | gctaccttc | 480 |
| tgtaggaagt | atggaaatcaa | acaaggtgc | cccaaagcgt | ttttttctcc | attaggagaa | 540 |
| gatgatcgta | tccttaagaa | cgatgctttt | gtagctgaaa | tgaaagaaat | taattaaaa | 600 |
| tatgaggagt | tccagcagaa | tgtaaacctt | gctggtgaat | ccggaaaaat | caaaggtgac | 660 |
| gtagtgcctg | atagagcctc | gtttattaag | gtaataaatg | acaggaaaat | ggagaacaag | 720 |
| aagagtgccg | acgatataac | gaaaatgcct | tgctagtat | acgtatccg | tgaagaaga | 780 |
| tttaacagtc | gtcatcactt | caagggtgga | tctgcaaata | ctcttcttcg | agtttcaggg | 840 |
| ataatgagta | atgcccccta | tttactggtc | ttagattgtg | atttcttctg | tcatgatcca | 900 |
| acatcagctc | ggaaggcaat | gtgtttccat | cttgatccaa | aactatcacc | ttccttagct | 960 |
| tatgtgcagt | tccctcaagt | gttttacaat | gtcagcaagt | ccgatatata | cgatgtcaaa | 1020 |
| attagacagg | cttacaagac | aatatggcac | ggaatggatg | gtatccaagg | cccagtgtta | 1080 |
| tcgggaactg | ggtattttct | gaagaggaaa | gcgttataca | cgagtccagg | tctaaaggat | 1140 |
| gagtatctta | tttcaccgga | aaagcatttc | ggatcaagta | gaaagttcat | tgcttctcta | 1200 |
| gaggagaaca | atggttatgt | aagcaagag | aaactcataa | cagaagatat | tatagaggaa | 1260 |
| gcgaagacct | tgtctacttg | tgcatacgag | gatggtacac | gatggggcga | agagatcggt | 1320 |
| tatacctaca | attgccattt | ggagagcact | tttaccggct | atcttttgca | ctgcaaaggg | 1380 |
| tggacatcaa | catatttgta | tccagaaagg | ccatttttgc | tgggttgtgc | cccagttgat | 1440 |
| atgcaaggat | tctcctcaca | actcacaaaa | tgggttgctg | cactcacaca | agctggtcta | 1500 |
| tcacatctca | atcccatcac | ttacggcatg | aagagcagga | ttaagactat | ccaatgcttg | 1560 |
| tgctatgcct | atttgatgta | tttctctctc | tattcttggg | gaatggttct | gcatgctagt | 1620 |
| gttccttcta | ttagccttt | gcttggcatt | caagtctacc | ccgaggtcta | tgatccatgg | 1680 |
| tttgcagtgt | atgtgcttgc | tttcatatcg | acaatttgg | agaacatgtc | agagtcaatt | 1740 |

```
ccagaaggcg gttcagttaa aacttggtgg atggaataca gggcactgat gatgatggga    1800
gttagtgcaa tatggttagg aggagtgaaa gctatagtag aaaagatcat cggaactcaa    1860
ggagagaaat tatatttgtc ggacaaagca attgacaagg aaaagctcaa gaaatatgag    1920
aaggggaaat ttgatttcca agggataggg atacttgctg ttccattgat aacattctca    1980
gcgttgaatt tggtaggctt catgttggga gctaatcaag tgattcttac tatgaagttc    2040
gaagctttgc taggccaact ccttgtgtca tccttcttcg tctttgtggt ggtcaccgtt    2100
gtcatagatg tcctatcttt cttaaaagac tcttaa                              2136

SEQ ID NO: 43         moltype = AA  length = 711
FEATURE               Location/Qualifiers
source                1..711
                      mol_type = protein
                      organism = Capsicum annuum
SEQUENCE: 43
MELNRCTVQQ PTTAIYRLHM FLHSLIMLAL VYYRLSNLFY FENVLTLQAF AWGLITLGEI     60
CFIVKWFFGQ GTRWRPVVRE VFLDNITCQD SELPALDVMV FTANPKKEPI VDVMNTVISA    120
MALDYPTDKL AVYLADDGGC PLTLYAMEEA CSFAKLWLPF CRKYGIKTRC PKAFFSPLGE    180
DDRILKNDDF VAEMKEIKLK YEEFQQNVNL AGESGKIKGD VVPDRASFIK VINDRKMENK    240
KSADDITKMP LLVYVSRERR FNSRHHFKGG SANALLRVSG IMSNAPYLLV LDCDFFCHDP    300
TSARKAMCFH LDPKLSPSLA YVQFPQVFYN VSKSDIYDVK IRQAYKTIWH GMDGIQGPVL    360
SGTGYFLKRK ALYTSPGLKD EYLISPEKHF GSSRKFIASL EENNGYVKQE KLITEDIIEE    420
AKTLSTCAYE DGTRWGEEIG YTYNCHLEST FTGYLLHCKG WTSTYLYPER PSFLGCAPVD    480
MQGFSSQLTK WVAALTQAGL SHLNPITYGM KSRIKTIQCL CYAYLMYFSL YSWGMVLHAS    540
VPSISLLLGI QVYPEVYDPW FAVYVLAFIS TILENMSESI PEGGSVKTWW MEYRALMMMG    600
VSAIWLGGVK AIVEKIIGTQ GEKLYLSDKA IDKEKLKKYE KGKFDFQGIG ILAVPLITFS    660
ALNLVGFMVG ANQVILTMKF EALLGQLLVS SFFVFVVVTV VIDVLSFLKD S             711

SEQ ID NO: 44         moltype = DNA  length = 270
FEATURE               Location/Qualifiers
source                1..270
                      mol_type = other DNA
                      organism = synthetic construct
                      note = Solanum lycopersicum
SEQUENCE: 44
ggctcttgat tatcccaccg ataaattggc tgtgtatctc gctgatgatg gaggatgtcc     60
attgtcgttg tacgccatgg aacaagcgtg tttgtttgca aagctatggt tacctttctg    120
tagaaactat ggaattaaaa cgagatgccc aaaagcattt ttttctccgt taggagatga    180
tgaccgtgtt cttaagaatg atgattttgc tgctgaaatg aaagaaatta aattgaaata    240
tgaagagttc cagcagaagg tggaacatgc                                     270

SEQ ID NO: 45         moltype = DNA  length = 275
FEATURE               Location/Qualifiers
source                1..275
                      mol_type = other DNA
                      organism = synthetic construct
                      note = Solanum tuberosum
SEQUENCE: 45
ggctcttgat tatcctacgg ataaattggc tgtgtatctg gctgatgatg gaggatgtcc     60
tttgtcattg tacgccatgg aagaagcatg tgtgtttgca aagctgtggc tacctttctg    120
taggaagtat ggaattaaaa ctagatgccc taaagcgttt ttttctcctt taggagatga    180
tgaacgtgtt cttaagaatg atgattttga tgctgaaatg aaagaaatta aattgaaata    240
tgaagagttc cagcagaatg tggaacgtgc tggtg                               275

SEQ ID NO: 46         moltype = DNA  length = 447
FEATURE               Location/Qualifiers
source                1..447
                      mol_type = other DNA
                      organism = synthetic construct
                      note = Solanum melongena
SEQUENCE: 46
ggctcttgat tacccgaccg acaaattggc cgtttatttg tctgatgatg gaggatgccc     60
cttgacgttg tacgcaatgg aggaagcttg ttcctttgcc aagttgtggc tactttttg     120
taggaagtat ggaatcaaaa caaggtgccc taaggcgttt ttttctccat taggagaaga    180
tgaccgtgta ttgaaagtg atgactttgt ttctgaaatg aaagaaatga agtcaaaata    240
tgaagagttc cagcagaacg tggaccgtgc tggtgaatcc ggaaaaatca aaggtgacgt    300
agtgcctgat agacccgcgt ttcttaaggt actaaatgac aggaagacgg agaacgagaa    360
gagtgcagac gatttaacta aaatgccttt gctagtatac gtatcccgtg aaagaagaac    420
tcaccgtcgc catcacttca agggtgg                                        447
```

US 11,957,102 B2

PLANT WITH ALTERED CONTENT OF STEROIDAL ALKALOIDS

CROSS-REFERENCE TO RELATED APPLICATIONS

This application is a divisional application of U.S. application Ser. No. 17/008,875 filed Sep. 1, 2020 as a divisional application of United States application Ser. No. 16/123,248 filed Sep. 6, 2018, which filed as a continuation-in-part application of U.S. patent application Ser. No. 14/895,059 filed Dec. 1, 2015, which filed as a National Phase Application of PCT International Application No. PCT/IL2014/050497, International filing date Jun. 2, 2014, which claims the benefit of U.S. Provisional Application Ser. No. 61/831,164 filed Jun. 5, 2013; which are hereby incorporated by reference.

SEQUENCE LISTING STATEMENT

The instant application contains a Sequence Listing which has been submitted electronically in XML file format and is hereby incorporated by reference in its entirety. Said XLM copy, created on Aug. 5, 2022, is named P-79520-US3_SL.xml and is 81,885 bytes in size.

FIELD OF THE INVENTION

The present invention relates to key genes in the biosynthesis of steroidal alkaloids and steroidal saponins and to genetically modified or gene edited plants with altered content of steroidal alkaloids, steroidal saponins, or phytosterols, particularly to Solanaceous crop plants with reduced content of antinutritional steroidal glycoalkaloids or increased content of phytosterols, including cholesterol, cholestanol, and any of their modified glycosylated derivatives.

BACKGROUND OF THE INVENTION

The plant kingdom produces hundreds of thousands of different small compounds that are often genus or family specific. These molecules, referred to as secondary metabolites, are not vital to cells that produce them, but contribute to the overall fitness of the organisms. Alkaloids are one example of secondary metabolites. They are low molecular weight nitrogen-containing organic compounds, typically with a heterocyclic structure. Alkaloid biosynthesis in plants is tightly controlled during development and in response to stress and pathogens.

The broad group of triterpenoid-alkaloid compounds is widespread in plants and derived from the cytosolic mevalonic acid isoprenoid biosynthetic pathway. Steroidal saponins and Steroidal alkaloids are two large classes of triterpenoids produced by plants. Steroidal alkaloids (SAs), occasionally known as "*Solanum* alkaloids," are common constituents of numerous plants belonging to the Solanaceae family, which includes the genera *Solanum* and *Capsicum*, as well as many others. Steroidal alkaloids are also produced by a large number of species in the Liliaceae family.

Estimated in the order of 1350 species, *Solanum* is one of the largest genera of flowering plants, representing about a half of the species in the Solanaceae. Diverse structural composition and biological activity, as well as occurrence in food plants including tomato (*Solanum lycopersicum*), potato (*Solanum tuberosum*) and eggplant (*Solanum melongena*), made SAs the subject of extensive investigations (Eich E. 2008. Solanaceae and Convolvulaceae—secondary metabolites: biosynthesis, chemotaxonomy, biological and economic significance: a handbook. Berlin: Springer).

Consisting of a C-27 cholestane skeleton and a heterocyclic nitrogen component, SAs were suggested to be synthesized in the cytosol from cholesterol. Conversion of cholesterol to the alkamine SA should require several hydroxylation, oxidation and transamination reactions (Eich 2008, supra), and in most cases further glycosylation to form steroidal glycoalkaloids (SGAs) (Arnqvist L. et al. 2003. Plant Physiol 131:1792-1799). The oligosaccharide moiety components of SGAs directly conjugate to the hydroxyl group at C-3, β of the alkamine steroidal skeleton (aglycone). The oligosaccharide moiety includes D-glucose, D-galactose, L-rhamnose, D-xylose, and L-arabinose, the first two monosaccharides being the predominant units.

Steroidal glycoalkaloids (SGAs) are nitrogen-containing, cholesterol-derived specialized metabolites produced by numerous members of the Solanaceae family. Examples of these compounds include α-tomatine and dehydrotomatine in tomato (*Solanum lycopersicum*), α-chaconine and α-solanine in potato (*Solanum tuberosum*), and α-solamargine and α-solasonine in eggplant (*Solanum melongena*). SGAs are also found in various types of peppers in the genus *Capsicum*. SGAs contribute to plant resistance to a wide range of pathogens and predators, including bacteria, fungi, oomycetes, viruses, insects, and larger animals. Some of them (e.g., α-chaconine and α-solanine in potato) are considered as anti-nutritional compounds to humans due to their toxic effects. More than 100 SGAs have been identified in tomatoes (Itkin et al., 2011, Plant Cell 23:4507-4525), and more than 50 have been identified in potatoes (Shakya and Navarre, 2008, J. Agric. Food Chem. 56:6949-6958). Eggplant also contains at least one variety of SGA (Friedmann, 2006, J. Agric. Food Chem. 54:8655-8681).

SGA biosynthesis depends on genes encoding UDP-glycosyltransferases (UGTs) that decorate the aglycone with various sugar moieties (McCue K F et al., 2005. Plant Sci. 168:267-273; Itkin M et al., 2011. Plant Cell 23:4507-4525). The tomato GLYCOALKALOID METABOLISM 1 (GAME1) glycosyltransferase, a homolog of the potato SGT1 (McCue et al., 2005, supra), catalyzes galactosylation of the alkamine tomatidine (Itkin et al., 2011, supra). SGA biosynthesis depends both on SGA biosynthesis genes (e.g., GAME 4, GAME12) and on regulators of SGA biosynthesis (e.g., GAME9) (Itkin et al. 2013. Science 341: 175-179; Cardenas et al. 2016. Nat. Commun. 7: 10654).

Steroidal alkaloids play a role in protecting plants against a broad range of pathogens and are thus referred to as phytoanticipins (antimicrobial compounds). Many SGAs are harmful to a variety of organisms including mammals and humans. When present in edible plant parts, these harmful SGAs are referred to as antinutritional substances. The SGAs α-solanine and α-chaconine are the principle toxic substances in potato. These SGAs cause gastrointestinal and neurological disorders and, at high concentrations, may be lethal to humans. Mechanisms of toxicity include disruption of membranes and inhibition of acetylcholine esterase activity (Roddick J G. 1989. Phytochemistry 28:2631-2634). For this reason, total SGA levels exceeding 200 mg per kilogram fresh weight of edible tuber are deemed unsafe for human consumption.

There is an ongoing attempt to elucidate the biosynthesis pathway of steroidal alkaloids and to control their production. U.S. Pat. No. 5,959,180 discloses DNA sequences from potato which encode the enzyme solanidine UDP-glucose glucosyltransferase (SGT). Further disclosed are means and methods for inhibiting the production of SGT and thereby reduce glycoalkaloid levels in Solanaceous plants, for example potato.

Similarly, U.S. Pat. Nos. 7,375,259 and 7,439,419 disclose nucleic acid sequences from potato that encode the enzymes UDP-glucose:solanidine glucosyltransferase (SGT2) and (β-solanine/β-chaconine rhamnosyltransferase (SGT3), respectively. Recombinant DNA molecules containing the sequences, and use thereof, in particular, use of the sequences and antisense constructs to inhibit the production of SGT2/SGT3 and thereby reduce levels of the predominant steroidal glycoalkaloids α-chaconine and α-solanine in Solanaceous plants such as potato are also described.

The inventors of the present invention have recently identified three glycosyltransferases that are putatively involved in the metabolism of tomato steroidal alkaloids (GLYCOALKALOID METABOLISM 1-3 (GAME1-3). More specifically, alterations in GAME1 expression modified the SA profile in tomato plants in both reproductive and vegetative parts. It is suggested that these genes are involved in the metabolism of tomatidine (the α-tomatine precursor) partially by generating the lycotetraose moiety (Itkin et al., 2011, supra).

International Patent Application Publication No. WO 00/66716 discloses a method for producing transgenic organisms or cells comprising DNA sequences which code for sterol glycosyl-transferases. The transgenic organisms include bacteria, fungi, plants and animals, which exhibit an increased production of steroid glycoside, steroid alkaloid and/or sterol glycoside compared to that of wild-type organisms or cells. The synthesized compounds are useful in the pharmaceutical and foodstuff industries as well as for protecting plants.

U.S. Patent Application Publication No. 2012/0159676 discloses a gene encoding a glycoalkaloid biosynthesis enzyme derived from a plant belonging to the family Solanaceae for example potato (*Solanum tuberosum*). A method for producing/detecting a novel organism using a gene encoding the protein is also disclosed.

U.S. Patent Application Publication No. 2013/0167271 and International Application Publication No. WO 2012/095843 relate to a key gene in the biosynthesis of steroidal saponins and steroidal alkaloids and to means and methods for altering the gene expression and the production of steroidal saponins and steroidal alkaloids.

A paper of the inventors of the present invention, published after the priority date of the present invention, describes an array of 10 genes that partake in SGA biosynthesis. 5-7 of the genes were found to exist as a cluster on chromosome 7 while additional two reside adjacent in a duplicated genomic region on chromosome twelve. Following systematic functional analysis, a novel SGA biosynthetic pathway starting from cholesterol up to the tetrasaccharide moiety linked to the tomato SGA aglycone has been proposed (Itkin M. et al., 2013 Science 341(6142):175-179).

It has also been found that the plant cholesterol biosynthetic pathway overlaps with phytosterol metabolism (Sonawane et al. 2016. Nat. Plants 3: 16205). For example, cholesterol ((3β)-cholest-5-en-3-ol) is a sterol (or modified steroid), https://en.wikipedia.org/wiki/Cholesterol-cite note-4 a type of lipid molecule, and is biosynthesized by all animal cells, because it is an essential structural component of all animal cell membranes and is essential to maintain both membrane structural integrity and fluidity. It is often found in animal cell membranes, enabling animal cells to function without a cell wall. It is a precursor for the biosynthesis of steroid hormones, bile acid and vitamin D.

Cholestanol is a cholesterol derivative found in feces, gallstones, eggs, and other biological matter. 5β-Coprostanol (5β-cholestan-3β-ol) is a 27-carbon stanol formed from the biohydrogenation of cholesterol (cholest-5en-3β-ol) in the gut of most higher animals (e.g., birds; humans and other mammals). It is formed by the conversion of cholesterol to coprostanol (cholestanol) in the gut of most higher animals by intestinal bacteria.

Plants make cholesterol in very small amounts, but also manufacture phytosterols (which include plant sterols and stanols, similar to cholesterol and cholestanol), which can compete with cholesterol for reabsorption in the intestinal tract, thus potentially reducing cholesterol reabsorption. Cholesterol is often used in the manufacture of medicines, cosmetics, and other applications. There is an increased interest in producing increased levels of both plant phytosterols and plant-based cholesterol.

In tomato (e.g., *Solanum lycopersicum, Solanum pennellii*), α-tomatine and dehydrotomatine represent the major SGAs accumulating predominantly in green tissues; young and mature leaves, flower buds, skin and seeds of immature and mature green fruit. Dehydrotomatidine (i.e. tomatidenol) is the first SA aglycone formed in SGA biosynthesis which could further be hydrogenated at the C-5 position to form tomatidine. Both aglycones are further glycosylated (tetra-saccharide moiety i.e. lycotetrose) to produce dehydrotomatine and α-tomatine, respectively. Thus, the SGA pathway branches at dehydrotomatidine for either formation of tomatidine derived SGAs or glycosylated dehydrotomatine derivatives. Notably, dehydrotomatidine and tomatidine are only different in their structures by the presence or absence of the double bond at the C-5 position. The conversion of dehydrotomatidine to tomatidine was hypothesized in the past as a single reaction catalyzed by a hypothetical hydrogenase. In most tomato plant tissues, the relative portion of dehydrotomatine as compared to α-tomatine ranges from ~2.5-~10%. As tomato fruit matures and reaches to the red stage, the entire pool of α-tomatine and dehydrotomatine is largely being converted to esculeosides (major SGAs) and dehydroesculeosides (minor SGAs), respectively.

In cultivated potato, α-chaconine and α-solanine are the major SGAs sharing the same aglycone, solanidine (in which a C-5,6 double bond is present) and possess chacotriose and solatriose moieties, respectively. As there is no demissidine or demissine detected in cultivated potatoes, it was suggested that a hydrogenase enzyme able to convert solanidine to demissidine is lacking in these species. Several wild potato species (e.g. *S. demissum, S. chacoense, S. commersonii*) and their somatic hybrids (*S. brevidens×S. tuberosum*), predicted to contain an active hydrogenase, do produce demissidine or its glycosylated form, demissine being one of their major SGAs.

In eggplant, α-solamargine and α-solasonine are the most abundant SGAs derived from the solasodine aglycone (in which a C-5,6 double bond is present); while some wild *solanum* species, e.g. S. dulcamara produce soladulcidine or its glycosylated forms, soladulcine A and β-soladulcine (C-5,6 double bond is absent), as major SGAs from the solasodine aglycone.

In addition to SGAs, many *Solanum* species (e.g. eggplant) also produce cholesterol-derived unsaturated or saturated steroidal saponins. Unsaturated and saturated steroidal saponins are widespread in the plant kingdom, especially among monocots, e.g. the *Agavaceae* (e.g., agave and yucca), Asparagaceae (e.g., asparagus), Dioscoreaceae and Liliaceae families. Similar to SGAs, steroidal saponins are highly diverse in structures and could be either saturated (e.g. sarasapogenin) or unsaturated (e.g. diosgenin) in the C-5,6 position.

Cholesterol, the main sterol produced by all animals, serves as a key building block in the biosynthesis of SGAs. An array of tomato and potato GLYCOALKALOIDMETABOLISM (GAME) genes participating in core SGA biosynthesis starting from cholesterol were reported in recent years. The tomato SGAs biosynthetic pathway can be divided into two main parts. In the first, the SA aglycone is formed from cholesterol by the likely action of the GAME6, GAME8, GAME11, GAME4 and GAME12 enzymes. The second part results in the generation of SGA through the action of UDP-glycosyltransferases (UGTs): GAME1, GAME2, GAME17 and GAME18 in tomato, and STEROL ALKALOID GLYCOSYL TRANSFERASE1 (SGT1), SGT2 and SGT3 in potato.

The demand for higher food quantities and food with improved quality continues to increase. Improved nutritional qualities as well as removal of antinutritional traits are both of high demand. In the course of crop domestication, levels of anti-nutrients were reduced by breeding, However, Solanaceous crop plants still contain significant amount of antinutritional substances, particularly steroidal glycoalkaloids.

Alternatively, the ability to manipulate the synthesis of these SGAs would provide the means to develop, through classical breeding or genetic engineering, crops with modified levels and composition of SGAs, conferring on the plant an endogenous chemical barrier against a broad range of insects and other pathogens.

In addition, there is a demand both for plant-based cholesterols and, conversely, for plants with increased levels of phytocholesterols or other phytosterols.

Thus, there is a demand for, and would be highly advantageous to have means and method for controlling the production of steroidal alkaloids in Solanaceous plants for obtaining high quality non-toxic food products as well as for the production of steroidal alkaloids and phytosterols with beneficial, particularly therapeutic, effects.

SUMMARY OF DISCLOSURE

The present invention relates to key genes and enzymes in the biosynthesis pathway converting cholesterol to steroidal glycoalkaloids (SGA), useful for modulating the expression of steroidal alkaloids and in plants. Particularly, the present invention relates to transgenic Solanaceous plants with reduced content of antinutritional alkaloids.

The present invention is based in part on the unexpected discovery that the biosynthesis of SGAs in Solanaceous plant involves an array of genes, wherein 5-7 of the genes (depending on the plant species) are clustered on chromosome 7 and additional two genes are placed adjacent in a duplicated genomic region on chromosome 12. Several regulatory genes, including transcription factors were found to be co-expressed with the clustered genes. Modulating the expression of particular genes within the array enabled strict control of the production of steroidal alkaloids and glycosylated derivatives thereof. Unexpectedly, modulating the expression of a single gene or transcription factor resulted in significant elevation/reduction in the content of steroidal alkaloids (e.g., solanine and/or chaconine in potato), in tomato, potato and eggplant plants, of α-tomatine in tomato plants, of cholesterol in tomato plants. Particularly, the present invention now shows that modulating a single transcription factor, designated herein GAME9-transcription factor resulted in strict control on the production of steroidal glycoalkaloids (SGAs) in potato tuber peels. Particularly, the present invention now shows that modulating a single protein, designated herein GAME15 (the product of a cellulose synthase like gene), resulted in strict control on the production of steroidal glycoalkaloids (SGAs) and steroidal saponins in tomatoes, potatoes, and eggplants. Inhibiting the expression of a gene encoding 2-oxoglutarate-dependent dioxygenase (GAME11) resulted in a significant reduction in α-tomatine level and accumulation of several phytosterols, including cholesterol, cholestanol, and any of their modified glycosylated derivatives, steroidal saponins in tomato plants. Inhibiting the expression of a gene encoding cellulose synthase like protein (GAME15) resulted in a significant reduction in levels of α-tomatine and downstream SGAs (including esculeosides) in tomato plants and an accumulation of cholesterol (a precursor for SGAs) in tomato plants. In potato, silencing of GAME15 resulted in significant reductions in α-chaconine and α-solanine and in accumulation of a cholesterol pool. According to one aspect, the present invention provides a genetically modified or gene edited plant comprising at least one cell having altered expression of at least one gene selected from the group consisting of a gene encoding a cellulose synthase like protein (GAME15), wherein the genetically modified or gene edited plant has an altered content of at least one steroidal alkaloid or a glycosylated derivative thereof compared to a corresponding unmodified or unedited plant.

According to one aspect, the present invention provides a genetically modified plant comprising at least one cell having altered expression of at least one gene selected from the group consisting of a gene encoding at least one cellulose synthase like protein compared to its expression in a corresponding unmodified plant, wherein the genetically modified plant has an altered content of at least one steroidal alkaloid or a glycosylated derivative thereof compared to the corresponding unmodified plant.

According to certain embodiments, expression of the gene encoding the at least one cellulose synthase like protein is reduced compared to its expression in the corresponding unmodified plant, thereby the genetically modified plant comprises reduced content at least one steroidal alkaloid or a glycosylated derivative thereof compared to the corresponding unmodified plant. According to other embodiments, expression of the gene encoding the at least one cellulose synthase like protein is elevated compared to its expression in the corresponding unmodified plant, thereby the genetically modified plant comprises elevated content at least one steroidal alkaloid or a glycosylated derivative thereof compared to the corresponding unmodified plant.

According to one aspect, the present invention provides method of reducing the content of at least one steroidal alkaloid or a glycosylated derivative thereof in a modified plant, the method comprising (a) transforming at least one plant cell with at least one silencing molecule targeted to a nucleic acid sequence encoding at least one protein comprising a cellulose synthase like protein; or (b) mutagenizing at least one gene or a combination of genes, the genes encoding at least one protein selected from the group consisting of cellulose synthase like proteins, wherein the mutagenesis comprises introduction of one or more point mutations into the gene, or genome editing, or use of a bacterial CRISPR/CAS system, or a combination thereof, wherein expression of the gene encoding the at least one cellulose synthase like protein is reduced in the modified plant compared to its expression in a corresponding unmodified plant, thereby the modified plant comprises reduced content at least one steroidal alkaloid or a glycosylated derivative thereof compared to the corresponding unmodified plant.

According to one aspect, the present invention provides a method of producing at least one phytosterol in a modified plant, the method comprising (a) transforming at least one plant cell with at least one silencing molecule targeted to a nucleic acid sequence encoding at least one protein comprising a cellulose synthase like factor; or (b) mutagenizing at least one gene or a combination of genes, the genes encoding at least one protein selected from the group consisting of cellulose synthase like factors, wherein the mutagenesis comprises introduction of one or more point mutations into the gene, or genome editing, or use of a bacterial CRISPR/CAS system, or a combination thereof, wherein expression of the gene encoding the at least one cellulose synthase like protein is reduced in the modified plant compared to its expression in a corresponding unmodified plant, thereby the modified plant comprises reduced content at least one steroidal alkaloid or a glycosylated derivative thereof compared to the corresponding unmodified plant.

According to certain embodiments, the plant is a transgenic plant comprising at least one cell comprising at least one transcribable polynucleotide encoding at least one protein comprising a cellulose synthase like protein. According to certain embodiments, the transcribable polynucleotide comprises the nucleic acid sequence set forth in any one of SEQ ID NOS: 32, 34, 36, 38, 40, or 42.

Other objects, features and advantages of the present invention will become clear from the following description and drawings.

BRIEF DESCRIPTION OF THE FIGURES

FIG. 2 summarizes the coexpression analysis of steroidal alkaloid-associated genes in Solanaceous plants. Shared homologs of coexpressed genes for 'baits' from tomato (SlGAME1 and SlGAME4) and potato (StSGT1 and StGAME4). Continuous (r-value >0.8) and dashed (r-value >0.63) lines connect coexpressed genes. *, located in the tomato or potato chromosome 7 cluster. St, $Solanum$ $tuberosum$; Sl, $S.$ $lycopersicum$. Background of gene names corresponds to bait they were found to be coexpressed with (legend above). SP, serine proteinase; PI, proteinase inhibitor; UPL, ubiquitin protein ligase; ELP, extensin-like protein; PK, protein kinase; SR, sterol reductase; RL, receptor-like.

(FIG. 4A) GAME8-silenced transgenic (RNAi) leaves accumulated 22-(R)-hydroxycholesterol compared to wild type. (FIG. 4B) An array of cholestanol-type steroidal saponins (STSs) accumulates in GAME11 VIGS-silenced leaves. (FIG. 4C) An STS (m/z=753.4) accumulates in GAME12 VIGS-leaves. (FIG. 4D) Tomatidine, the steroidal alkaloid aglycone, accumulates in GAME1-silenced transgenic leaves. (FIGS. 4E to 4H) Enzyme activity assays of the 4 recombinant tomato GAME glycosyltransferases.

FIGS. 8A-8D show the effect of silencing of GAME 11 dioxygenase in tomato. (FIG. 8A) α-tomatine levels in leaves (m/z=1034.5) (FIG. 8B) cholestanol-type steroidal saponins (STS) in leaves (m/z=1331.6, 1333.6, 1199.6, 1201.6 (major saponins)). (FIG. 8C) MS/MS spectrum of m/z=1331.6 (at 19.28 min.). (FIG. 8D) The fragmentation patterns of the saponin eluted at 19.28 min. and accumulating in GAME11-silenced leaves. Corresponding mass signals are marked with an asterisk on the MS/MS chromatogram in FIG. 8C.

(FIG. 10A) accumulation of a furastanol-type STS. (FIGS. 10B-10C) GAME/2-silenced leaves accumulate an STS (m/z=753.4), while it exists in only minor quantities in WT leaf. (FIG. 10D) MS/MS spectrum of m/z=753.4 at 19.71 min. with interpretation of the fragments.

(FIG. 11D) GAME8-silenced line accumulates both isomers in comparison to WT (Q).

DETAILED DESCRIPTION

Figure 1:
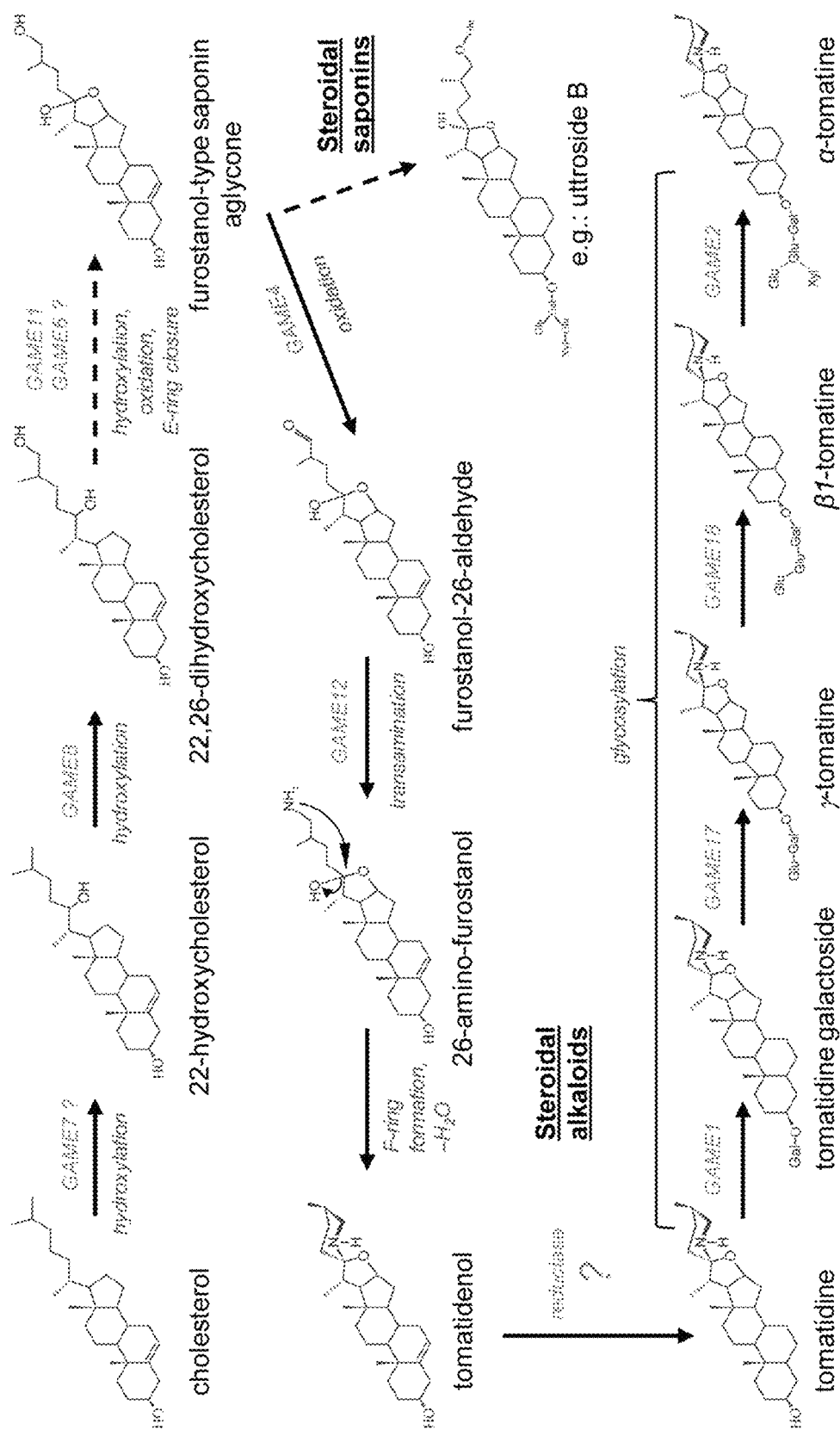
FIG. 1 shows the proposed biosynthetic pathway of steroidal glycoalkaloids in the triterpenoid biosynthetic pathway in Solanaceous plant from cholesterol toward α-tomatine. Dashed and solid arrows represent multiple or single enzymatic reactions in the pathway, respectively.

According to one aspect, the present invention provides a genetically modified plant comprising at least one cell having altered expression of at least one gene selected from the group consisting of a gene encoding at least one cellulose synthase like protein compared to its expression in a corresponding unmodified plant, wherein the genetically modified plant has an altered content of at least one steroidal alkaloid or a glycosylated derivative thereof compared to the corresponding unmodified plant.

According to certain embodiments, the cellulose synthase like protein is a GAME15 protein. According to certain embodiments, the amino acid sequence of the cellulose synthase like protein of the corresponding unmodified plant comprises the sequence set for cellulose synthase like protein is at least 80% homologous to the amino acid sequence set forth in any one of SEQ ID NOS: 33, 35, 37, 39, 42, or 43. According to certain embodiments, the polynucleotide encoding the cellulose synthase like protein of the corresponding unmodified plant comprises the nucleic acid sequence set forth in any one of SEQ ID NOS: 32, 34, 36, 38, 40, or 42.

According to certain embodiments, expression of the at least one gene or any combination thereof is altered, the altering comprising mutagenizing the at least one gene, wherein the mutagenesis comprises introduction of one or more point mutations, or genome editing, or use of a bacterial CRISPR/CAS system, or a combination thereof.

According to certain embodiments, expression of the gene encoding the at least one cellulose synthase like protein is reduced compared to its expression in the corresponding unmodified plant, thereby the genetically modified plant comprises reduced content at least one steroidal alkaloid or a glycosylated derivative thereof compared to the corresponding unmodified plant.

According to certain embodiments, the genetically modified plant is a transgenic plant comprising at least one cell comprising at least one silencing molecule targeted to a polynucleotide encoding at least one cellulose synthase like protein. According to certain embodiments, the transgenic plant comprises a polynucleotide encoding a cellulose synthase like protein, wherein expression of the polynucleotide is selectively silenced, repressed, or reduced. According to certain embodiments, the transgenic plant comprises a polynucleotide encoding a cellulose synthase like protein, wherein the polynucleotide has been selectively edited by deletion, insertion, or modification to silence, repress, or reduce expression thereof, or wherein the genetically modified plant is a progeny of the gene edited plant.

According to certain embodiments, the transgenic plant comprises at least one cell comprising at least one silencing molecule targeted to a GAME15 gene.

According to certain embodiments, the transgenic plant comprises at least one cell comprising at least one silencing molecule targeted to the nucleic acid sequence set forth in any one of SEQ ID NOS: 32, 34, 36, 38, 40, or 42. According to certain embodiments, the silencing molecule is selected from the group consisting of an RNA interference molecule and an antisense molecule, or wherein the silencing molecule is a component of a viral induced gene silencing system. According to certain embodiments, the silencing molecule comprises a polynucleotide having a nucleic acid sequence substantially complementary to a region of the GAME15 gene having the nucleic acid sequence set forth in any one SEQ ID NOS: 32, 34, 36, 38, 40, or 42 or a complementary sequence thereof. According to certain embodiments, the silencing molecule is targeted to a GAME15 fragment having the nucleic acid sequence set forth in SEQ ID NO: 44 or a complementary sequence thereof. According to certain embodiments, the silencing molecule is targeted to a GAME15 fragment having the nucleic acid sequence set forth in SEQ ID NO: 45 or a complementary sequence thereof. According to certain embodiments, the silencing molecule is targeted to a GAME15 fragment having the nucleic acid sequence set forth in SEQ ID NO: 46 or a complementary sequence thereof.

According to certain embodiments, the genetically modified plant is a Solanaceae plant having a reduced content of at least one steroidal glycoalkaloid selected from the group consisting of α-tomatine, tomatidine, α-chaconine, α-solanine, α-solasonine, α-solmargine, and derivatives thereof, compared to a corresponding unmodified plant. According to certain embodiments, the genetically modified plant further comprises an elevated content of a phytosterol or a derivative thereof, a cholesterol or a derivative thereof, a phytocholesterol or a derivative thereof, a cholestenol or a derivative thereof, a phytocholestanol or a derivative thereof, or a steroidal saponin or a derivative thereof compared to a corresponding unmodified plant.

According to certain embodiments, the plant is a Solanaceae plant selected from the group consisting of tomato, potato, eggplant, and pepper. According to certain embodiments, the plant is a tomato plant comprising a reduced content of α-tomatine, tomatidine, or derivatives thereof. According to certain embodiments, the plant is a tomato plant comprising an elevated content of a phytosterol, a phytocholesterol or cholesterol, a phytocholestenol or cholestenol, a steroidal saponin, or derivative thereof. According to certain embodiments, the plant is a potato plant comprising a reduced content of α-chaconine, α-solanine, or derivatives thereof. According to certain embodiments, the plant is an eggplant plant comprising a reduced content of α-solasonine, α-solamargine, or derivatives thereof.

According to other certain embodiments, expression of the gene encoding the at least one cellulose synthase like protein is elevated compared to its expression in the corresponding unmodified plant, thereby the genetically modified plant comprises elevated content at least one steroidal alkaloid or a glycosylated derivative thereof compared to the corresponding unmodified plant. According to certain embodiments, the transgenic plant comprises a polynucleotide encoding a cellulose synthase like protein, wherein expression of the polynucleotide is selectively increased. According to certain embodiments, the transgenic plant comprising at least one cell comprising at least one transcribable polynucleotide encoding at least one protein selected from the group consisting of at least one a cellulose synthase like protein. According to certain embodiments, the cellulose synthase like protein is a GAME15 protein. According to certain embodiments, the transcribable polynucleotide comprises the nucleic acid sequence set forth in any one of SEQ ID NOS: 32, 34, 36, 38, 40, or 42. According to certain embodiments, the genetically modified plant is a Solanaceae plant having an elevated content of at least one steroidal glycoalkaloid selected from the group consisting of α-tomatine, tomatidine, α-chaconine, α-solanine, α-solasonine, α-solmargine, and derivatives thereof, compared to a corresponding unmodified plant. According to certain embodiments, the genetically modified plant further comprises a reduced content of a phytosterol or a derivative thereof, a cholesterol or a derivative thereof, a phytocholesterol or a derivative thereof, a cholestenol or a derivative thereof, a phytocholestanol or a derivative thereof, or a steroidal saponin or a derivative thereof compared to a corresponding unmodified plant. According to certain embodiments, the plant is a Solanaceae plant selected from the group consisting of tomato, potato, eggplant, and pepper.

According to one aspect, the present invention provides a method of reducing the content of at least one steroidal alkaloid or a glycosylated derivative thereof in a modified plant, the method comprising (a) transforming at least one plant cell with at least one silencing molecule targeted to a nucleic acid sequence encoding at least one protein comprising a cellulose synthase like protein; or (b) mutagenizing at least one gene or a combination of genes, the genes encoding at least one protein selected from the group consisting of cellulose synthase like proteins, wherein the mutagenesis comprises introduction of one or more point mutations into the gene, or genome editing, or use of a bacterial CRISPR/CAS system, or a combination thereof, wherein expression of the gene encoding the at least one cellulose synthase like protein is reduced in the modified plant compared to its expression in a corresponding unmodified plant, thereby the modified plant comprises reduced content at least one steroidal alkaloid or a glycosylated derivative thereof compared to the corresponding unmodified plant.

According to certain embodiments, the cellulose synthase like protein is a GAME15 protein. According to certain embodiments, the amino acid sequence of the cellulose synthase like protein of the corresponding unmodified plant comprises the sequence set for cellulose synthase like protein is at least 80% homologous to the amino acid sequence set forth in any one of SEQ ID NOS: 33, 35, 37, 39, 42, or 43. According to certain embodiments, wherein the polynucleotide encoding the cellulose synthase like protein of the corresponding unmodified plant comprises the nucleic acid sequence set forth in any one of SEQ ID NOS: 32, 34, 36, 38, 40, or 42.

According to certain embodiments, the silencing molecule is targeted to a GAME15 fragment having the nucleic acid sequence set forth in SEQ ID NO: 44 or a complementary sequence thereof. According to certain embodiments, the silencing molecule is targeted to a GAME15 fragment having the nucleic acid sequence set forth in SEQ ID NO: 45 or a complementary sequence thereof. According to certain embodiments, the silencing molecule is targeted to a GAME15 fragment having the nucleic acid sequence set forth in SEQ ID NO: 46 or a complementary sequence thereof.

According to certain embodiments, the modified plant is a Solanaceae plant having a reduced content of at least one steroidal glycoalkaloid selected from the group consisting of α-tomatine, tomatidine, α-chaconine, α-solanine, α-solasonine, α-solmargine, and derivatives thereof, compared to the corresponding unmodified plant.

According to certain embodiments, the modified plant further comprises an elevated content of a phytosterol or a derivative thereof, a cholesterol or a derivative thereof, a phytocholesterol or a derivative thereof, a cholestenol or a derivative thereof, a phytocholestanol or a derivative thereof, or a steroidal saponin or a derivative thereof compared to a corresponding unmodified plant.

According to certain embodiments, the modified plant is a Solanaceae plant selected from the group consisting of tomato, potato, eggplant, and pepper. According to certain embodiments, the plant is a tomato plant comprising a reduced content of α-tomatine, tomatidine, or derivatives thereof. According to certain embodiments, the plant is a tomato plant comprising an elevated content of a phytosterol, a phytocholesterol or cholesterol, a phytocholestenol or cholestenol, a steroidal saponin, or derivative thereof. According to certain embodiments, the plant is a potato plant comprising a reduced content of α-chaconine, α-solanine, or derivatives thereof. According to certain embodiments, the plant is an eggplant plant comprising a reduced content of α-solasonine, α-solamargine, or derivatives thereof.

According to one aspect, the present invention provides a method of producing at least one phytosterol in a modified plant, the method comprising (a) transforming at least one plant cell with at least one silencing molecule targeted to a nucleic acid sequence encoding at least one protein comprising a cellulose synthase like factor; or (b) mutagenizing at least one gene or a combination of genes, the genes encoding at least one protein selected from the group consisting of cellulose synthase like factors, wherein the mutagenesis comprises introduction of one or more point mutations into the gene, or genome editing, or use of a bacterial CRISPR/CAS system, or a combination thereof, wherein expression of the gene encoding the at least one cellulose synthase like protein is reduced in the modified plant compared to its expression in a corresponding unmodified plant, thereby the modified plant comprises reduced content at least one steroidal alkaloid or a glycosylated derivative thereof compared to the corresponding unmodified plant.

According to certain embodiments, the cellulose synthase like protein is a GAME15 protein. According to certain embodiments, the amino acid sequence of the cellulose synthase like protein of a corresponding unmodified plant comprises the sequence set for cellulose synthase like protein is at least 80% homologous to the amino acid sequence set forth in any one of SEQ ID NOS: 33, 35, 37, 39, 42, or 43. According to certain embodiments, the polynucleotide encoding the cellulose synthase like protein of a corresponding unmodified plant comprises the nucleic acid sequence set forth in any one of SEQ ID NOS: 32, 34, 36, 38, 40, or 42.

According to certain embodiments, the method further comprises purifying the phytosterol extracted from the transformed plant. According to certain embodiments, the phytosterol comprises phytocholesterol.

According to certain embodiments, the silencing molecule is targeted to a GAME15 fragment having the nucleic acid sequence set forth in SEQ ID NO: 44 or a complementary sequence thereof. According to certain embodiments, the silencing molecule is targeted to a GAME15 fragment having the nucleic acid sequence set forth in SEQ ID NO: 45 or a complementary sequence thereof. According to certain embodiments, the silencing molecule is targeted to a GAME15 fragment having the nucleic acid sequence set forth in SEQ ID NO: 46 or a complementary sequence thereof.

According to certain embodiments, the modified plant further comprises an elevated content of a phytosterol or a derivative thereof, a cholesterol or a derivative thereof, a phytocholesterol or a derivative thereof, a cholestenol or a derivative thereof, a phytocholestanol or a derivative thereof, or a steroidal saponin or a derivative thereof compared to a corresponding unmodified plant.

According to certain embodiments, the modified plant is a Solanaceae plant. According to certain embodiments, the Solanaceae plant is selected from the group consisting of tomato, potato, eggplant, and pepper.

It is to be understood that inhibiting the expression of the at least one gene or combination thereof may be achieved by various means, all of which are explicitly encompassed within the scope of present invention. According to certain embodiments, inhibiting the expression of GAME15 can be affected at the genomic and/or the transcript level using a variety of molecules that interfere with transcription and/or translation including, but not limited to, antisense, siRNA, Ribozyme, or DNAzyme molecules. Inserting a mutation to the at least one gene, including deletions, insertions, site specific mutations, zinc-finger nucleases and the like can be also used, as long as the mutation results in down-regulation of the gene expression. According to other embodiments, expression is inhibited at the protein level using antagonists, enzymes that cleave the polypeptide and the like.

According to certain exemplary embodiments, the genetically modified or gene edited plant is a transgenic plant comprising at least one cell comprising at least one silencing molecule targeted to a GAME15 gene. Each possibility represents a separate embodiment of the present invention. According to some embodiments, the at least one silencing molecule is selected from the group consisting of RNA interference molecule and antisense molecule. According to these embodiments, the transgenic plant comprises reduced content of at least one steroidal alkaloid or glycosylated derivative thereof, or of at least one steroidal saponin or glycosylated derivative thereof, compared to non-transgenic plant. According to certain embodiments, the at least one steroidal alkaloid is steroidal glycoalkaloid. According to certain exemplary embodiments, the steroidal glycoalkaloid is selected from the group consisting of α-solanine, α-chaconine, α-solmargine, α-solasonine, α-tomatine, tomatidine and derivatives thereof. According to certain embodiments, the transgenic plant comprises reduced content of at least one downstream steroidal alkaloid or glycosylated derivative thereof compared to non-transgenic plant. According to certain exemplary embodiments, the downstream steroidal glycoalkaloid is selected from the group consisting of esculeosides. According to certain embodiments, the transgenic plant comprises increased content of at least one phytosterol. In some embodiments, the phytosterol is a phytocholesterol, a cholesterol, or a cholestanol. According to some embodiments, the transgenic plant comprises a plurality of cells comprising the silencing molecule targeted to at least one GAME15 gene. According to additional embodiments, the majority of the plant cells comprise the silencing molecule.

The silencing molecule target to at least one GAME15 can be designed as is known to a person skilled in the art. According to certain embodiments, the silencing molecule comprises a polynucleotide having a nucleic acid sequence substantially complementary to a region of the GAME15, gene or to a complementary sequence of GAME15, e.g., having the nucleic acids sequence set forth in any one of SEQ ID NOS: 44 to 46. Each possibility represents a separate embodiment of the present invention.

According to certain exemplary embodiments, the silencing molecule is targeted to a GAME15 fragment having the nucleic acids sequence set forth in SEQ ID NOS: 44 to 46 or a complementary sequence thereof.

According to certain additional embodiments, the silencing molecule comprises a polynucleotide having a nucleic acid sequence substantially complementary to a region of the GAME15 gene or a complementary sequence thereof, having the nucleic acids sequence set forth in any one of SEQ ID NOS: 44 to 46. Each possibility represents a separate embodiment of the present invention.

According to certain embodiments, the silencing molecule is an antisense RNA.

According to certain exemplary embodiments, the silencing molecule is an RNA interference (RNAi) molecule. According to some embodiments, the silencing molecule is a double-stranded (ds)RNA molecule. According to certain embodiments, the first and the second polynucleotides are separated by a spacer. According to exemplary embodiments, the spacer sequence is an intron. According to yet further embodiments, the expression of the first and the second polynucleotides is derived from one promoter. According to other embodiments, expression of the first and the second polynucleotides are derived from two promoters; the promoters can be identical or different. Each possibility represents a separate embodiment of the present invention.

According certain exemplary embodiments, the dsRNA is targeted to GAME15, said dsRNA molecule comprises a first polynucleotide and a second polynucleotide having a nucleic acid sequence complementary to said first polynucleotide.

According to certain embodiments, the transgenic tomato plant further comprises elevated amounts of steroidal saponins. According to certain embodiments, the steroidal saponin is a cholesterol-derived saponin. Each possibility represents a separate embodiment of the present invention.

Overexpression of the at least one gene can be obtained by any method as is known to a person skilled in the art. According to certain embodiments, the present invention provides a transgenic plant comprising at least one cell comprising at least one transcribable polynucleotide encoding at least one GAME15 protein, wherein the transgenic plant comprises elevated content of at least one steroidal alkaloid or a glycosylated derivative thereof compared to a corresponding non-transgenic plant or reduced content of at least one phytosterol.

According to some embodiments, the polynucleotides of the present invention are incorporated in a DNA construct enabling their expression in the plant cell. DNA constructs suitable for use in plants are known to a person skilled in the art. According to one embodiment, the DNA construct comprises at least one expression regulating element selected from the group consisting of a promoter, an enhancer, an origin of replication, a transcription termination sequence, a polyadenylation signal and the like.

The DNA constructs of the present invention are designed according to the results to be achieved. In crop plants, reduction of toxic steroidal glycoalkaloids is desired in the edible parts of the plant, including, for example, fruit and tubers. On the other hand, enriching the content of toxic steroidal glycoalkaloids in non-edible roots and leaves contributes to the resistance of the plant against a broad range of pathogens. Plants overexpressing the steroidal glycoalkaloids can be used for producing them for the pharmaceutical industry.

According to certain embodiments, the DNA construct comprises a promoter. The promoter can be constitutive, induced or tissue specific as is known in the art. Optionally, the DNA construct further comprises a selectable marker, enabling the convenient selection of the transformed cell/tissue. Additionally, or alternatively, a reporter gene can be incorporated into the construct, so as to enable selection of transformed cells or tissue expressing the reporter gene.

Suspensions of genetically modified or gene edited cells and tissue cultures derived from the genetically modified or gene edited cells are also encompassed within the scope of the present invention. The cell suspension and tissue cultures can be used for the production of desired steroidal glycoalkaloids and, which are then extracted from the cells or the growth medium. Alternatively, the genetically modified or gene edited cells and/or tissue culture are used for regenerating a transgenic plant having modified or gene edited expression of GAME15, therefore having modified content of steroidal glycoalkaloids.

The present invention further encompasses seeds of the genetically modified or gene edited plant, wherein plants grown from said seeds have altered expression of GAME15 compared to plants grown from corresponding unmodified or unedited seeds, thereby having an altered content of at least one steroidal glycoalkaloid.

Genetically Modified Plants & Gene Edited Plants

Disclosed herein are genetically modified plants and gene edited plants, wherein expression of key genes in the steroidal glycoalkaloids metabolic pathway (biosynthesis pathway of steroidal alkaloids and glycosylated derivatives thereof) have been altered. Altering the expression of these genes results in concomitant alteration in the steroidal alkaloid profile. Changing the production level of steroidal alkaloid can result in improved plants comprising elevated content of steroidal alkaloids having increased resistance to pathogens, or plants having a reduced content of these secondary compounds in the plant edible parts and thus producing improved crops, wherein the improved crop has reduced or eliminated anti-nutritional content. Alternatively, or additionally, controlling the expression of genes disclosed herein may be used for the production of desired steroidal alkaloids or plant-based cholesterol for further use, for example in the pharmaceutical industry. In particular, disclosed herein are the means and methods for producing crop plants of the Solanaceae family that are devoid of toxic amounts of deleterious steroidal alkaloids typically present in edible parts of these plants. The plants disclosed herein are thus of significant nutritional and commercial value.

Disclosed herein are an array of co-expressed genes that participate in the biosynthesis pathway of steroidal alkaloids. The present invention further discloses key genes in this pathway, altering the expression of which result in concomitant alteration in the steroidal alkaloid profile. Changing the production level of steroidal alkaloid can result in an improved plant comprising elevated content of steroidal alkaloids having increased resistance to pathogens, or plants having a reduced content of these secondary compounds in the plant edible parts and thus producing improved crops. Alternatively, or additionally, controlling the expression of genes revealed in the present invention can be used for the production of desired steroidal alkaloids or plant-based cholesterol for further use, for example in the pharmaceutical industry. In particular, the present invention discloses means and methods for producing crop plants of the genus *Solanum* that are devoid of toxic amounts of deleterious steroidal alkaloids typically present in edible parts of these plants. The plants of the present invention are thus of significant nutritional and commercial value.

Definitions

As used herein, the term "Solanaceous" refers to a plant of the genus *Solanum*.

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The term "gene" optionally also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

One of ordinary skill in the art would appreciate that the term "gene" may encompass a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The skilled artisan would appreciate that the term "gene" optionally also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

In one embodiment, a gene comprises DNA sequence comprising upstream and downstream regions, as well as the coding region, which comprises exons and any intervening introns of the gene. In some embodiments, upstream and downstream regions comprise non-coding regulatory regions. In some embodiments, upstream and downstream regions comprise regulatory sequences, for example but not limited to promoters, enhancers, and silencers. Non-limiting examples of regulatory sequences include, but are not limited to, AGGA box, TATA box, Inr, DPE, ZmUbi1, PvUbi1, PvUbi2, CaMV, 35S, OsAct1, zE19, E8, TA29, A9, pDJ3S, B33, PAT1, alcA, G-box, ABRE, DRE, and PCNA. Regulatory regions, may in some embodiments, increase or decrease the expression of specific genes within a plant described herein.

In another embodiment, a gene comprises the coding regions of the gene, which comprises exons and any intervening introns of the gene. In another embodiment, a gene comprises its regulatory sequences. In another embodiment, a gene comprises the gene promoter. In another embodiment, a gene comprises its enhancer regions. In another embodiment, a gene comprises 5' non-coding sequences. In another embodiment, a gene comprises 3' non-coding sequences.

In one embodiment, the skilled artisan would appreciate that DNA comprises a gene, which may include upstream and downstream sequences, as well as the coding region of the gene. In another embodiment, DNA comprises a cDNA (complementary DNA). One of ordinary skill in the art would appreciate that cDNA may encompass synthetic DNA reverse transcribed from RNA through the action of a reverse transcriptase. The cDNA may be single stranded or double stranded and can include strands that have either or both of a sequence that is substantially identical to a part of the RNA sequence or a complement to a part of the RNA sequence. Further, cDNA may include upstream and downstream regulatory sequences. In still another embodiment, DNA comprises CDS (complete coding sequence). One of ordinary skill in the art would appreciate that CDS may encompass a DNA sequence, which encodes a full-length protein or polypeptide. A CDS typically begins with a start codon ("ATG") and ends at (or one before) the first in-frame stop codon ("TAA", "TAG", or "TGA"). The skilled artisan would recognize that a cDNA, in one embodiment, comprises a CDS.

The terms "polynucleotide", "polynucleotide sequence", "nucleic acid sequence", and "isolated polynucleotide" are used interchangeably herein. These terms encompass nucleotide sequences and the like. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids.

The term "RNA interference" or "RNAi" refers to the silencing or decreasing of gene expression mediated by small double stranded RNAs. It is the process of sequence-specific, post-transcriptional gene silencing in animals and plants, initiated by inhibitory RNA (iRNA) that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

Typically, the term RNAi molecule refers to single- or double-stranded RNA molecules comprising both a sense and antisense sequence. For example, the RNA interference molecule can be a double-stranded polynucleotide molecule comprising self-complementary sense and antisense regions, wherein the antisense region comprises complementarity to a target nucleic acid molecule. Alternatively the RNAi molecule can be a single-stranded hairpin polynucleotide having self-complementary sense and antisense regions, wherein the antisense region comprises complementarity to a target nucleic acid molecule or it can be a circular single-stranded polynucleotide having two or more loop structures and a stem comprising self-complementary sense and antisense regions, wherein the antisense region comprises complementarity to a target nucleic acid molecule, and wherein the circular polynucleotide can be processed either in vivo or in vitro to generate an active molecule capable of mediating RNAi.

The terms "complementary" or "complement thereof" are used herein to refer to the sequences of polynucleotides which is capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind.

The term "construct" as used herein refers to an artificially assembled or isolated nucleic acid molecule which includes the polynucleotide of interest. In general, a construct may include the polynucleotide or polynucleotides of interest, a marker gene which in some cases can also be a gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation.

The terms "promoter element," "promoter," or "promoter sequence" as used herein, refer to a DNA sequence that is located at the 5' end (i.e. precedes) the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

As used herein, the term an "enhancer" refers to a DNA sequence which can stimulate promoter activity and may be an innate element of the promoter or a heterologous element inserted to enhance the level or tissue-specificity of a promoter.

The term "expression", as used herein, refers to the production of a functional end-product e.g., an mRNA or a protein.

The term "gene edited plant" refers to a plant comprising at least one cell comprising at least one gene edited by man. The gene editing includes deletion, insertion, silencing, or repression, such as of the "native genome" of the cell. Methods for creating a gene edited plant include techniques such as zinc-finger nucleases (ZFN), transcription activator-like effector nucleases (TALEN), and clustered regularly interspersed short palindromic repeats (CRISPR)/Cas systems.

The term "genetically modified plant" refers to a plant comprising at least one cell genetically modified by man. The genetic modification includes modification of an endogenous gene(s), for example by introducing mutation(s) deletions, insertions, transposable element(s) and the like into an endogenous polynucleotide or gene of interest. Additionally, or alternatively, the genetic modification includes transforming the plant cell with heterologous polynucleotide. A "genetically modified plant" and a "corresponding unmodified plant" as used herein refer to a plant comprising at least one genetically modified cell and to a plant of the same type lacking said modification, respectively.

One of ordinary skill in the art would appreciate that a genetically modified plant may encompass a plant comprising at least one cell genetically modified by man. In some embodiments, the genetic modification includes modification of an endogenous gene(s), for example by introducing mutation(s) deletions, insertions, transposable element(s) and the like into an endogenous polynucleotide or gene of interest. Additionally, or alternatively, in some embodiments, the genetic modification includes transforming at least one plant cell with a heterologous polynucleotide or multiple heterologous polynucleotides. The skilled artisan would appreciate that a genetically modified plant comprising transforming at least one plant cell with a heterologous polynucleotide or multiple heterologous polynucleotides may in certain embodiments be termed a "transgenic plant".

A skilled artisan would appreciate that a comparison of a "genetically modified plant" to a "corresponding unmodified plant" as used herein encompasses comparing a plant comprising at least one genetically modified cell and to a plant of the same type lacking the modification.

The skilled artisan would appreciate that the term "transgenic" when used in reference to a plant as disclosed herein encompasses a plant that contains at least one heterologous transcribable polynucleotide in one or more of its cells. The term "transgenic material" encompasses broadly a plant or a part thereof, including at least one cell, multiple cells or tissues that contain at least one heterologous polynucleotide in at least one of cell. Thus, comparison of a "transgenic plant" and a "corresponding non transgenic plant", or of a "genetically modified plant comprising at least one cell having altered expression, wherein said plant comprising at least one cell comprising a heterologous transcribable polynucleotide" and a "corresponding un modified plant" encompasses comparison of the "transgenic plant" or "genetically modified plant" to a plant of the same type lacking said heterologous transcribable polynucleotide. A skilled artisan would appreciate that, in some embodiments, a "transcribable polynucleotide" comprises a polynucleotide that can be transcribed into an RNA molecule by an RNA polymerase.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

Transformation of a cell may be stable or transient. The term "transient transformation" or "transiently transformed" refers to the introduction of one or more exogenous polynucleotides into a cell in the absence of integration of the exogenous polynucleotide into the host cell's genome. In contrast, the term "stable transformation" or "stably transformed" refers to the introduction and integration of one or more exogenous polynucleotides into the genome of a cell. The term "stable transformant" refers to a cell which has stably integrated one or more exogenous polynucleotides into the genomic or organellar DNA. It is to be understood that an organism or its cell transformed with the nucleic acids, constructs and/or vectors of the present invention can be transiently as well as stably transformed.

The skilled artisan would appreciate that the term "construct" may encompass an artificially assembled or isolated nucleic acid molecule which includes the polynucleotide of interest. In general, a construct may include the polynucleotide or polynucleotides of interest, a marker gene which in some cases can also be a gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

The skilled artisan would appreciate that the term "expression" may encompass the production of a functional end-product e.g., an mRNA or a protein.

Based on the co-expressed gene array disclosed in the present invention, a pathway from cholesterol to α-tomatine is proposed (FIG. 1). It has been previously described that cholesterol is hydroxylated at C22 by GAME? (US 2012/0159676) followed by GAME8 hydroxylation at the C26 position. The 22,26-dihydroxycholesterol is than hydroxylated at C16 and oxidized at C22 followed by closure of the E-ring by GAME11 and GAME6 to form the furostanol-type aglycone. This order of reactions is supported by the finding of the present invention showing the accumulation of cholestanol-type saponins, lacking hydroxylation at C16 and the hemi-acetal E-ring when silencing GAME11 (FIGS. 8A-D). The furostanol-intermediate is oxidized by GAME4 to its 26-aldehyde which is the substrate for transamination catalyzed by GAME12. Nucleophilic attack of the amino-nitrogen at C22 leads to the formation of tomatidenol which is dehydrogenated to tomatidine. Tomatidine is subsequently converted by GAME1 to T-Gal (Itkin et al., 2011 supra). T-Gal in its turn is glucosylated by GAME17 into γ-tomatine, which is further glucosylated by GAME18 to 01-tomatine that is finally converted to α-tomatine by GAME2 (FIG. 1).

The present invention now shows that by modifying expression of an enzyme and/or other protein involved in the biosynthetic pathway, the level of steroidal alkaloids, steroidal glycoalkaloids and optionally steroidal saponin can be altered.

Silencing of a single gene co-expressed with the clustered enzyme-encoding gene in potato plant, resulted in significant reduction in the amount of the steroidal glycoalkaloids α-chaconine and α-solanine, while overexpression of this gene resulted in significant increase in the content of these substances (FIGS. 5A-5D and 6). This gene was found to include coding sequence comprising an AP2 domain, and therefore postulated to be a transcription factor, designated herein GAME9-transcription factor, encoded by GAME9.

A genetically modified or gene edited plant comprising at least one cell having altered expression of at least one gene selected from the group consisting of a gene encoding GAME9-transcription factor, a gene encoding 2-oxoglutarate-dependent dioxygenase, a gene encoding basic helix-loop-helix (BHLH)-transcription factor or a combination thereof, wherein the genetically modified or gene edited plant has an altered content of at least one steroidal alkaloid or a glycosylated derivative thereof compared to a corresponding unmodified or unedited plant, has been produced. As exemplified herein for 2-oxoglutarate-dependent dioxygenase (GAME11), manipulating the expression of the genes of the present invention can further lead to the manipulation of steroidal saponin synthesis.

Thus, according to additional aspect, the present invention provides a genetically modified or gene edited organism comprising at least one cell having altered expression of at least one gene selected from the group consisting of a gene encoding GAME9-transcription factor, a gene encoding 2-oxoglutarate-dependent dioxygenase, a gene encoding basic helix-loop-helix (BHLH)-transcription factor or a combination thereof compared to an unmodified or unedited organism, wherein the genetically modified or gene edited organism has an altered content of at least one compound selected from steroidal saponin, steroidal alkaloid and glycosylated derivatives thereof compared to a corresponding unmodified or unedited organism.

Unexpectedly, the present invention now shows that SGA levels can be severely reduced in potato tubers by modifying expression of an enzyme and/or transcription factors involved in the steroidal alkaloids biosynthetic pathway.

According to certain embodiments, the expression of the at least one gene selected from the group consisting of a gene encoding GAME9-transcription factor, a gene encoding 2-oxoglutarate-dependent dioxygenase, a gene encoding BHLH-transcription factor or the combination thereof in the genetically modified or gene edited plant is inhibited compared to its expression in the corresponding unmodified or unedited plant, thereby the genetically modified or gene edited plant comprises reduced content of at least one steroidal alkaloid or a glycosylated derivative thereof compared to a corresponding unmodified or unedited plant.

According to certain embodiments, the genetically modified or gene edited plant comprises non-toxic amount of steroidal alkaloid or a glycosylated derivative thereof. As used herein, the term "non-toxic amount" refers to less than 200 mg of antinutritional steroidal; alkaloids or glycoalkaloids per kilogram fresh weight of an edible plant part. According to certain exemplary embodiments, the genetically modified or gene edited plant comprises non-detectable amount of antinutritional steroidal alkaloid or a glycosylated derivative thereof.

Down-regulation or inhibition of the gene expression can be effected on the genomic and/or the transcript level using a variety of molecules that interfere with transcription and/or translation (e.g., antisense, siRNA, Ribozyme, or DNAzyme), or on the protein level using, e.g., antagonists, enzymes that cleave the polypeptide, and the like.

According to certain exemplary embodiments, the genetically modified or gene edited plant is a transgenic plant comprising at least one cell comprising at least one silencing molecule targeted to a gene selected from the group consisting of GAME9, GAME11, BHLH, or GAME15. Each possibility represents a separate embodiment of the present invention.

According to some embodiments, the organism comprising the silencing molecule has an elevated content of at least one steroidal saponin or a derivative thereof compared to a corresponding non-transgenic plant.

The silencing molecule target to at least one of GAME9, GAME11 and BHLH can be designed as is known to a person skilled in the art. According to certain embodiments, the silencing molecule comprises a polynucleotide having a nucleic acid sequence substantially complementary to a region of the GAME9 gene, the gene having the nucleic acids sequence set forth in any one of SEQ ID NO:4 and SEQ ID NO:6.

According to certain additional embodiments, the silencing molecule comprises a polynucleotide having a nucleic acid sequence substantially complementary to a region of the GAME 11 gene, the gene having the nucleic acids sequence set forth in any one of SEQ ID NO:10 and SEQ ID NO:12.

According to certain further embodiments, the silencing molecule comprises a polynucleotide having a nucleic acid sequence substantially complementary to a region of the BHLH gene, the gene having the nucleic acids sequence set forth in any one of SEQ ID NO:15 and SEQ ID NO:17.

According to certain additional embodiments, the silencing molecule comprises a polynucleotide having a nucleic acid sequence substantially complementary to a region of the GAME15 gene, the gene having the nucleic acids sequence set forth in any one of SEQ ID NO:44, SEQ ID NO:45, and SEQ ID NO:46.

Antisense Molecules

Antisense technology is the process in which an antisense RNA or DNA molecule interacts with a target sense DNA or RNA strand. A sense strand is a 5' to 3' mRNA molecule or DNA molecule. The complementary strand, or mirror strand, to the sense is called an antisense. When an antisense strand interacts with a sense mRNA strand, the double helix is recognized as foreign to the cell and will be degraded, resulting in reduced or absent protein production. Although DNA is already a double stranded molecule, antisense technology can be applied to it, building a triplex formation.

One skilled in the art would appreciate that the terms "complementary" or "complement thereof" are used herein to encompass the sequences of polynucleotides which is capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind.

RNA antisense strands can be either catalytic or non-catalytic. The catalytic antisense strands, also called ribozymes, cleave the RNA molecule at specific sequences. A non-catalytic RNA antisense strand blocks further RNA processing.

Antisense modulation of cells and/or tissue levels of the GAME9, GAME11, and BHLH gene or any combination thereof may be effected by transforming the organism cells or tissues with at least one antisense compound, including antisense DNA, antisense RNA, a ribozyme, DNAzyme, a locked nucleic acid (LNA) and an aptamer. In some embodiments the molecules are chemically modified. In other embodiments the antisense molecule is antisense DNA or an antisense DNA analog.

Antisense modulation of cells and/or tissue levels of the GAME15 gene or any combination thereof may be effected by transforming the organism cells or tissues with at least one antisense compound, including antisense DNA, antisense RNA, a ribozyme, DNAzyme, a locked nucleic acid (LNA), and an aptamer. In some embodiments, the molecules are chemically modified. In other embodiments, the antisense molecule is antisense DNA or an antisense DNA analog.

RNA Interference (RNAi) Molecules

RNAi refers to the introduction of homologous double stranded RNA (dsRNA) to target a specific gene product, resulting in post transcriptional silencing of that gene. This phenomenon was first reported in *Caenorhabditis elegans* by Guo and Kemphues (1995, Cell, 81(4):611-620) and subsequently Fire et al. (1998, Nature 391:806-811) discovered that it is the presence of dsRNA, formed from the annealing of sense and antisense strands present in the in vitro RNA preps, that is responsible for producing the interfering activity In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger. The short-nucleotide RNA sequences are homologous to the target gene that is being suppressed. Thus, the short-nucleotide sequences appear to serve as guide sequences to instruct a multicomponent nuclease, RISC, to destroy the specific mRNAs.

The dsRNA used to initiate RNAi, may be isolated from native source or produced by known means, e.g., transcribed from DNA. Plasmids and vectors for generating RNAi molecules against target sequence are now readily available from commercial sources.

The dsRNA can be transcribed from the vectors as two separate strands. In other embodiments, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. Alternatively, a single promoter can derive the transcription of single-stranded hairpin polynucleotide having self-complementary sense and antisense regions that anneal to produce the dsRNA.

One skilled in the art would appreciate that the terms "promoter element," "promoter," or "promoter sequence" may encompass a DNA sequence that is located at the 5' end (i.e. precedes) the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript. The length of the identical nucleotide sequences may be at least 25, 50, 100, 200, 300 or 400 bases. There is no upper limit on the length of the dsRNA that can be used. For example, the dsRNA can range from about 21 base pairs (bp) of the gene to the full length of the gene or more.

The term "RNA interference" or "RNAi" refers to the silencing or decreasing of gene expression mediated by small double stranded RNAs. It is the process of sequence-specific, post-transcriptional gene silencing in animals and plants, initiated by inhibitory RNA (iRNA) that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

One of ordinary skill in the art would appreciate that the term RNAi molecule refers to single- or double-stranded RNA molecules comprising both a sense and antisense sequence. For example, the RNA interference molecule can be a double-stranded polynucleotide molecule comprising self-complementary sense and antisense regions, wherein the antisense region comprises complementarity to a target nucleic acid molecule. Alternatively the RNAi molecule can be a single-stranded hairpin polynucleotide having self-complementary sense and antisense regions, wherein the antisense region comprises complementarity to a target nucleic acid molecule or it can be a circular single-stranded polynucleotide having two or more loop structures and a stem comprising self-complementary sense and antisense regions, wherein the antisense region comprises complementarity to a target nucleic acid molecule, and wherein the circular polynucleotide can be processed either in vivo or in vitro to generate an active molecule capable of mediating RNAi.

The present invention contemplates the use of RNA interference (RNAi) to down regulate the expression of GAME9, GAME11, BHLH, or GAME15 or a combination thereof to attenuate the level of steroidal alkaloids/glycoalkaloids in plants. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger. The short-nucleotide RNA sequences are homologous to the target gene that is being suppressed. Thus, the short-nucleotide sequences appear to serve as guide sequences to instruct a multicomponent nuclease, RISC, to destroy the specific mRNAs.

The dsRNA used to initiate RNAi, may be isolated from native source or produced by known means, e.g., transcribed from DNA. Plasmids and vectors for generating RNAi molecules against target sequence are now readily available as exemplified herein below.

The dsRNA can be transcribed from the vectors as two separate strands. In other embodiments, the two strands of DNA used to form the dsRNA may belong to the same or two different duplexes in which they each form with a DNA strand of at least partially complementary sequence. When the dsRNA is thus-produced, the DNA sequence to be transcribed is flanked by two promoters, one controlling the transcription of one of the strands, and the other that of the complementary strand. These two promoters may be identical or different. Alternatively, a single promoter can derive the transcription of single-stranded hairpin polynucleotide having self-complementary sense and antisense regions that anneal to produce the dsRNA.

Inhibition is sequence-specific in that nucleotide sequences corresponding to the duplex region of the RNA are targeted for genetic inhibition. RNA molecules containing a nucleotide sequence identical to a portion of the target gene are preferred for inhibition. RNA sequences with insertions, deletions, and single point mutations relative to the target sequence have also been found to be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript. The length of the identical nucleotide sequences may be at least 25, 50, 100, 200, 300 or 400 bases. There is no upper limit on the length of the dsRNA that can be used. For example, the dsRNA can range from about 21 base pairs (bp) of the gene to the full length of the gene or more.

According to certain currently typical embodiments, the silencing molecule is RNAi targeted to the GAME9 gene, comprising the nucleic acid sequence set forth in SEQ ID NO:18 or a complementary sequence thereof. According to certain currently typical embodiments, the silencing molecule is RNAi targeted to the cellulose synthase like GAME15 gene, comprising the nucleic acid sequence set forth any one of in SEQ ID NOs: 44 to 46 or a complementary sequence thereof.

According to additional typical embodiments, the silencing molecule is RNAi targeted to the GAME11 gene, comprising the nucleic acid sequence set forth in SEQ ID NO:19 or a complementary sequence thereof.

According to additional typical embodiments, the silencing molecule is RNAi targeted to the GAME15 gene, comprising the nucleic acid sequence set forth in SEQ ID NO:44 or a complementary sequence thereof; SEQ ID NO:45 or a complementary sequence thereof; and/or SEQ ID NO:46 or a complementary sequence thereof.

Co-Suppression Molecules

Another agent capable of down-regulating the expression of GAME9 or GAME11, or a combination thereof is a Co-Suppression molecule. Co-suppression is a post-transcriptional mechanism where both the transgene and the endogenous gene are silenced.

Another agent capable of down-regulating the expression of GAME15 is a Co-Suppression molecule. Co-suppression is a post-transcriptional mechanism where both the transgene and the endogenous gene are silenced.

DNAzyme Molecules

Another agent capable of down-regulating the expression of GAME9, GAME11, BHLH, or GAME15 is a DNAzyme molecule, which is capable of specifically cleaving an mRNA transcript or a DNA sequence of the GAME9, GAME 11, BHLH, or GAME15. DNAzymes are single-stranded polynucleotides that are capable of cleaving both single- and double-stranded target sequences. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (for review of DNAzymes, see: Khachigian, L. M. (2002) Curr Opin Mol Ther 4, 119-121).

Examples of construction and amplification of synthetic, engineered DNAzymes recognizing single- and double-stranded target cleavage sites are disclosed in U.S. Pat. No. 6,326,174.

Enzymatic Oligonucleotide

The terms "enzymatic nucleic acid molecule" or "enzymatic oligonucleotide" refers to a nucleic acid molecule which has complementarity in a substrate binding region to a specified gene target, and also has an enzymatic activity which is active to specifically cleave target RNA of GAME9, GAME11, BHLH, or GAME15, thereby silencing each of the genes. The complementary regions allow sufficient hybridization of the enzymatic nucleic acid molecule to the target RNA and subsequent cleavage. The term enzymatic nucleic acid is used interchangeably with for example, ribozymes, catalytic RNA, enzymatic RNA, catalytic DNA, aptazyme or aptamer-binding ribozyme, catalytic oligonucleotide, nucleozyme, DNAzyme, RNAenzyme. The specific enzymatic nucleic acid molecules described in the instant application are not limiting and an enzymatic nucleic acid molecule of this invention requires a specific substrate binding site which is complementary to one or more of the target nucleic acid regions, and that it have nucleotide sequences within or surrounding that substrate binding site which impart a nucleic acid cleaving and/or ligation activity to the molecule. U.S. Pat. No. 4,987,071 discloses examples of such molecules.

Mutagenesis

Altering the expression of endogenous GAME9, GAME11, BHLH, or GAME15 genes can be also achieved by the introduction of one or more point mutations into a nucleic acid molecule encoding the corresponding proteins. Mutations can be introduced using, for example, site-directed mutagenesis (see, e.g. Wu Ed., 1993 Meth. In Enzymol. Vol. 217, San Diego: Academic Press; Higuchi, "Recombinant PCR" in Innis et al. Eds., 1990 PCR Protocols, San Diego: Academic Press, Inc). Such mutagenesis can be used to introduce a specific, desired amino acid insertion, deletion or substitution. Several technologies for targeted mutagenesis are based on the targeted induction of double-strand breaks (DSBs) in the genome followed by error-prone DNA repair. Mostly commonly used for genome editing by these methods are custom designed nucleases, including zinc finger nucleases and Xanthomonas-derived transcription activator-like effector nuclease (TALEN) enzymes.

In some embodiments, when the expression of the at least one gene or combination thereof is altered, said altering comprises mutagenizing the at least one gene, said mutation present within a coding region of said at least one gene, or a regulatory sequence of said at least one gene, or a combination thereof.

Various types of mutagenesis can be used to modify GAME9, GAME11, BHLH, or GAME15 and their encoded polypeptides in order to produce conservative or non-conservative variants. Any available mutagenesis procedure can be used. In some embodiments, the mutagenesis procedure comprises site-directed point mutagenesis. In some embodiments, the mutagenesis procedure comprises random point mutagenesis. In some embodiments, the mutagenesis procedure comprises in vitro or in vivo homologous recombination (DNA shuffling). In some embodiments, the mutagenesis procedure comprises mutagenesis using uracilcontaining templates. In some embodiments, the mutagenesis procedure comprises oligonucleotide-directed mutagenesis. In some embodiments, the mutagenesis procedure comprises phosphorothioate-modified DNA mutagenesis. In some embodiments, the mutagenesis procedure comprises mutagenesis using gapped duplex DNA. In some embodiments, the mutagenesis procedure comprises point mismatch repair. In some embodiments, the mutagenesis procedure comprises mutagenesis using repair-deficient host strains. In some embodiments, the mutagenesis procedure comprises restriction-selection and restriction-purification. In some embodiments, the mutagenesis procedure comprises deletion mutagenesis. In some embodiments, the mutagenesis procedure comprises mutagenesis by total gene synthesis. In some embodiments, the mutagenesis procedure comprises double-strand break repair. In some embodiments, the mutagenesis procedure comprises mutagenesis by chimeric constructs. In some embodiments, the mutagenesis procedure comprises mutagenesis by CRISPR/Cas. In some embodiments, the mutagenesis procedure comprises mutagenesis by zinc-finger nucleases (ZFN). In some embodiments, the mutagenesis procedure comprises mutagenesis by transcription activator-like effector nucleases (TALEN). In some embodiments, the mutagenesis procedure comprises any other mutagenesis procedure known to a person skilled in the art.

In some embodiments, mutagenesis can be guided by known information about the naturally occurring molecule and/or the mutated molecule. By way of example, this known information may include sequence, sequence comparisons, physical properties, crystal structure and the like. In some embodiments, the mutagenesis is essentially random. In some embodiments the mutagenesis procedure is DNA shuffling.

A skilled artisan would appreciate that clustered regularly interspaced short palindromic repeats (CRISPR)/CRISPR associated protein (Cas) system comprises genome engineering tools based on the bacterial CRISPR/Cas prokaryotic adaptive immune system. This RNA-based technology is very specific and allows targeted cleavage of genomic DNA guided by a customizable small noncoding RNA, resulting in gene modifications by both non-homologous end joining (NHEJ) and homology-directed repair (HDR) mechanisms (Belhaj K. et al., 2013. Plant Methods 2013, 9:39). In some embodiments, a CRISPR/Cas system comprises a CRISPR/Cas9 system.

In some embodiments, a CRISPR/Cas system comprises a single-guide RNA (sgRNA) and/or a Cas protein known in the art. In some embodiments, a CRISPR/Cas system comprises a single-guide RNA (sgRNA) and/or a Cas protein newly created to cleave at a preselected site. The skilled artisan would appreciate that the terms "single-guide RNA", "sgRNA", and "gRNA" are interchangeable having all the same qualities and meanings, wherein an sgRNA may encompass a chimeric RNA molecule which is composed of a CRISPR RNA (crRNA) and trans-encoded CRISPR RNA (tracrRNA). In some embodiments, a crRNA is complementary to a preselected region of GAME15 DNA, wherein the crRNA "targets" the CRISPR associated polypeptide (Cas) nuclease protein to the preselected target site.

In some embodiments, the length of crRNA sequence complementary is 19-22 nucleotides long e.g., 19-22 consecutive nucleotides complementary to the target site. In another embodiment, the length of crRNA sequence complementary to the region of DNA is about 15-30 nucleotides long. In another embodiment, the length of crRNA sequence complementary to the region of DNA is about 15, 16, 17, 18, 19, 20, 21, 22, 23, 24, 25, 26, 27, 28, 29, or 30 nucleotides long. In another embodiment, the length of crRNA sequence complementary to the region of DNA is 20 nucleotides long. In some embodiments, the crRNA is located at the 5' end of the sgRNA molecule. In another embodiment, the crRNA comprises 100% complementation within the preselected target sequence. In another embodiment, the crRNA comprises at least 80% complementation within the preselected target sequence. In another embodiment, the crRNA comprises at least 85% complementation within the preselected target sequence. In another embodiment, the crRNA comprises at least 90% complementation within the preselected target sequence. In another embodiment, the crRNA comprises at least 95% complementation within the preselected target sequence. In another embodiment, the crRNA comprises at least 97% complementation within the preselected target sequence. In another embodiment, the crRNA comprises at least 99% complementation within the preselected target sequence. In another embodiment, a tracrRNA is 100-300 nucleotides long and provides a binding site for the Cas nuclease, e.g., a Cas9 protein forming the CRISPR/Cas9 complex.

In one embodiment, a mutagenesis system comprises a CRISPR/Cas system. In another embodiment, a CRISPR/Cas system comprises a Cas nuclease and a gRNA molecule, wherein said gRNA molecule binds within said preselected endogenous target site thereby guiding said Cas nuclease to cleave the DNA within said preselected endogenous target site.

In some embodiments, a CRISPR/Cas system comprise an enzyme system including a guide RNA sequence ("gRNA" or "sgRNA") that contains a nucleotide sequence complementary or substantially complementary to a region of a target polynucleotide, for example a preselected endogenous target site, and a protein with nuclease activity.

In another embodiment, a CRISPR/Cas system comprises a Type I CRISPR-Cas system, or a Type II CRISPR-Cas system, or a Type III CRISPR-Cas system, or derivatives thereof. In another embodiment, a CRISPR-Cas system comprises an engineered and/or programmed nuclease system derived from naturally accruing CRISPR-Cas systems. In another embodiment, a CRISPR-Cas system comprises engineered and/or mutated Cas proteins. In another embodiment, a CRISPR-Cas system comprises engineered and/or programmed guide RNA.

A skilled artisan would appreciate that a guide RNA may contain nucleotide sequences other than the region complementary or substantially complementary to a region of a target DNA sequence, for example a preselected endogenous target site. In another embodiment, a guide RNA comprises a crRNA or a derivative thereof. In another embodiment, a guide RNA comprises a crRNA: tracrRNA chimera.

In another embodiment, a gRNA molecule comprises a domain that is complementary to and binds to a preselected endogenous target site on at least one homologous chromosome. In another embodiment, a gRNA molecule comprises a domain that is complementary to and binds to a polymorphic allele on at least one homologous chromosome. In another embodiment, a gRNA molecule comprises a domain that is complementary to and binds to a preselected endogenous target site on both homologous chromosomes. In another embodiment, a gRNA molecule comprises a domain that is complementary to and binds to polymorphic alleles on both homologous chromosomes.

Cas enzymes comprise RNA-guided DNA endonuclease able to make double-stranded breaks (DSB) in DNA. The term "Cas enzyme" may be used interchangeably with the terms "CRISPR-associated endonucleases" or "CRISPR-associated polypeptides" having all the same qualities and meanings. In one embodiment, a Cas enzyme is selected from the group comprising Cas1, Cas1B, Cas2, Cas3, Cas4, Cas5, Cas6, Cas7, Cas8, Cas9, Cas10, C2c1, CasX, NgAgo, Cpf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4, or homologs thereof, or modified versions thereof. In another embodiment, a Cas enzyme comprises Cas9. In another embodiment, a Cas enzyme comprises Cas1. In another embodiment, a Cas enzyme comprises Cas1B. In another embodiment, a Cas enzyme comprises Cas2. In another embodiment, a Cas enzyme comprises Cas3. In another embodiment, a Cas enzyme comprises Cas4. In another embodiment, a Cas enzyme comprises Cas5. In another embodiment, a Cas enzyme comprises Cas6. In another embodiment, a Cas enzyme comprises Cas7. In another embodiment, a Cas enzyme comprises Cas8. In another embodiment, a Cas enzyme comprises Cas10. In another embodiment, a Cas enzyme comprises Cpf1. In another embodiment, a Cas enzyme comprises Csy1. In another embodiment, a Cas enzyme comprises Csy2. In another embodiment, a Cas enzyme comprises Csy3. In another embodiment, a Cas enzyme comprises Cse1. In another embodiment, a Cas enzyme comprises Cse2. In another embodiment, a Cas enzyme comprises Csc1. In another embodiment, a Cas enzyme comprises Csc2. In another embodiment, a Cas enzyme comprises Csa5. In another embodiment, a Cas enzyme comprises Csn2. In another embodiment, a Cas enzyme comprises Csm2. In another embodiment, a Cas enzyme comprises Csm3. In another embodiment, a Cas enzyme comprises Csm4. In another embodiment, a Cas enzyme comprises Csm5. In another embodiment, a Cas enzyme comprises Csm6. In another embodiment, a Cas enzyme comprises Cmr1. In another embodiment, a Cas enzyme comprises Cmr3. In another embodiment, a Cas enzyme comprises Cmr4. In another embodiment, a Cas enzyme comprises Cmr5. In another embodiment, a Cas enzyme comprises Cmr6. In another embodiment, a Cas enzyme comprises Csb 1. In another embodiment, a Cas enzyme comprises Csb2. In another embodiment, a Cas enzyme comprises Csb3. In another embodiment, a Cas enzyme comprises Csx17. In another embodiment, a Cas enzyme comprises Csx14. In another embodiment, a Cas enzyme comprises Csx10. In another embodiment, a Cas enzyme comprises Csx16, CsaX. In another embodiment, a Cas enzyme comprises Csx3. In another embodiment, a Cas enzyme comprises Csx1, Csx15, Csf1. In another embodiment, a Cas enzyme comprises Csf2. In another embodiment, a Cas enzyme comprises Csf3. In another embodiment, a Cas enzyme comprises Csf4. In another embodiment, a Cas enzyme comprises Cpf1. In another embodiment, a Cas enzyme comprises C2c1. In another embodiment, a Cas enzyme comprises CasX. In another embodiment, a Cas enzyme comprises NgAgo. In another embodiment, a Cas enzyme is Cas homologue. In another embodiment, a Cas enzyme is a Cas orthologue. In another embodiment, a Cas enzyme is a modified Cas enzyme. In another embodiment, a Cas enzyme is any CRISPR-associated endonucleases known in the art.

A skilled artisan would appreciate that the terms "zinc finger nuclease" or "ZFN" are interchangeable having all the same meanings and qualities, wherein a ZFN encompasses a chimeric protein molecule comprising at least one zinc finger DNA binding domain operatively linked to at least one nuclease capable of double-strand cleaving of DNA. In some embodiments, a ZFN system comprises a ZFN known in the art. In some embodiments, a ZFN system comprises a ZFN newly created to cleave a preselected site.

In some embodiments, a ZFN creates a double-stranded break at a preselected endogenous target site. In some embodiments, a ZFN comprises a DNA-binding domain and a DNA-cleavage domain, wherein the DNA binding domain is comprised of at least one zinc finger and is operatively linked to a DNA-cleavage domain. In another embodiment, a zinc finger DNA-binding domain is at the N-terminus of the chimeric protein molecule and the DNA-cleavage domain is located at the C-terminus of the molecule. In another embodiment, a zinc finger DNA-binding domain is at the C-terminus of the chimeric protein molecule and the DNA-cleavage domain is located at the N-terminus of the molecule. In another embodiment, a zinc finger binding domain encompasses the region in a zinc finger nuclease that is capable of binding to a target locus, for example a preselected endogenous target site as disclosed herein. In another embodiment, a zinc finger DNA-binding domain comprises a protein domain that binds to a preselected endogenous target site on at least one homologous chromosome. In another embodiment, a zinc finger DNA-binding domain comprises a protein domain that binds to a polymorphic allele on at least one homologous chromosome. In another embodiment, a zinc finger DNA-binding domain comprises a protein domain that binds to a preselected endogenous target site on both homologous chromosomes. In another embodiment, a zinc finger DNA-binding domain comprises a protein domain that binds to polymorphic alleles on both homologous chromosomes.

The skilled artisan would appreciate that the term "chimeric protein" is used to describe a protein that has been expressed from a DNA molecule that has been created by operatively joining two or more DNA fragments. The DNA fragments may be from the same species, or they may be from a different species. The DNA fragments may be from the same or a different gene. The skilled artisan would appreciate that the term "DNA cleavage domain" of a ZFN encompasses the region in the zinc finger nuclease that is capable of breaking down the chemical bonds between nucleic acids in a nucleotide chain. Examples of proteins containing cleavage domains include restriction enzymes, topoisomerases, recombinases, integrases and DNAses.

In some embodiments, a TALEN system comprises a TAL effector DNA binding domain and a DNA cleavage domain, wherein said TAL effector DNA binding domain binds within said preselected endogenous target site, thereby targeting the DNA cleavage domain to cleave the DNA within said preselected endogenous target site.

A skilled artisan would appreciate that the terms "transcription activator-like effector nuclease", "TALEN", and "TAL effector nuclease" may be used interchangeably having all the same meanings and qualities, wherein a TALEN encompasses a nuclease capable of recognizing and cleaving its target site, for example a preselected endogenous target site as disclosed herein. In another embodiment, a TALEN comprises a fusion protein comprising a TALE domain and a nucleotide cleavage domain. In another embodiment, a TALE domain comprises a protein domain that binds to a nucleotide in a sequence-specific manner through one or more TALE-repeat modules. A skilled artisan would recognize that TALE-repeat modules comprise a variable number of about 34 amino acid repeats that recognize plant DNA sequences. Further, repeat modules can be rearranged according to a simple cipher to target new DNA sequences. In another embodiment, a TALE domain comprises a protein domain that binds to a preselected endogenous target site on at least one homologous chromosome. In another embodiment, a TALE domain comprises a protein domain that binds to a polymorphic allele on at least one homologous chromosome. In another embodiment, a TALE domain comprises a protein domain that binds to a preselected endogenous target site on both homologous chromosomes. In another embodiment, a TALE domain comprises a protein domain that binds to polymorphic alleles on both homologous chromosomes.

In one embodiment, a TALE domain comprises at least one of the TALE-repeat modules. In another embodiment, a TALE domain comprises from one to thirty TALE-repeat modules. In another embodiment, a TALE domain comprises more than thirty repeat modules. In another embodiment, a TALEN fusion protein comprises an N-terminal domain, one or more of TALE-repeat modules followed by a half-repeat module, a linker, and a nucleotide cleavage domain.

Chemical mutagenesis using an agent such as Ethyl Methyl Sulfonate (EMS) can be employed to obtain a population of point mutations and screen for mutants of the GAME9, GAME11, BHLH, or GAME15 genes that may become silent or down-regulated. In plants, methods relaying on introgression of genes from natural populations can be used. Cultured and wild types species are crossed repetitively such that a plant comprising a given segment of the wild genome is isolated. Certain plant species, for example, maize (corn) and snapdragon, have natural transposons. These transposons are either autonomous, i.e. the transposase is located within the transposon sequence or non-autonomous, without a transposase. A skilled person can cause transposons to "jump" and create mutations. Alternatively, a nucleic acid sequence can be synthesized having random nucleotides at one or more predetermined positions to generate random amino acid substituting.

In some embodiments, the expression of endogenous GAME9, GAME11, BHLH, or GAME15 genes can be altered by the introduction of one or more point mutations into their regulatory sequences. In some embodiments, the expression of exogenous GAME9, GAME11, BHLH, or GAME15 genes can be altered by the introduction of one or more point mutations into their regulatory sequences. A skilled artisan would appreciate that "regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. In some embodiments, regulatory sequences comprise promoters. In some embodiments, regulatory sequences comprise translation leader sequences. In some embodiments, regulatory sequences comprise introns. In some embodiments, regulatory sequences comprise polyadenylation recognition sequences. In some embodiments, regulatory sequences comprise RNA processing sites. In some embodiments, regulatory sequences comprise effector binding sites. In some embodiments, regulatory sequences comprise stem-loop structures.

A skilled artisan would appreciate that "promoter" refers to a DNA sequence capable of controlling the expression of a coding sequence or functional RNA. In some embodiments, a coding sequence is located 3' to a promoter sequence. It is understood by those skilled in the art that different promoters may direct the expression of a gene in different tissues or cell types, or at different stages of development, or in response to different environmental or physiological conditions. In some embodiments, the promoter comprises a constitutive promoter, i.e., a promoter that causes a gene to be expressed in most cell types at most times. In some embodiments, the promoter comprises a regulated promoter, i.e., a promoter that causes a gene to be expressed in response to sporadic specific stimuli. It is further recognized that in many cases the exact boundaries of regulatory sequences have not been completely defined yet.

A skilled artisan would appreciate that the term "3' non-coding sequences" or "transcription terminator" refers to DNA sequences located downstream of a coding sequence. In some embodiments, 3' non-coding sequences comprise polyadenylation recognition sequences. In some embodiments, 3' non-coding sequences comprise sequences encoding regulatory signals capable of affecting mRNA processing. In some embodiments, 3' non-coding sequences comprise sequences encoding regulatory signals capable of affecting gene expression. The polyadenylation signal is usually characterized by affecting the addition of polyadenylic acid tracts to the 3' end of the mRNA precursor. In some embodiments, mutations in the 3' non-coding sequences affect gene transcription. In some embodiments, mutations in the 3' non-coding sequences affect RNA processing. In some embodiments, mutations in the 3' non-coding sequences affect gene stability. In some embodiments, mutations in the 3' non-coding sequences affect translation of the associated coding sequence.

Biological Activity

In some embodiments, the biological activity of GAME9, GAME11, BHLH, GAME15 is altered compared with a control GAME9 enzyme, a control GAME11 enzyme, a control BHLH enzyme, or a control GAME15 protein.

A skilled artisan would recognize that the term "biological activity" refers to any activity associated with a protein that can be measured by an assay. In some embodiments, the biological activity of GAME15 comprises biosynthesis of steroidal alkaloids and glycosylated derivatives thereof. In some embodiments, the biological activity of GAME15 affect the levels of steroidal alkaloids in at least a part of a plant. In some embodiments, an altered biological activity comprises increased enzyme activity. In some embodiments, an altered biological activity comprises decreased enzyme activity. In some embodiments, an altered biological activity comprises increased stability of the polypeptide. In some embodiments, an altered biological activity comprises decreased stability of the polypeptide.

In some embodiments, the altered biological activity comprises
  increased enzyme activity of said cellulose synthase like gene enzyme (GAME15); or
  increased stability of said cellulose synthase like gene enzyme (GAME15); or
  decreased enzyme activity of said cellulose synthase like gene enzyme (GAME15); or
  decreased stability of said cellulose synthase like gene enzyme (GAME15);
compared to the biological activity in an unmodified or unedited plant.

In some embodiments, the biological activity of a GAME15 enzyme is increased compared with a control GAME15 enzyme. In some embodiments, the biological activity of a GAME 15 enzyme is decreased compared with a control GAME15 enzyme. In some embodiments, a GAME15 enzyme has increased stability compared with a control GAME15 enzyme. In some embodiments, a GAME15 enzyme has decreased stability compared with a control GAME15 enzyme.

Overexpression

According to yet additional embodiments the present invention provides a genetically modified or gene edited plant having enhanced expression of at least one gene selected from the group consisting of a gene encoding GAME9-transcription factor, a gene encoding 2-oxoglutarate-dependent dioxygenase, a gene encoding basic helix-loop-helix transcription factor (BHLH), a gene encoding GAME15, or a combination thereof, wherein the genetically modified or gene edited plant has an increased amount of at least one steroidal alkaloid or a glycosylated derivative thereof compared to a corresponding unmodified or unedited plant. In plants, steroidal alkaloids play a role in protecting the plant from various pathogens. Steroidal alkaloids are referred to as phytoanticipins, i.e. low molecular weight anti-microbial compounds that are present in the plant before challenge by microorganisms or produced after infection solely from preexisting constituents. Over-expression of GAME9, GAME11, BHLH, GAME15, or any combination thereof in non-edible parts of the plant can thus enhance the plant resistance to steroidal-alkaloid-sensitive pathogens.

Transgenic Plants

Cloning of a polynucleotide encoding a protein of the present invention selected from the group consisting of GAME9-transcription factor, 2-oxoglutarate-dependent dioxygenase, BHLH transcription factor, GAME15 or a molecule that silences a gene encoding same can be performed by any method as is known to a person skilled in the art. Cloning of a polynucleotide encoding a GAME15 protein of the present invention or a molecule that silences a gene encoding same can be performed by any method as is known to a person skilled in the art. Various DNA constructs may be used to express the desired gene or silencing molecule targeted to the gene in a desired organism.

According to certain embodiments, the gene or a silencing molecule targeted thereto form part of an expression vector comprising all necessary elements for expression of the gene or its silencing molecule. According to certain embodiments, the expression is controlled by a constitutive promoter. According to certain embodiments, the constitutive promoter is specific to a plant tissue. According to these embodiments, the tissue specific promoter is selected from the group consisting of root, tuber, leaves and fruit specific promoter. Root specific promoters are described, e.g. in Martinez, E. et al. 2003. Curr. Biol. 13:1435-1441. Fruit specific promoters are described among others in Estornell L. H et al. 2009. Plant Biotechnol. J. 7:298-309 and Fernandez A. I. Et al. 2009 Plant Physiol. 151:1729-1740. Tuber specific promoters are described, e.g. in Rocha-Sosa M, et al., 1989. EMBO J. 8:23-29; McKibbin R. S. et al., 2006. Plant Biotechnol J. 4(4):409-18. Leaf specific promoters are described, e.g. in Yutao Yang, Guodong Yang, Shijuan Liu, Xingqi Guo and Chengchao Zheng. Science in China Series C: Life Sciences. 46: 651-660.

According to certain embodiments, the expression vector further comprises regulatory elements at the 3' non-coding sequence. As used herein, the "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht I L et al. (1989. Plant Cell 1:671-680).

Those skilled in the art will appreciate that the various components of the nucleic acid sequences and the transformation vectors described in the present invention are operatively linked, so as to result in expression of said nucleic acid or nucleic acid fragment. Techniques for operatively linking the components of the constructs and vectors of the present invention are well known to those skilled in the art. Such techniques include the use of linkers, such as synthetic linkers, for example including one or more restriction enzyme sites.

One skilled in the art would appreciate that the term "operably linked" may encompass the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation.

Methods for transforming a plant according to the teachings of the present invention are known to those skilled in the art. As used herein the term "transformation" or "transforming" describes a process by which a foreign DNA, such as a DNA construct, including expression vector, enters and changes a recipient cell into a transformed, genetically altered or transgenic cell. Transformation may be stable, wherein the nucleic acid sequence is integrated into the organism genome and as such represents a stable and inherited trait, or transient, wherein the nucleic acid sequence is expressed by the cell transformed but is not integrated into the genome, and as such represents a transient trait. According to preferred embodiments the nucleic acid sequence of the present invention is stably transformed into the plant cell.

The genetically altered plants having altered content of the desired steroidal alkaloid(s) or steroidal saponin(s) according to the teachings of the present invention are typically first selected based on the expression of the gene or protein. Plants having enhanced or aberrant expression of the gene or protein, are then analyzed for the content of steroidal alkaloids and optionally of steroidal saponins.

Detection of mutated GAME9, GAME11, BHLH, or GAME15 gene and/or the presence of silencing molecule targeted to the gene and/or over-expression of the genes is performed employing standard methods of molecular genetics, known to a person of ordinary skill in the art.

For measuring the gene(s) or silencing molecule(s) expression, cDNA or mRNA should be obtained from an organ in which the nucleic acid is expressed. The sample may be further processed before the detecting step. For example, the polynucleotides in the cell or tissue sample may be separated from other components of the sample, may be amplified, etc. All samples obtained from an organism, including those subjected to any sort of further processing are considered to be obtained from the organism.

Detection of the gene(s) or the silencing molecule(s) typically requires amplification of the polynucleotides taken from the candidate altered organism. Methods for DNA amplification are known to a person skilled in the art. Most commonly used method for DNA amplification is PCR (polymerase chain reaction; see, for example, PCR Basics: from background to Bench, Springer Verlag, 2000; Eckert et al., 1991. PCR Methods and Applications 1:17). Additional suitable amplification methods include the ligase chain reaction (LCR), transcription amplification and self-sustained sequence replication, and nucleic acid-based sequence amplification (NASBA).

According to certain embodiments, the nucleic acid sequence comprising the GAME9, GAME11, BHLH, or GAME15 gene or its silencing molecule further comprises a nucleic acid sequence encoding a selectable marker. According to certain embodiments, the selectable marker confers resistance to antibiotic or to an herbicide; in these embodiments the transgenic plants are selected according to their resistance to the antibiotic or herbicide.

Breeding

In some embodiments, transformation techniques including breeding through transgene editing, use of transgenes, use of transient expression of a gene or genes, or use of molecular markers, or any combination thereof, may be used in the breeding of a plant having an altered expression. If transformation techniques require use of tissue culture, transformed cells may be regenerated into plants in accordance with techniques well known to those of skill in the art. The regenerated plants may then be grown and crossed with the same or different plant varieties using traditional breeding techniques to produce seed, which are then selected under the appropriate conditions.

The content of steroidal alkaloids and/or steroidal saponins is measured as exemplified hereinbelow and as is known to a person skilled in the art.

In some embodiments, an offspring plant comprises decreased anti-nutritional contents or decreased toxins compared to at least one of the progenitor plants. In some embodiments, an offspring plant comprises improved resistance to a plant pathogen, pest, or predator compared to at least one of the progenitor plants.

In one embodiment, a plant as disclosed herein comprises a Solanaceae crop plant. In some embodiments, a Solanaceae crop plant is selected from the group consisting of *Solanum lycopersicum, Solanum pennellii, Solanum tuberosum, Solanum chacoense, Capsicum annuum,* and *Solanum melongena*. In some embodiments, a Solanaceae plant is selected from the group consisting of ground cherry, eggplant, potato, tomato, pepper, bell pepper, cayenne pepper, chili pepper, pimiento, tabasco pepper, tobacco, and bittersweet. In some embodiments, a Solanaceae plant comprises any Solanaceae plant that produces a steroidal alkaloid or a glycosylated derivative thereof, or an unsaturated or saturated steroidal saponin or a glycoside derivative thereof, or any combination thereof.

A skilled artisan would appreciate that plant breeding can be accomplished through many different techniques ranging from simply selecting plants with desirable characteristics for propagation, to methods that make use of knowledge of genetics and chromosomes, to more complex molecular techniques.

A skilled artisan would appreciate that the term "hybrid plant" may encompass a plant generated by crossing two plants of interest, propagating by seed or tissue and then growing the plants. When plants are crossed sexually, the step of pollination may include cross pollination or self-pollination or back crossing with an untransformed plant or another transformed plant. Hybrid plants include first generation and later generation plants. Disclosed herein is a method to manipulate and improve a plant trait, for a non-limiting example—increasing plant resistance, decreasing anti-nutritional properties in a plant, or decreasing toxins in a plant, or any combination thereof.

Biomarkers

A skilled artisan would appreciate that the term "biomarker" comprises any measurable substance in an organism whose presence is indicative of a biological state or a condition of interest. In some embodiments, the presence of a biomarker is indicative of the presence of a compound or a group of compounds of interest. In some embodiments, the concentration of a biomarker is indicative of the concentration of a compound or a group of compounds of interest. In some embodiments, the concentration of a biomarker is indicative of an organism phenotype.

Cellulose synthase like enzymes are hereby disclosed to have an essential role in the biosynthesis of steroidal alkaloids found in Solanaceae plants. Thus, in some embodiments, the expression level of GAME15 is indicative of the capacity of a plant to produce steroidal alkaloids or glycosylated derivatives thereof, as well as α-tomatine and dehydrotomatine (e.g., in *Solanum lycopersicum* or tomato), α-chaconine and α-solanine (e.g., in *Solanum tuberosum* or potato), or α-solamargine and α-solasonine (e.g., in *Solanum melongena* or eggplant).

Further, one skilled in the art would appreciate that the term "comprising" used throughout is intended to mean that the genetically modified or gene edited plants disclosed herein, and methods of altering expression of genes, and altering production of SA and/or SGA within these genetically modified or gene edited plants includes the recited elements, but not excluding others which may be optional. "Consisting of" shall thus mean excluding more than traces of other elements. The skilled artisan would appreciate that while, in some embodiments the term "comprising" is used, such a term may be replaced by the term "consisting of", wherein such a replacement would narrow the scope of inclusion of elements not specifically recited.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods
Plant Material, Treatments and Generation of Transgenic Plants Tomato (*Solanum lycopersicum*, cv. Micro Tom) and potato (*Solanum tuberosum*; cultivar Desiree) plants were collected as described previously (Itkin et al., 2001, supra). In potato, when the green parts started to dry, mature tubers (Stage 3) were collected, washed of soil, dried and kept at 4° C., at complete darkness.

The GAME9-silenced (RNAi) and overexpression (OX) constructs were created by introducing the corresponding GAME9 DNA fragments to pK7GWIWG2(II) and pJCV52 binary vectors, respectively. Transgenic lines for silencing and overexpression of GAME9 in tomato and potato were generated and tissue extracts were prepared and analyzed according to Itkin et al. (2011, supra).

Table 1 below describes the oligonucleotides used for generation of the constructs described herein. The GAME4-silencing (RNAi; GAME4i), GAME4 overexpressing (GAME4oe) and GAMER-silencing constructs were generated as described previously (Itkin et al., 2001, supra; WO 2012/095843).

TABLE 1

Oligonucleotides used for construct production

| Name | Sequence 5' to 3'/ Description | SEQ ID NO. |
|---|---|---|
| S107g0434 20 EcoRI Fw | AAAAAgaattcCGGATCTTCTC TCGAACTGGTCAA<br>To prepare GAME11 virus-induced gene silencing (VIGS) construct | 20 |
| S107g0434 20 EcoRI Rv | AAAAAgaattcCACTTTCATT GCTTCATCCATTAGATCT<br>To prepare GAME11 VIGS construct | 21 |
| S107g0435 00 EcoRI Fw | AAAAAgaattcCTTAGCTTAT GGCCACATCACACCTT<br>To prepare GAME18 VIGS construct | 22 |
| S107g043500 EcoRI Rv | AAAAAgaattcACTCAAGATT TGGTGAAGCTGTGGTT<br>To prepare GAME18 VIGS construct | 23 |
| G8-Forward (AscI) | AAAAAGGCGCGCCAATCATAG AGAAGAAAGAAGACG<br>To construct RNAi of GAME8 | 24 |
| G8-Reverse (NotI) | AAAAAGCGGCCGCACTCCTGC AGGAATTGTCATTTCTC<br>To construct RNAi of GAME8 | 25 |
| GAME9 RNAi NotI Fw | aaaaaGCGGCCGCATGAGTAT TGTAATTGATGATGATGAA ATC<br>To construct RNAi of GAME9 | 26 |
| GAME9 RNAi AscI Rv | aaaaGGCGCGCCCACACGCCA CAGATGGTTCTT<br>To construct RNAi of GAME9 | 27 |
| GAME9-Tom GWFw | GGGGACAAGTTTGTACAAAAA AGCAGGCTATGAGTATT GTAATTGATGATGATGAAATC<br>To pick up the gene from cDNA for overexpression (good for tomato) | 28 |
| GAME9-Tom GWRv | GGGGACCACTTTGTACAAGAA AGCTGGGTTCATACTAC CTTCTGTCCTAAGCCT<br>To pick up the gene from cDNA for over-expression (good for tomato) | 29 |
| GAME9-Pot GW Fw | GGGGACAAGTTTGTACAAAAA AGCAGGCTATGAATATT GCAATTGATGATGATGA<br>To pick up the gene from cDNA for over-expression (good for potato) | 30 |

TABLE 1-continued

Oligonucleotides used for construct production

| Name | Sequence 5' to 3'/ Description | SEQ ID NO. |
|---|---|---|
| GAME9-Pot GW Rv | GGGGACCACTTTGTACAAGAA AGCTGGGTTCATTTGTAT CAACATTTGTAAATTCACAC<br>To pick up the gene from cDNA for overexpression (good for potato) | 31 |

Co-Expression Analysis

The tomato GAME1 (Solyc07g043490) and its potato ortholog SGT1 (PGSC003DMG400011749) were used as 'baits' in the co-expression analysis, resulting in lists (sorted in descending order by r-value >0.8) of co-expressed genes (for each 'bait' separately). Two homologous genes were subsequently identified (Solyc12g006460 and PGSC0003DMG400024274 in tomato and potato, respectively), which were highly correlated with the "bait" genes (r-value >0.9 in both species). Those genes were identified as GLYCOALKALOID METABOLISM 4 (GAME4, WO 2012/095843). The GAME4 genes were further added as 'baits' to the previous (GAME1) co-expression analysis. The co-expression lists for GAME1 (SGT1) and GAME4 in both species were used to construct co-expression correlation network. The analysis was performed as follows: tomato RNAseq transcriptome data from different tissues and organs (flesh, peel, seeds, roots, leaves, buds, flowers, pollen) and developmental stages (25 experiments in total) (Itkin et al., 2011, ibid) and potato RNAseq transcriptome data from different tissues and organs (40 experiments in total) (US 2012/0159676), were used. First, an R script was used to perform co-expression analysis (for each species) and the list of co-expressed genes was constructed as a FASTA file, using a Perl script. Finally, BLASTall tools (Camacho C. et al., 2009. BMC Bioinform 10:421) were used to find shared homologs between the two species. The tblastx criteria for homolog similarity were set to p-value >0.05, minimum 25 nucleotides, and at least 60 percent similarity as an overall identity for each gene. The co-expression network was visualized with the Cytoscape program (Shannon P. et al., 2003. Genome Res. 13:2498-2504).

Phylogenetic Analysis

The protein sequences were aligned using the Muscle algorithm and the phylogenetic tree was analyzed and visualized by the SeaView v4.3.5 program using the maximum likelihood method by PhyML 3.0 (Exposito-Rodriguez M et al., 2008. BMC Plant Biol. 8:131) with the following settings: model—LG; The approximate likelihood ratio test (aLRT) Shimodaira-Hasegawa-like (SH-like) procedure was used as a statistical test to calculate branch support (branch support—aLRT (SH-like)); invariable sites—optimized; across site rate variation—optimized; tree searching operations—best for NNI & SPR; starting tree—BioNJ, optimize tree topology. The numbers on the branches indicate the fraction of bootstrap iterations supporting each node. The accession numbers of the proteins used for the preparation of this tree and the organism names are listed in Table 2 hereinbelow; the tree is presented in FIG. 12.

TABLE 2

Accession numbers of the sequences used for the construction of the phylogenetic tree

Figure 12:
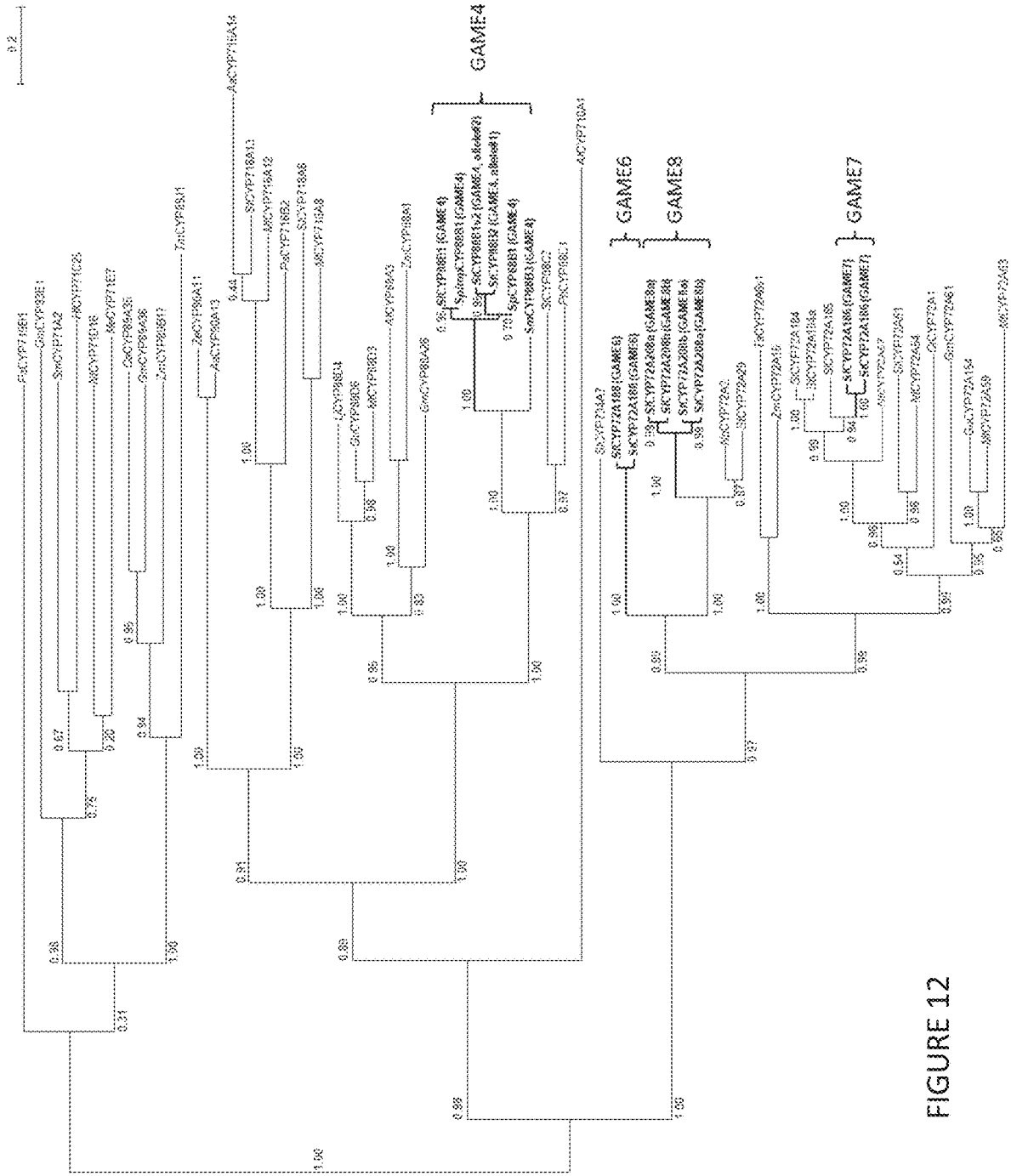
FIG. 12 shows the phylogenetic tree of GAME genes in the plant CYP450 protein family. The numbers on the branches indicate the fraction of bootstrap iterations supporting each node.

| Name as appears in FIG. 12 | Latin and common name | Accession number |
|---|---|---|
| GuCYP88D6 | Glycyrrhiza uralensis | BAG68929.1 |
| LjCYP88D4 | Lotus japonicus | BAG68927.1 |
| MtCYP88D3 | Medicago truncatula | BAG68926.1 |
| CmCYP88A2 | Cucurbita maxima | AF212991 |
| AtCYP88A3 | Arabidopsis thaliana | AAB71462.1 |
| PsCYP88A7 | Pisum sativum | AAO23064.1 |
| ZmCYP88A1 | Zea mays | NP_001105586.1 |
| GmCYP88A26 | Glycine max | XP_003516638.1 |
| CaCYP89A35 | Capsicum annuum | DQ114394 |
| GmCYP89A36 | Glycine max | DQ340245 |
| ZmCYP89B17 | Zea mays | CO465851.1 |
| TmCYP89J1 | Triticum monococcum | AY914081 |
| SlCYP88B1 (GAME4) | Solanum lycopersicum | Solyc12g006460.1.1 |
| SpimpCYP88B1 (GAME4) | Solanum pimpinellifolium | contig 6356779 |
| SpCYP88B1 (GAME4) | Solanum pinelii | AW618484.1, BG135958.1 |
| StCYP88B2 (GAME4) | Solanum tuberosum group Phureja | PGSC0003DMP400041994 |
| StCYP88B1v2 (GAME4) | Solanum tuberosum group Tuberosum | PGSC0003DMP400041994 |
| SlCYP88C2 | Solanum lycopersicum | Solyc10g007860.2.1 |
| SmCYP88B3 (GAME4) | Solanum melongena | FS071104, FS071103 |
| OsCYP90A3 | Oryza sativa | AC123526.1 |
| SlCYP90A5 | Solanum lycopersicum | Solyc06g051750.2.1 |
| ScCYP90A8 | Citrus sinensis | DQ001728.1 |
| ZeCYP90A11 | Zinnia elegans | BAE16977.1 |
| PhCYP88C1 | Petunia hybrida | AAZ39647.1 |
| AaCYP90A13 | Artemisia annua | ABC94481.1 |
| AtCYP710A1 | Arabidopsis thaliana | AAC26690.1 |
| SmCYP71A2 | Solanum melongena | X71654.1 |
| GmCYP93E1 | Glycine max | AB231332 |
| HlCYP71C25 | Hordeum lechleri | AY462228 |
| NtCYP71D16 | Nicotiana tabacum | AF166332 |
| MeCYP71E7 | Manihot esculenta | AY217351 |
| TaCYP71F1 | Triticum aestivum | AB036772 |
| AoCYP71J1 | Asparagus officinalis | AB052131 |
| MaCYP71N1v2 | Musa acuminata | AY062167 |
| TaCYP72A6v1 | Triticum aestivum | AF123604 |
| ZmCYP72A16 | Zea mays | AF465265 |
| LeCYP72A51 | Solanum lycopersicum | Solyc10g051020.1.1 |
| GmCYP72A61 | Glycine max | DQ340241 |
| MtCYP716A12 | Medicago truncatula | ABC59076.1 |
| StCYP716A13 | Solanum tuberosum | PGSC0003DMP400013378 |
| AaCYP716A14 | Artemisia annua | DQ363134 |
| PsCYP716B2 | Picea sitchensis | AY779543 |
| SlCYP718A6 | Solanum lycopersicum | Solyc07g055970.1.1 |
| MtCYP718A8 | Medicago truncatula | XP_003617455.1 |
| PsCYP719B1 | Papaver somniferum | EF451150 |
| StCYP72A186 (GAME7) | Solanum tuberosum | PGSC0003DMG402012386 |
| SlCYP72A186 (GAME7) | Solanum lycopersicum | Solyc07g062520 |
| SlCYP72A188 (GAME6) | Solanum lycopersicum | Solyc07g043460 |
| StCYP72A188 (GAME6) | Solanum tuberosum | PGSC0003DMG400011750 |
| GuCYP72A154 | Glycyrrhiza uralensis | BAL45206.1 |
| MtCYP72A59 | Medicago truncatula | ABC59078.1 |
| NtCYP72A57 | Nicotiana tabacum | ABC69414.1 |
| NtCYP72A54 | Nicotiana tabacum | ABC69417.1 |
| CrCYP72A1 | Catharanthus roseus | gi461812 |
| MtCYP72A63 | Medicago truncatula | gi371940452 |
| NpCYP72A2 | Nicotiana plumbaginifolia | AAB05376.3 |
| SlCYP734A7 | Solanum lycopersicum | Solyc03g120060.1.1 |
| StCYP72A29 | Solanum tuberosum | BAB86912.1 |
| StSYP72a56 | Solanum tuberosum | PGSC0003DMG400017325 |
| StCYP72A208 (GAME8a) | Solanum tuberosum | PGSC0003DMG400026594 |
| StCYP72A208 (GAME8b) | Solanum tuberosum | PGSC0003DMG400026586 |
| SlCYP72A208 (GAME8a) | Solanum lycopersicum | TC243022 |
| SlCYP72A208 (GAME8b) | Solanum lycopersicum | SGN-U578058 |

Metabolite Analysis

Preparation of plant tissue extracts and profiling of semipolar compounds (including steroidal alkaloids and steroidal saponins) by UPLC-qTOF-MS and phytosterol content of the tomato leaves were carried out as described previously (Itkin et al., 2011, supra).

Quantitative Real-Time PCR Assays

RNA was isolated and Quantitative Real-Time PCR was performed as described previously (Itkin et al., 2011, supra). In addition, the TIP41 gene (23) was used as an endogenous control for the potato samples. Oligonucleotides are listed in Table 1 hereinabove.

Production of Recombinant Enzyme

GAME2, GAME17 and GAME18 were amplified from cDNA and subcloned into pACYCDUET-1 using BamH I and Pst I (GAME2, GAME18) or BamHI and XhoI (GAME17) restriction sites, and the insert was verified by sequencing. The resulting plasmids, pAC-GAME2/17/18 were transformed to E. coli BL21 DE3. For expression of the GAME enzymes, fresh overnight cultures were diluted 1:100 in 25 ml 2xYT medium with 30 µg/ml chloramphenicol and incubated at 37° C. and 250 rpm until an $A_{600nm}$ of 0.4 was reached. Subsequently, IPTG was added to a concentration of 0.5 mM, and the incubation was continued overnight at 18° C. and 250 rpm. The next day, cells were harvested by centrifugation, and the pellet resuspended in 2 ml of 50 mM Tris HCl pH=7.0, 15% glycerol, 0.1 mM EDTA and 5 mM β-mercaptoethanol. After breaking the cells by sonication, insoluble material was removed by centrifugation, and the soluble fractions were used for characterization of the enzymes. Proteins were stored at −20° C. until further analysis.

Preparation of Substrates

For hydrolysis, 35 mg of α-tomatine was solved in 3 ml of 1N HCl, and was incubated for 15 min. at 100° C. Subsequently, the solution was put on ice, and $NH_3$ was added until the pH of the solution was 9.0. The solution was extracted with 4 ml water-saturated butanol. The butanol phase was evaporated to dryness under vacuum, the residual pellet solved in 1 ml methanol and stored at −20° C. until further use. The degradation products of α-tomatine were separated on a Luna 5 µm C18(2) 100 Å, LC Column 150×21.2 mm (Phenomenex, USA), using an isocratic elution with 25% acetonitrile in water and 0.1% formic acid. Compounds were detected using a 3100 Mass Detector (Waters), and collected. Fractions were freeze-dried, and purity of compounds was verified by LC-MS. For identification of products, liquid chromatography, coupled to quadrupole time-of-flight mass spectrometry (LC—QTOF-MS) was performed using a Waters Alliance 2795 HPLC connected to a Waters 2996 PDA detector and subsequently a QTOF Ultima V4.00.00 mass spectrometer (Waters, MS technologies, UK) operated in positive ionization mode. The column used was an analytical Luna 3 µm C18 (2) 100 Å; 150×2.0 mm (Phenomenex, USA) attached to a C18 pre-column (2.0×4 mm; AJO-4286; Phenomenex, USA). Degassed eluent A [ultra-pure water:formic acid (1000:1, v/v)] and eluent B [acetonitrile:formic acid (1000:1, v/v)] were used with flow rate of 0.19 ml/min. The gradient started at 5% B and increased linearly to 75% B in 45 min., after which the column was washed and equilibrated for 15 min. before the next injection. The injection volume was 5 µl. This procedure yielded several milligrams of pure γ-tomatine (tomatidine—galactoside—glucoside, T-Gal-Glu) and β1-tomatine (tomatidine—galactoside—diglucoside. T-Gal-Glu-Glu). Tomatidine galactoside (T-Gal) could not be purified in this way due to strong contamination with T-Gal-Glu. Therefore 5 mg tomatidine was incubated with GAME1 and UDP-galactose in 1 ml reaction mix, as described previously (Itkin et al., 2011, supra). T-Gal was purified from UDP-galactose by solid phase extraction. Waters OASIS HLB 3 cc columns (Waters Corp., Milford, MA) was conditioned with 6 mL 100% methanol followed by rinsing with 4 mL ultra-pure water. The reaction, supplemented with 10% methanol, was loaded and the cartridge was subsequently washed with 4 mL ultra-pure water. Compounds were eluted with 1 mL 75% methanol in ultra-pure water (v:v), and 0.4 mL 100% methanol. The solvent was removed from the combined eluate using a speed vacuum concentrator until a totally dry-pellet was obtained.

Enzyme Assays

The substrates T-Gal, β1- and γ-tomatine were dissolved to 1 mM in 50% DMSO. Enzyme assays were carried out in 50 mM Tris HCl pH=7.0 containing 5 mM β-mercaptoethanol using 5 µg/ml enzyme, 8 mM UDP-xylose and 0.02 mM substrate in a final reaction volume of 100 µl. After 2 h. of incubation under agitation at 37° C., reactions were stopped by addition of 300 µl methanol and 0.1% formic acid, and followed by brief vortexing and sonication for 15 min. Subsequently, the extracts were centrifuged for 5 min. at 13,000 rpm and filtered through 0.45 µm filters (Minisart SRP4, Biotech GmbH, Germany), and analyzed by LC-MS (see above). The amount of product was measured by the peak surface area in the LC-MS chromatogram, and compared to a control incubation in which an enzyme preparation of an E. coli harboring an empty pACYCDUET-1. Masses used for detection were α-tomatine ($C_{50}H_{83}N_{21}$; m/z=1034.55 ([M+H]+)), β1-tomatine T-Gal-Glu-Glu ($C_{45}H_{75}N_{17}$; m/z=902.51 ([M+H])), β2-tomatine ($C_{44}H_{73}N_{16}$; m/z=872.50 ([M+H]+)), γ-tomatine T-Gal-Glu ($C_{39}H_{65}N_{12}$; m/z=740.46 ([M+H])), and T-Gal ($C_{33}H_{55}N_{7}$; m/z=578.41 ([M+H])).

Virus Induced Gene Silencing (VIGS) Experiments

Vectors containing fragments of GAME genes were constructed and VIGS experiments were conducted as described previously (Orzaea D et al., 2009. Plant Physiol. 150:1122-1134; Li R et al., 2006 J. Mass Spec. 41:1-22). Plants infected with Agrobacterium, containing empty vector and helper vector pTRV1, were used as control. Oligonucleotides used to prepare the pTRV2_DR_GW vectors are listed in Table 1 hereinabove.

Genome Sequence Analysis of the Wild Tomato Species

Partial genomic data obtained by re-sequencing (Dr. Arnaud G. Bovy, unpublished data) of three tomato wild species genomes (i.e. *Solanum pennellii*, *S. pimpinellifolium* and *S. chmielewskii*) were analyzed for the presence or absence of sequences (contigs) that align to the SGAs biosynthesis gene clusters on tomato chromosomes 7 and 12. The TopHat toolkit (Trapnell C. 2012. Nat. Protoc. 7:562-578) was used for mapping reads of the wild species to the tomato genome (ITAG 2.4), as a reference genome. The mapped reads were visualized with the IGV genome browser (Robinson J T et al., 2011. Nat. Biotechnol. 29:24-26). In order to assemble and align the sequence of the contigs from the three wild species to the gene clusters on to the existing cultivated tomato sequences of chromosomes 7 and 12, a combination of the CLC workbench, CAP3BWA and SAMtools software packages and an in-house Perl script were used.

Example 1: Genes Associated with SGA Biosynthesis

To discover genes associated with SGA biosynthesis, a co-expression analysis using transcriptome data from tomato and potato plants was performed. Coexpression with GAME1/SGT1 (chromosome 7) and GAME4 (chromosome 12) as "baits" in either potato or tomato are presented in a form of a heatmap in Tables 3-6 herein below. Genes that are highly co-expressed with either GAME1/SGT1 (chromosome 7) or GAME4 (chromosome 12) are depicted with a large font and bold.

TABLE 3

Accession numbers, putative protein and co-expression r-values - tomato, chromosome 7

| Gene name | Putative protein | r-value of correlation with tomato GAME1 expression |
|---|---|---|
| Solyc07g043310 | Aminotransferase | −0.26 |
| Solyc07g043320 | Unknown Protein | 0.12 |
| Solyc07g043330 | GRAS family transcription factor | 0.72 |
| Solyc07g043340 | Unknown Protein | |
| Solyc07g043350 | Unknown Protein | |
| Solyc07g043360 | 60S ribosomal protein L27 | 0.10 |
| Solyc07g043370 | Transposase | |
| Solyc07g043380 | Unknown Protein | |
| Solyc07g043390 | Cellulose synthase family protein (GAME15) | 0.92 |
| Solyc07g043400 | Unknown Protein | |
| Solyc07g043410 | UDP-xylose xylosyltransferase (GAME2) | |
| Solyc07g043420 | 2-oxoglutarate-dependent dioxygenase | 0.79 |
| Solyc07g043430 | Gag-Pol polyprotein | |
| Solyc07g043440 | Glucosyltransferase-like protein | |
| Solyc07g043450 | Zeatin O-glucosyltransferase | |
| Solyc07g043460 | Cytochrome P450 (GAME 6) | 0.91 |
| Solyc07g043470 | Unknown Protein | |
| Solyc07g043480 | UDP-glucose glucosyltransferase | 0.88 |
| Solyc07g043490 | UDP-glucosyltransferase family 1 protein (GAME1) | 1.00 |
| Solyc07g043500 | UDP-glucosyltransferase | 0.95 |
| Solyc07g043510 | Cysteine-type peptidase | −0.24 |
| Solyc07g043520 | transposase | |
| Solyc07g043530 | Unknown Protein | |
| Solyc07g043540 | Unknown Protein | |
| Solyc07g043550 | UDP-arabinose 4-epimerase | 0.70 |
| Solyc07g043560 | Heat shock protein 4 | 0.24 |
| Solyc07g043570 | Aldo/keto reductase family protein | −0.09 |
| Solyc07g043580 | BHLH transcription factor | 0.43 |
| Solyc07g043590 | Amine oxidase family protein | 0.03 |
| Solyc07g043600 | Pentatricopeptide repeat-containing protein | 0.43 |
| Solyc07g043610 | Auxin response factor 6 | |
| Solyc07g043620 | Auxin response factor 6-1 | 0.65 |
| Solyc07g043630 | Acyl-CoA synthetase/AMP-acid ligase II | |
| Solyc07g043640 | Acyl-CoA synthetase/AMP-acid ligase II | |
| Solyc07g043650 | AMP-dependent synthetase and ligase | |
| Solyc07g043660 | Acyl-CoA synthetase/AMP-acid ligase II | −0.16 |
| Solyc07g043670 | Hydroxycinnamoyl CoA quinate transferase 2 | |
| Solyc07g043680 | Enoyl-CoA-hydratase | |
| Solyc07g043690 | Enoyl-CoA-hydratase | |
| Solyc07g043700 | Acyltransferase | |

TABLE 4

Accession numbers, putative protein and co-expression r-values - potato, chromosome 7

| Gene name | Putative protein | r-value of correlation with potato SGT1 expression |
|---|---|---|
| PGSC0003DMG400011754 | Gamma aminobutyrate transaminase | −0.31 |
| PGSC0003DMG400011753 | Uro-adherence factor A | −0.40 |
| PGSC0003DMG400011742 | DELLA protein RGA | 0.15 |
| PGSC0003DMG400011741 | 60S ribosomal protein L27 | 0.43 |
| PGSC0003DMG400039612 | Conserved gene of unknown function | |
| PGSC0003DMG400011752 | Cellulose synthase (GAME15) | 0.90 |
| PGSC0003DMG400011740 | beta-solanine rhamnosyl-transferase (SGT3) | 0.90 |
| PGSC0003DMG400011751 | 2-oxoglutarate-dependent dioxygenase | 0.87 |
| PGSC0003DMG400011750 | Cytochrome P-450 (GAME 6) | 0.92 |
| PGSC0003DMG400044993 | Unknown Protein | |
| PGSC0003DMG400011749 | solanidine galactosyl-transferase (SGT1) | 1.00 |
| PGSC0003DMG402015928 | OTU-like cysteine protease family protein | −0.24 |
| PGSC0003DMG401015928 | Conserved protein of unknown function | −0.25 |
| PGSC0003DMG400015927 | UDP-arabinose 4-epimerase 1 | −0.21 |
| PGSC0003DMG400015920 | Heat shock 70 kDa protein | −0.17 |
| PGSC0003DMG402015926 | Aldo/keto reductase | −0.05 |
| PGSC0003DMG401015926 | Isoform 2 of Transcription factor PIF5 | −0.33 |
| PGSC0003DMG400015925 | Amine oxidase | 0.11 |
| PGSC0003DMG400015924 | Pentatricopeptide repeat-containing protein | 0.32 |
| PGSC0003DMG400015919 | ARF8 | 0.07 |
| PGSC0003DMG400036440 | AMP dependent ligase | |
| PGSC0003DMG400015923 | Acyl:coA ligase acetate-coA synthetase | |
| PGSC0003DMG400015922 | Acyl:coA ligase acetate-coA synthetase | |
| PGSC0003DMG400044288 | Acyltransferase | |
| PGSC0003DMG400015918 | Acyltransferase | 0.03 |

TABLE 5

Accession numbers, putative protein and co-expression r-values - tomato, chromosome 12

| Gene name | Putative protein | r-value of correlation with tomato GAME4 expression |
|---|---|---|
| Solyc12g006530 | Cycloartenol synthase | 0.08 |
| Solyc12g006520 | Cycloartenol synthase | 0.05 |
| Solyc12g006510 | Cycloartenol Synthase | −0.12 |
| Solyc12g006500 | Phosphate translocator protein | 0.15 |
| Solyc12g006490 | Beta-1-3-galaclosyl-o-glycosyl-glycoprotein | 0.03 |
| Solyc12g006480 | Nup205 protein | 0.35 |
| Solyc12g006470 | gamma-aminobutyrate Amino-transferase-like protein | 0.94 |
| Solyc12g006460 | Cytochrome P450 (GAME 4) | 1.00 |
| Solyc12g006450 | gamma-aminobutyrate Amino-transferase-like protein | −0.13 |
| Solyc12g006440 | Unknown Protein | 0.25 |
| Solyc12g006430 | UDP-glucuronosyltransferase 1-1 82A1 | |
| Solyc12g006420 | Topoisomerase II-associated protein PAT1 | 0.08 |
| Solyc12g006410 | UDP-arabinse 4-epimerase | |
| Solyc12g006400 | Unknown Protein | |
| Solyc12g006390 | 2-oxoglutarate-dependent dioxygenase | |
| Solyc12g006380 | 2-oxoglutarate-dependent dioxygenase | 0.15 |
| Solyc12g006370 | Amine oxidase family protein | −0.16 |
| Solyc12g006360 | Multidrug resistance protein mdtK | |
| Solyc12g006350 | Auxin response factor 6 | 0.35 |

TABLE 5-continued

Accession numbers, putative protein and co-expression r-values - tomato, chromosome 12

| Gene name | Putative protein | r-value of correlation with tomato GAME4 expression |
|---|---|---|
| Solyc12g006340 | Auxin response factor 6 | 0.47 |
| Solyc12g006330 | Acyltransferase-like protein | |
| Solyc12g006320 | ATP-dependent RNA helicase | 0.14 |
| Solyc12g006310 | Endoplasmic reticulum-Golgi | 0.25 |
| Solyc12g006300 | WD-repeat protein-like | −0.03 |
| Solyc12g006290 | Reticulon family protein | 0.19 |
| Solyc12g006280 | Myb-like DNA-binding protein | |

TABLE 6

Accession numbers, putative protein and co-expression r-values - potato, chromosome 12

| Gene name | Putative protein | r-value of correlation with potato GAME4 expression |
|---|---|---|
| PGSC0003DMG400020034 | Beta-amyrin synthase | −0.13 |
| PGSC0003DMG400024276 | Beta-Amyrin Synthase | −0.09 |
| PGSC0003DMG400024277 | Gene of unknown function | 0.10 |
| PGSC0003DMG400024278 | Phenylacetaldehyde synthase | 0.10 |
| PGSC0003DMG400024279 | Conserved gene of unknown function | −0.16 |
| PGSC0003DMG400024280 | Triose phosphate/phosphate translocator, non-green plastid, chloroplast | −0.06 |
| PGSC0003DMG400024271 | Acetylglucosaminyl-transferase | −0.06 |
| PGSC0003DMG400024273 | Resistance protein PSH-RGH6 | 0.37 |
| PGSC0003DMG400024281 | Gamma aminobutyrate transaminase isoform2 | 0.94 |
| PGSC0003DMG400024274 | Cytochrome P450 monooxygenase GAME4 | 1.00 |
| PGSC0003DMG400024275 | Gamma aminobutyrate transaminase isoform3 | 0.37 |
| PGSC0003DMG400024282 | Fortune-1 | 0.36 |
| PGSC0003DMG400028806 | UDP-glycosyltransferase 82A1-like | −0.18 |
| PGSC0003DMG401028807 | Topoisomerase II-associated protein PAT1 | |
| PGSC0003DMG402028807 | UDP-arabinse 4-epimerase | |
| PGSC0003DMG400028824 | Gene of unknown function | |
| PGSC0003DMG400028808 | 2-oxoglutarate-dependent dioxygenase | −0.07 |
| PGSC0003DMG400028809 | 2-oxoglutarate-dependent dioxygenase | 0.61 |
| PGSC0003DMG400028810 | Amine oxidase | −0.04 |
| PGSC0003DMG400028825 | MATE transporter | |
| PGSC0003DMG400028826 | Auxin response factor 6 | |
| PGSC0003DMG400043090 | Integrase core domain containing protein | |
| PGSC0003DMG400037700 | WRKY transcription factor 27 | |
| PGSC0003DMG400028811 | Acyltransferase | |

TABLE 6-continued

Accession numbers, putative protein and co-expression r-values - potato, chromosome 12

| Gene name | Putative protein | r-value of correlation with potato GAME4 expression |
|---|---|---|
| PGSC0003DMG400028812 | DEAD-box ATP-dependent RNA helicase 53 | 0.56 |
| PGSC0003DMG400028814 | WD-repeat protein | −0.10 |
| PGSC0003DMG401028829 | Polygalacturonase | |
| PGSC0003DMG400028815 | Rebellion family protein | 0.08 |
| PGSC0003DMG400028830 | Myb-like DNA-binding domain, SHAQKYF class family protein | |

Figure 2:
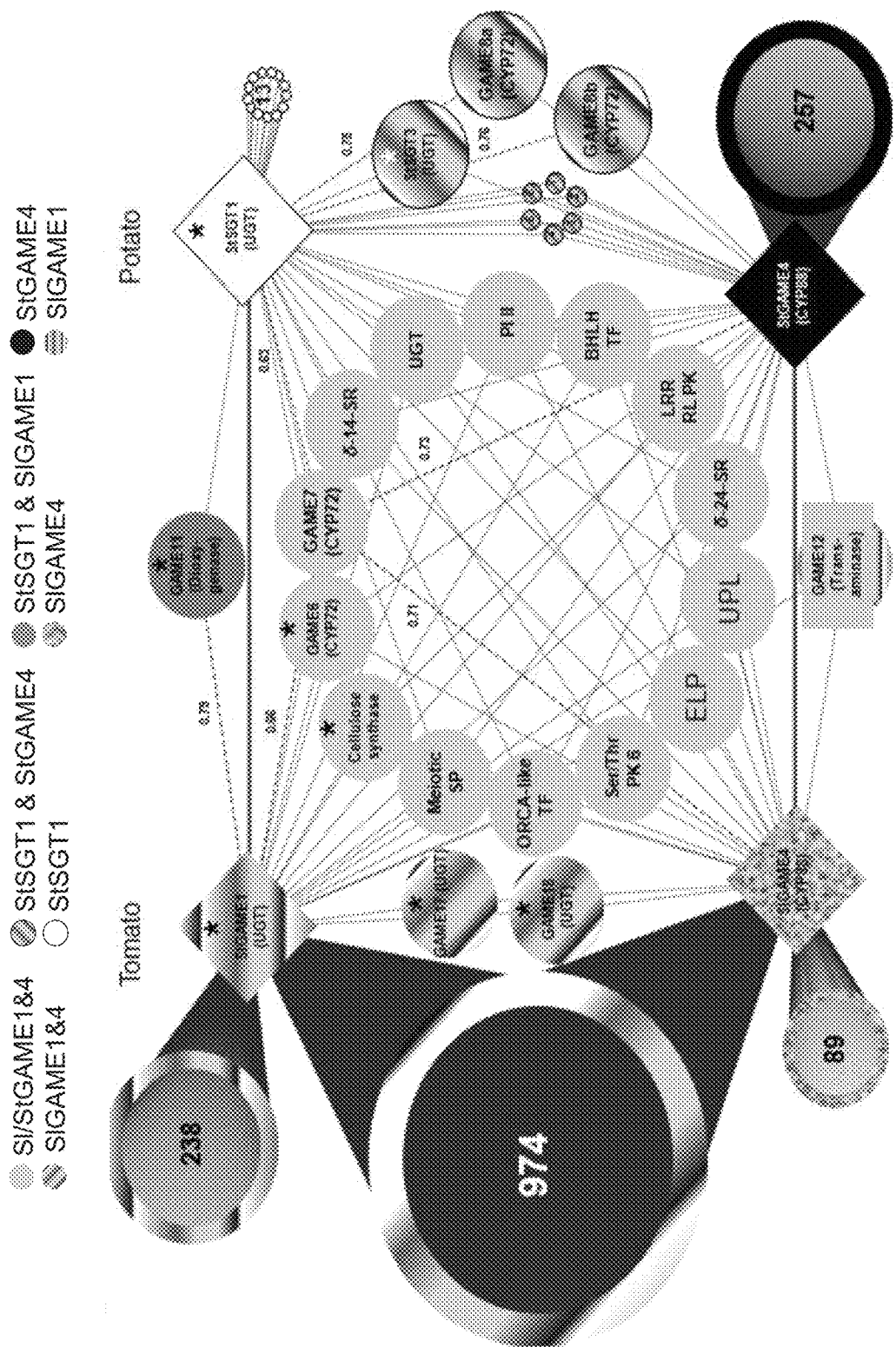
Figure 3:
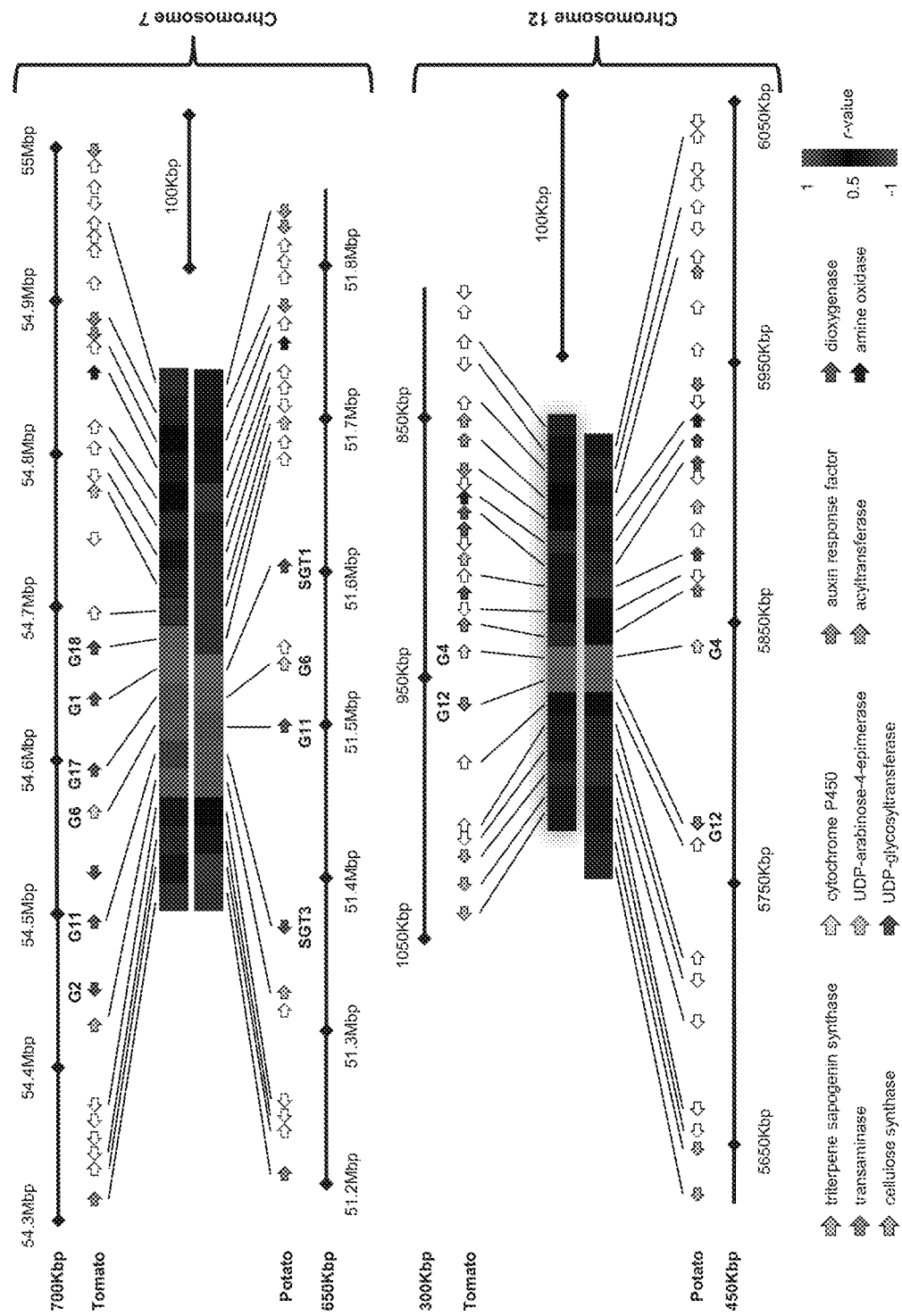
FIG. 3 presents schematic map of genes identified in the duplicated genomic regions in tomato and potato and their coexpression. Coexpression with GAME1/SGT1 (chromosome 7) and GAME4 (chromosome 12) as baits in either potato or tomato are presented in a form of a heatmap (Tables 3-6). Specific gene families are indicated by dark arrows while members of other gene families are in white arrows.

Sixteen genes from each species were co-expressed with GAME1/SGT1 (Table 7, FIG. 2). One of these genes, previously designated GLYCOALKALOID METABOLISM 4 (GAME4), encodes a member of the 88D subfamily of cytochrome P450 proteins (FIG. 3). GAME4 and GAME1/SGT1 display a very similar expression profile in tomato and potato (WO 2010/095843). The GAME1/SGT1 and GAME4 genes in tomato and potato are positioned in chromosomes 7 and 12 such that they are physically next to several of their co-expressed genes (FIG. 2).

A cluster of GAME1/SGT1 co-expressed genes spans a ~200Kbp genomic region on chromosome seven. Together with GAME1, the tomato cluster is composed of 7 co-expressed genes. These include 3 UDP-glycosyltransferases [GAME2 (termed SGT3 in potato); GAME17 and GAME18], a cytochrome P450 of the 72A subfamily (GAME6), a 2-oxoglutarate-dependent dioxygenase (GAME11), and a cellulose synthase-like protein (GAME15). It appears that in potato this cluster contains 5 co-expressed genes as it lacks homologs of the tomato genes encoding GAME17 and GAME18 UDP-glycosyltransferases. Enzyme activity assays were performed with the four recombinant clustered tomato UDP-glycosyltransferases. GAME17 and GAME18 exhibited UDP-glucosyltransferase activity when incubated with tomatidine galactoside (T-Gal) and γ-tomatine (T-Gal-Glu) as a substrate, respectively, whereas GAME2 was shown to have an UDP-xylosyltransferase activity when incubated with β1-tomatine (T-Gal-Glu-Glu) as a substrate (FIGS. 4E, 4F, and 4G). GAME1 was previously shown to act as a tomatidine UDP-galactosyltransferase in tomato (Itkin et al., 2011, supra). When incubating the 4 recombinant UGT enzymes in a single test tube, with tomatidine, and all glycoside donors (UDP-galactose, -glucose and -xylose), the accumulation of the final SGA product α-tomatine was observed (FIG. 4H).

Two genes encoding putative transcription factors were identified among the genes co-expressed with GAME1/SGT1 and GAME4 (FIGS. 4A-4H): one gene, designated GAME9, was identified by the tomato ID Solyc01g090340 and by the potato ID PGSC0003DMG400025989. It is described as ethylene-responsive element binding factor 13 and contains a putative AP2 domain. The other gene is the BHLH-transcription factor, identified by the tomato ID Solyc03g046570 and by the potato ID PGSC0003DMG400012262.

TABLE 7

Details of homologs co-expressed with known and putative steroidal alkaloid-associated genes in both potato and tomato presented in FIG. 2

| Name | Tomato ID Solyc | Potato reads | Tomato ID |
|---|---|---|---|
| Extensin-like protein | Solyc01g006400 | PGSC0003DMG400023230 | TCONS_00007692 |
| GAME 9 | Solyc01g090340 | PGSC0003DMG400025989 | TCONS_00011729 |
| Delta (24)-sterol reductase-like | Solyc02g069490 | PGSC0003DMG400021142 | TCONS_00044548 |

TABLE 7-continued

Details of homologs co-expressed with known and putative steroidal alkaloid-
associated genes in both potato and tomato presented in FIG. 2

| Name | Tomato ID Solyc | Potato reads | Tomato ID |
|---|---|---|---|
| BHLH transcription factor | Solyc03g046570 | PGSC0003DMG400012262 | TCONS_00055879 |
| LRR receptor-like protein kinase | Solyc05g009100 | PGSC0003DMG400014576 | TCONS_00101281 |
| Glycosyltransferase | Solyc05g053120 | PGSC0003DMG402027210 | TCONS_00100675 |
| Cellulose synthase-like (GAME15) | Solyc07g043390 | PGSC0003DMG400011752 | TCONS_00135034 |
| GAME6 (CYP72) | Solyc07g043460 | PGSC0003DMG400011750 | TCONS_00137734 |
| GAME1 (Galactosyltransferase) | Solyc07g043490 | PGSC0003DMG400011749 | TCONS_00133014 |
| GAME7 (CYP72) | Solyc07g062520 (GAME1 r-value 0.66; GAME4 r-value 0.71) | PGSC0003DMG402012386 (SGT1 r-value 0.63; GAME4 r-value 0.73 ) | TCONS_00132326 |
| Srt/Thr protein kinase 6 | Solyc08g066050 | PGSC0003DMG400025461 | TCONS_00151251 |
| Meiotic serine proteinase | Solyc08g077860 | PGSC0003DMG401012339 | TCONS_00149157 |
| Sterol reductase | Solyc09g009040 | PGSC0003DMG400002720 | TCONS_00162820 |
| Ubiquitin protein ligase | Solyc10g008410 | PGSC0003DMG400021683 | TCONS_00183263 |
| Proteinase inhibitor II | Solyc11g020960 | PGSC0003DMG402003479 | TCONS_00194999 |
| GAME4 (CYP88) | Solyc12g006460 | PGSC0003DMG400024274 | TCONS_00210154 |
| Gamma-aminobutyrate Aminotransferase-like protein (transaminase) (GAME12) | Solyc12g006470 | PGSC0003DMG400024281 | |
| Beta-solanine rhamnosyltransferase (SGT3) | #N/A | PGSC0003DMG400011740 | |
| 2-oxoglutarate-dependent dioxygenase (GAME11) | Solyc07g043420 | PGSC0003DMG400011751 | |
| GAME18 (Glycosyltransferase) | Solyc07g043500 | #N/A | |
| GAME17 (Glycosyltransferase) | Solyc07g043480 | #N/A | |

Tomato and potato sequences were obtained from Sol Genomics Network (solgenomics.net).
r-value for co-expression ≥0.8.
TCON number, a contig reference name given by the inventors in the assembly of RNAsec data.
N/A, not available.

Example 2: Functional Analysis of
GAME9-Transcription Factor

GAME9-silencing (RNAi) and overexpressing (OX) constructs were created by introducing the corresponding GAME9 DNA fragments to pK7GWIWG2(II) and pJCV52 binary vectors, respectively. Transgenic tomato and potato lines transformed with the respective GAME9 silencing and overexpressing constructs were generated as previously described (Itkin et al., 2011, supra). Tissue extracts were prepared and analyzed as described in Itkin et al. (2011, supra).

Figure 5B:
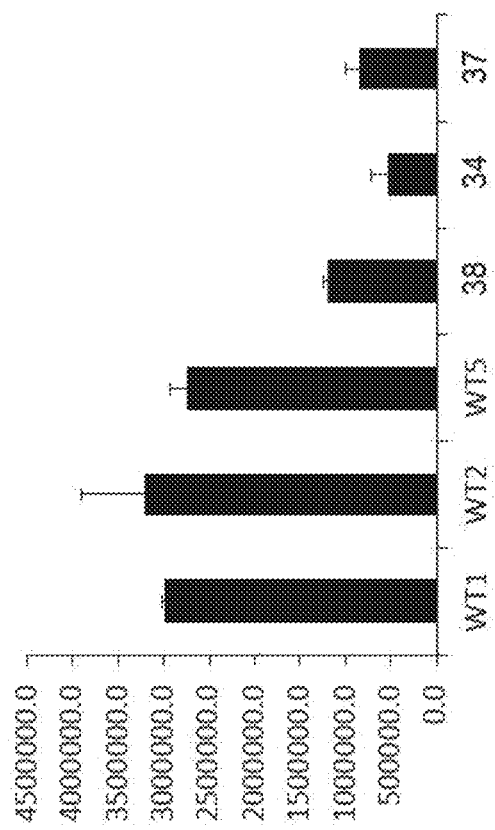
FIGS. 5A-5D show solanine/chaconine levels in peels of tuber of potato plant lines with altered expression of GAME9 compared to wild type plants. Solanine (FIG. 5A) and chaconine (FIG. 5B) level in tubers of GAME9 silenced plant; Solanine (FIG. 5C) and chaconine (FIG. 5D) levels in tubers of GAME9 overexpressing plants.
Figure 5D:
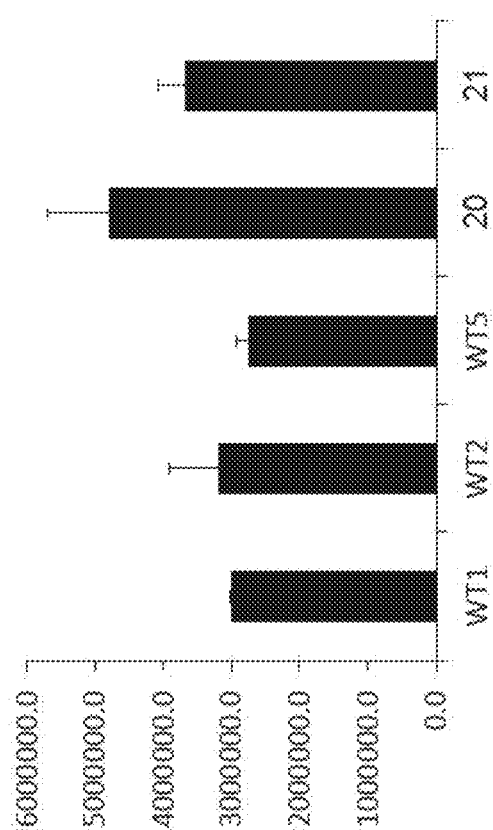
Figure 5A:
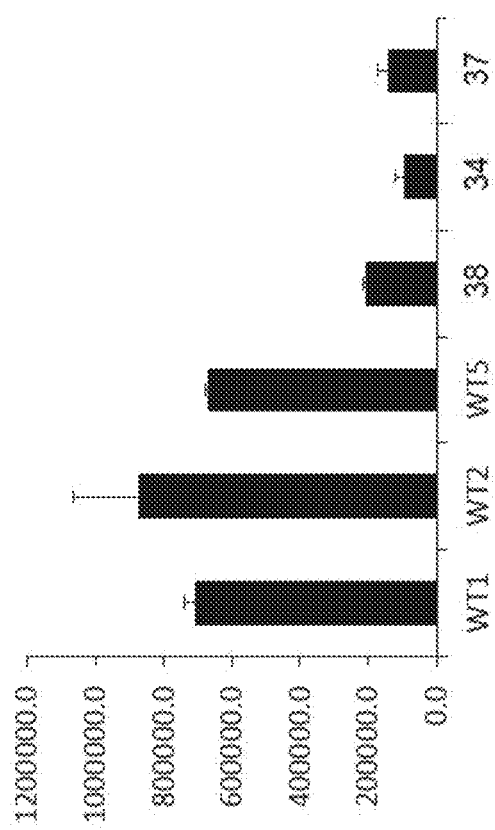
Figure 5C:
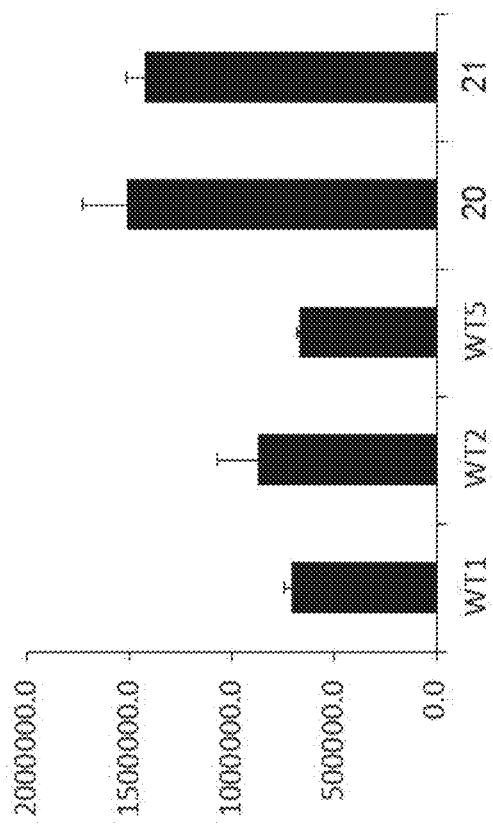
Figure 6:
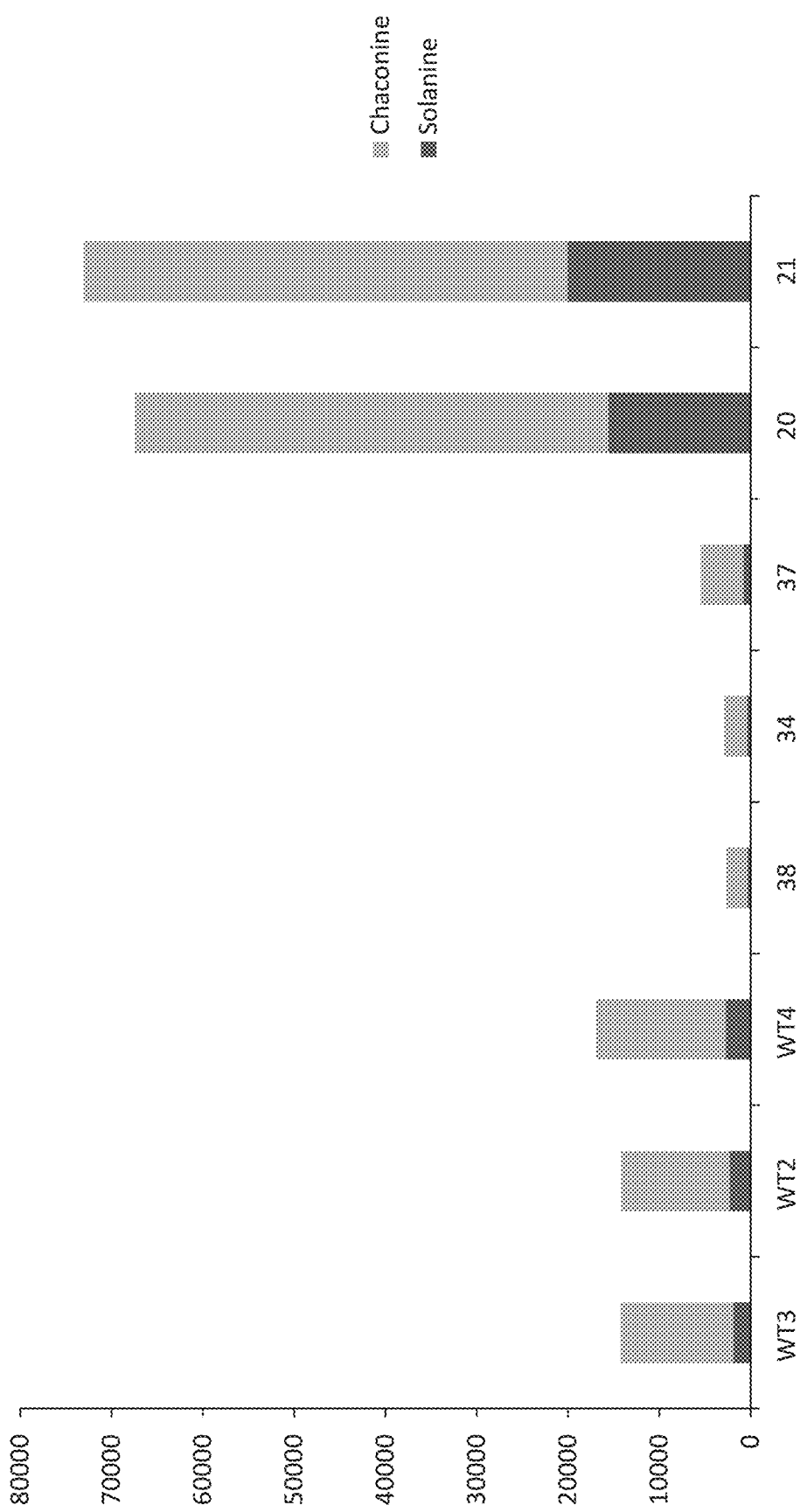
FIG. 6 shows solanine/chaconine levels in leaves of potato plant lines with either silenced (RNAi) or overexpressed (OX) GAME9 compared to wild type plants.
Figure 7:
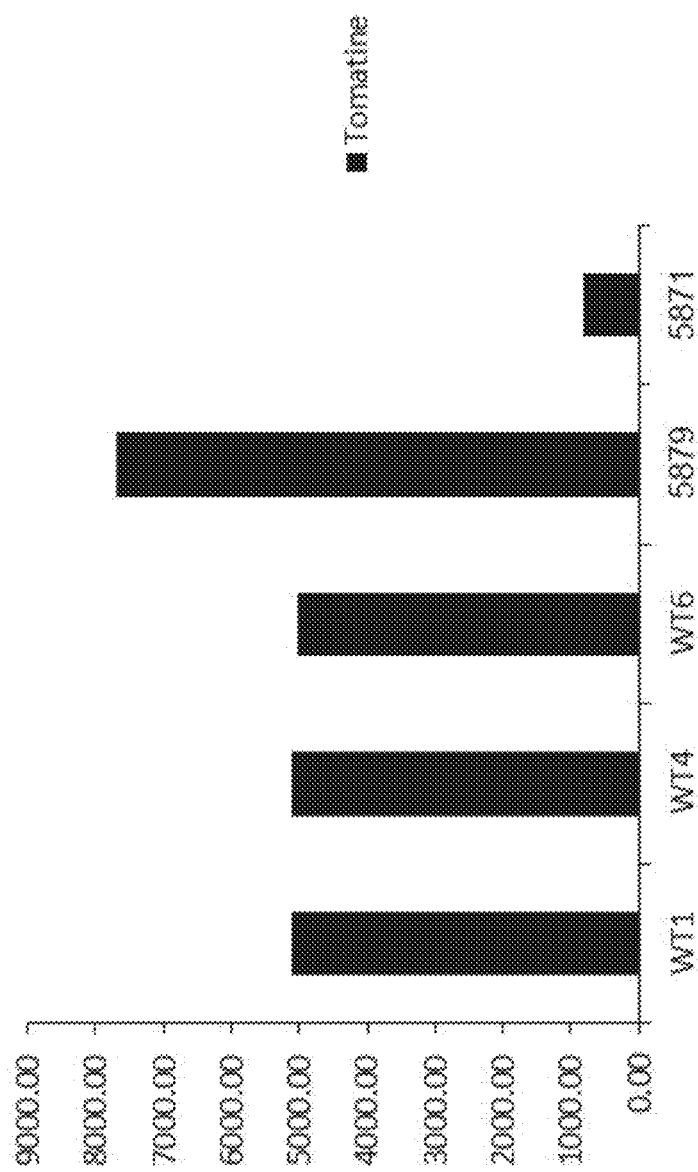
FIG. 7 shows tomatine levels in leaves of tomato plant lines with either silenced (RNAi, line 5871) or overexpressed (OX, line 5879) GAME9 compared to wild type plants.

The metabolic profiling of steroidal alkaloids using UPLC-TQ-MS was performed on extracts obtained from leaves and/or tubers of transgenic and wild type tomato and/or potato plants. In extract obtained from potato tuber peels of potato lines in which the gene encoding GAME9 was silenced (GAME9-RNAi lines) a reduction in α-solanine and α-chaconine was observed (FIGS. 5A and 5B, respectively). Leaves from potato GAME9-overexpression lines contained higher levels of α-solanine (FIG. 5C) and α-chaconine (FIG. 5D) compared to the wild type. A similar accumulation pattern was observed in potato leaves, having reduced amounts of α-chaconine and α-solanine in RNAi lines and increased amounts of these steroidal alkaloids in lines overexpressing the GAME9-transcription factor (FIG. 6).

In tomato, leaves extract of a line overexpressing the GAME9-transcription factor (designated 5879) contained higher levels of α-tomatine compared to its amount in leaf extract obtained from wild type plants. On the contrary, down regulation of the expression of GAME9-transcription factor (line 5871) resulted in significant reduction of α-tomatine content.

Example 3: Functional Characterization of the
GAME Genes

GAME11 Silenced Plants
Virus induced gene silencing (VIGS) is a commonly used technique allowing systemic silencing of genes in various organs of the plant (Dinesh-Kumar S P et al., 2003. Methods Mol Biol 236:287-294).

Analysis of tomato leaves with VIGS-silenced GAME11, a putative dioxygenase in the cluster, revealed a significant reduction in α-tomatine levels and accumulation of several cholestanol-type steroidal saponins.

Figure 8D:
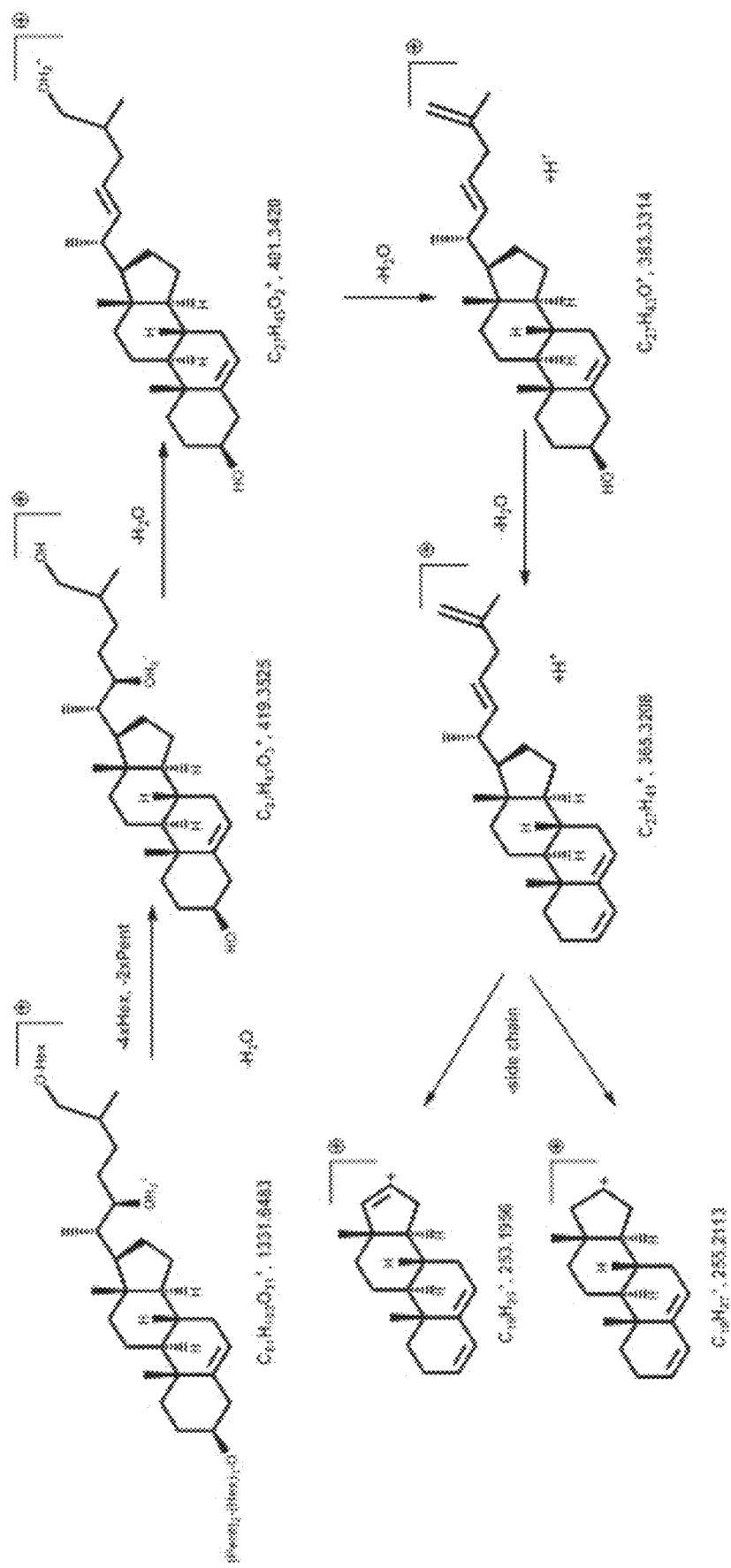

Silencing of GAME11 dioxygenase in tomato results in depletion of α-tomatine levels in leaves (m/z=1034.5) (FIG. 8A) while accumulating cholestanol-type steroidal saponins [i.e. STSs; m/z=1331.6, 1333.6, 1199.6, 1201.6 (major saponins)] (FIG. 8B). FIG. 8C shows MS/MS spectrum of m/z=1331.6 (at 19.28 min.). FIG. 8D shows the fragmentation patterns of the saponin eluted at 19.28 min. and accumulating in GAME11-silenced leaves. The corresponding mass signals are marked with an asterisk on the MS/MS chromatogram in FIG. 8C. The elemental composition and fragmentation patterns show that the compounds are cholestanol-type saponins, lacking one hydroxy-group and the E-ring (in comparison to furostanol-type saponins), which results in fragmentation, involving multiple losses of water molecules instead of tautomerisation and McLafferty rearrangement of the E-ring.

GAME18 Silenced Plants
The role of GAME18 in creating the tetrasaccharide moiety of α-tomatine was supported by Virus Induced Gene Silencing (VIGS) assays as GAME18-silenced fruit accumulated γ-tomatine which was not present in the control sample (FIGS. 9A-9E).

Figure 9A:
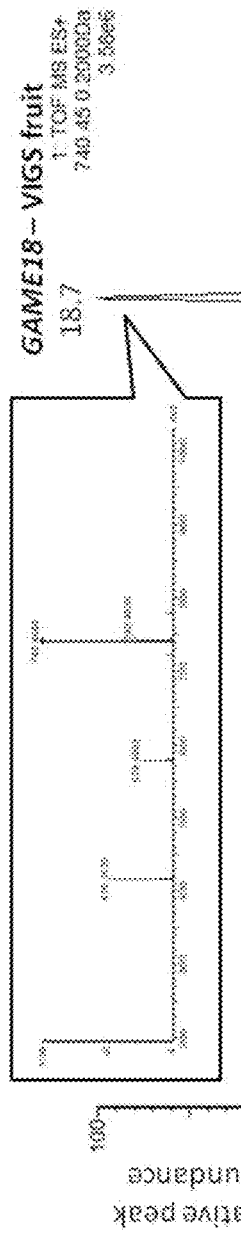
FIGS. 9A-9E show metabolites extracted from GAME18-silenced mature green tomato fruit. Peaks of newly accumulating compounds corresponding to the γ-tomatine standard (m/z=740.5) (FIGS. 9A-9C), and γ-tomatine pentoside (m/z=872.5) (FIGS. 9D-9E) are shown.
Figure 9B:
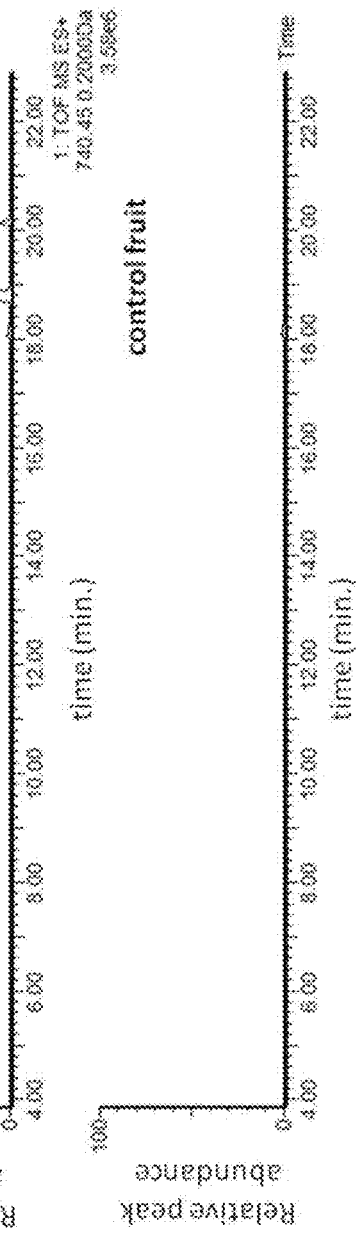
Figure 9C:
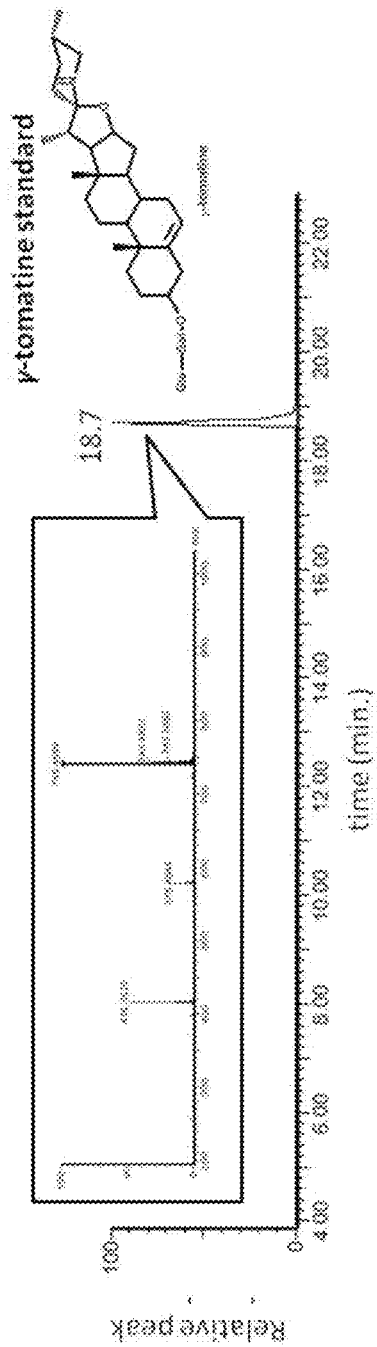
Figures 9D, 9E:
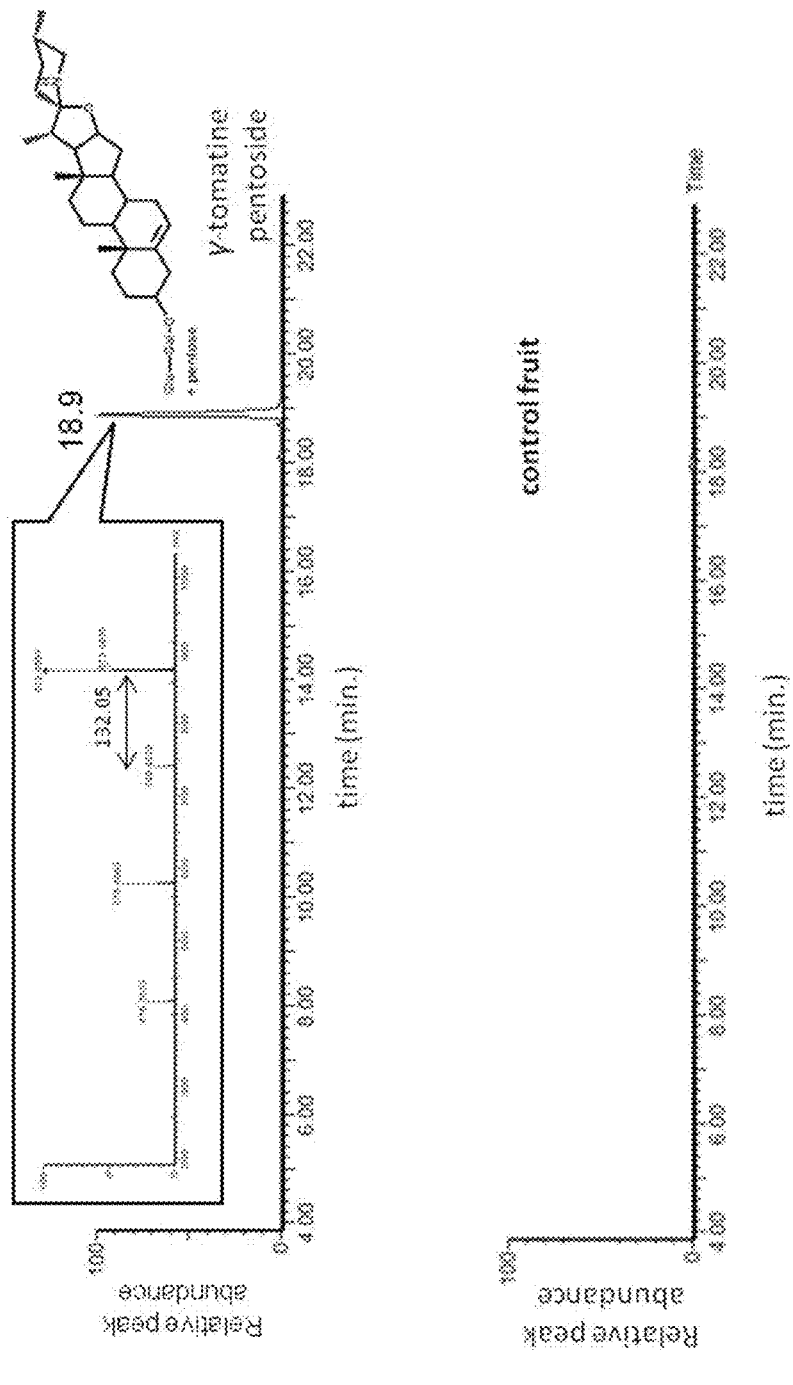

Among the metabolites extracted from GAME18-silenced mature green fruit, peaks of newly accumulating compounds were detected, corresponding to the γ-tomatine standard (m/z=740.5) (FIGS. 9A-C), and γ-tomatine pentoside (m/z=872.5) (FIGS. 9D-9E).

Figure 4B:
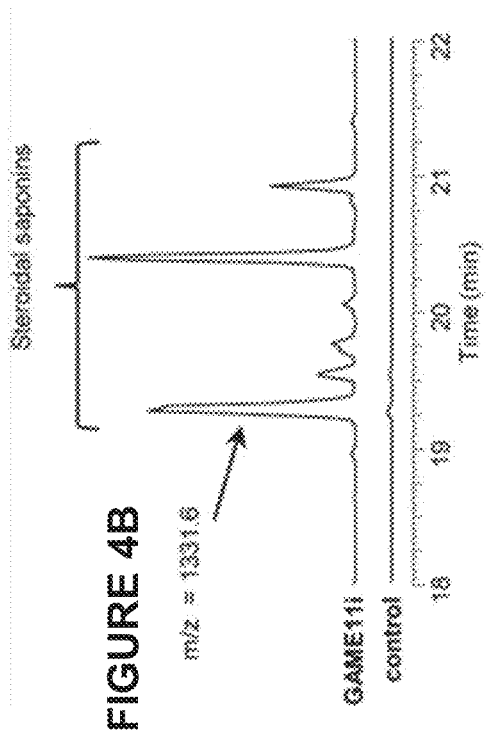
FIGS. 4A-4H shows functional analysis of tomato GAME genes.
Figure 4D:
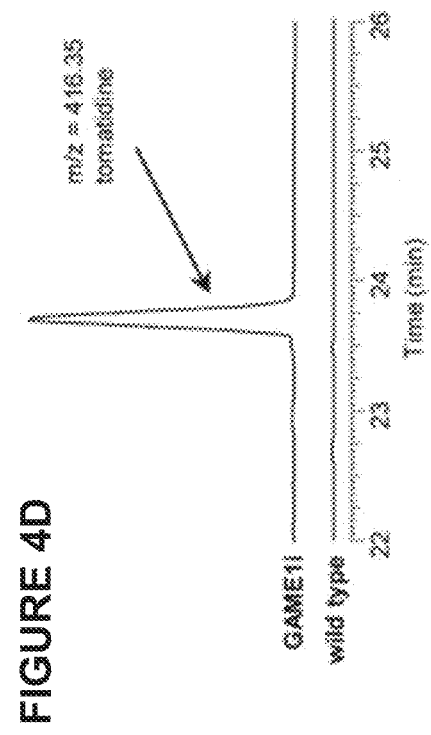
Figure 4A:
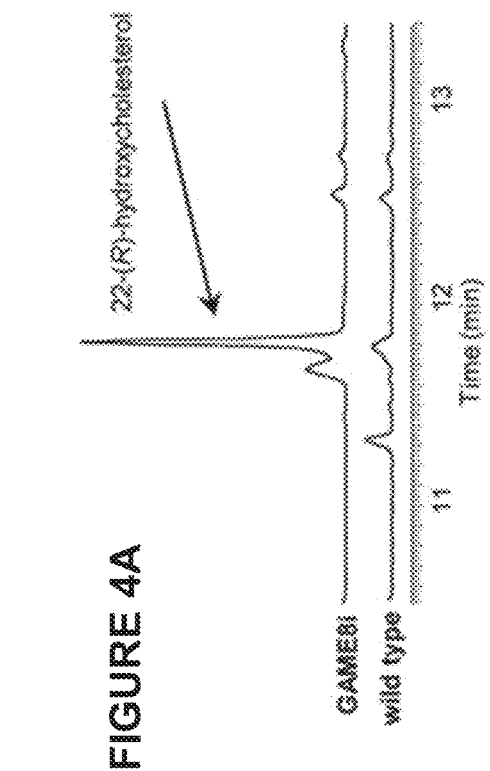
Figure 4C:
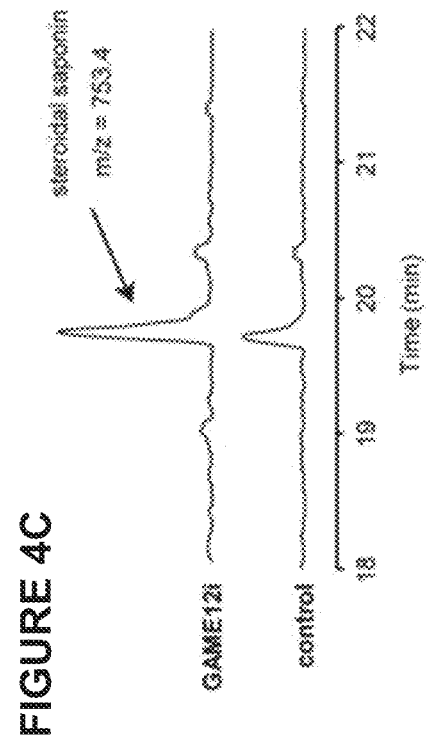
Figure 4F:
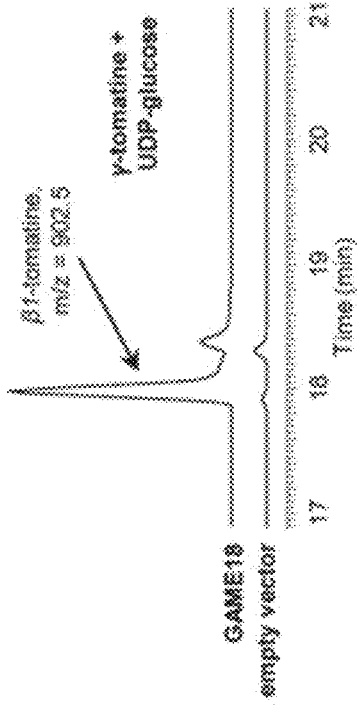
Figure 4E:
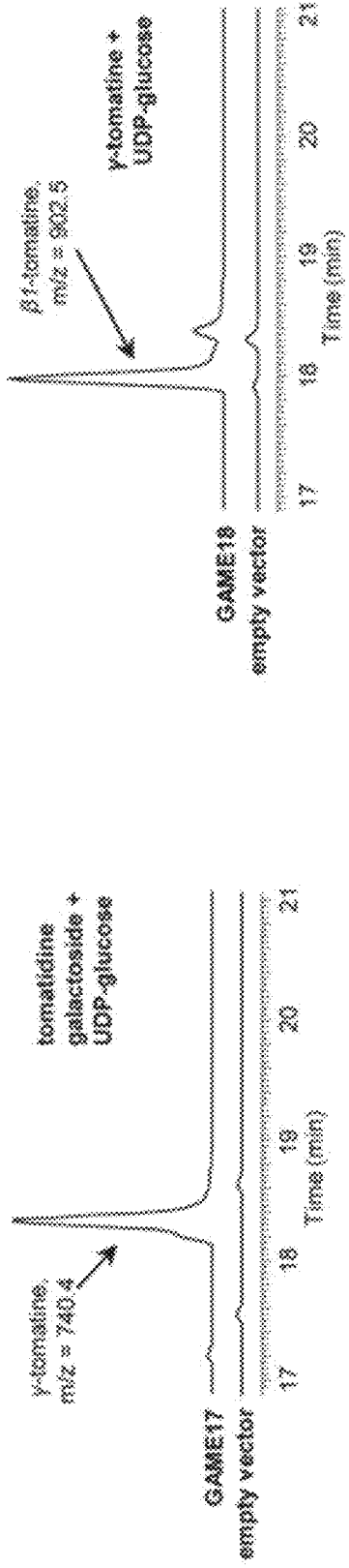
Figure 4H:
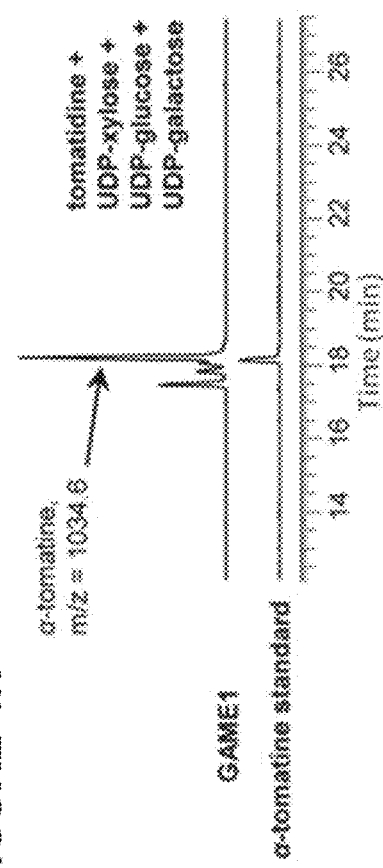
Figure 4G:
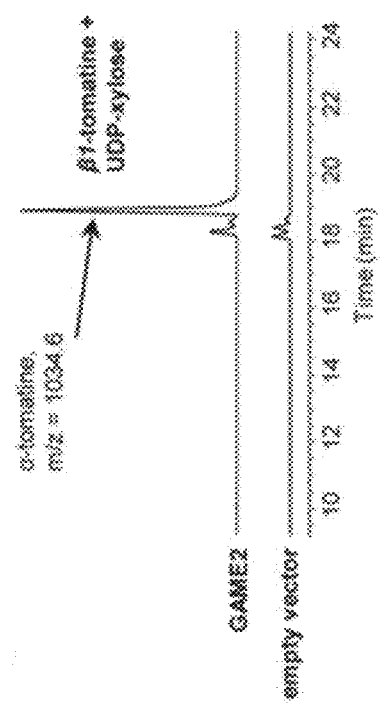
Figure 10A:
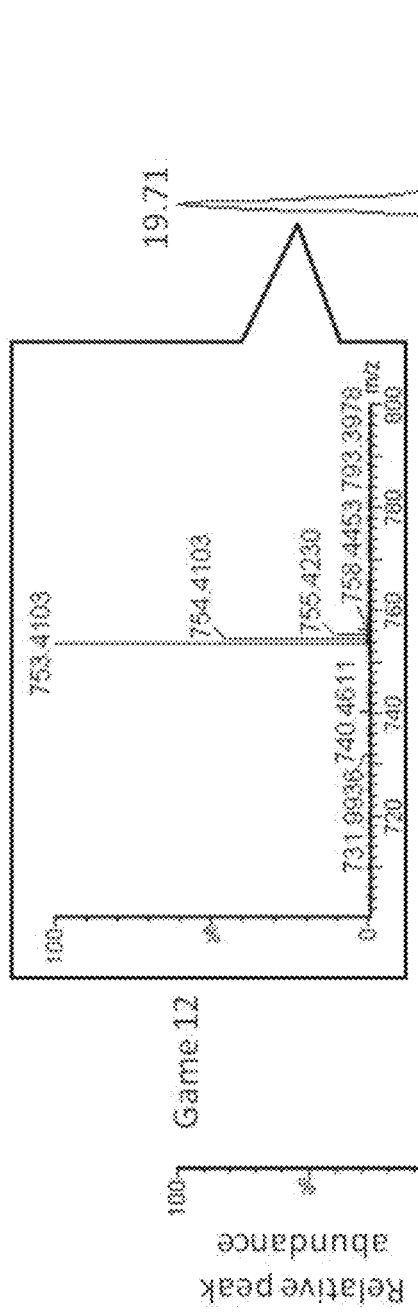
FIGS. 10A-10D show the effect of silencing of GAME12 transaminase in tomato.
Figure 10B:
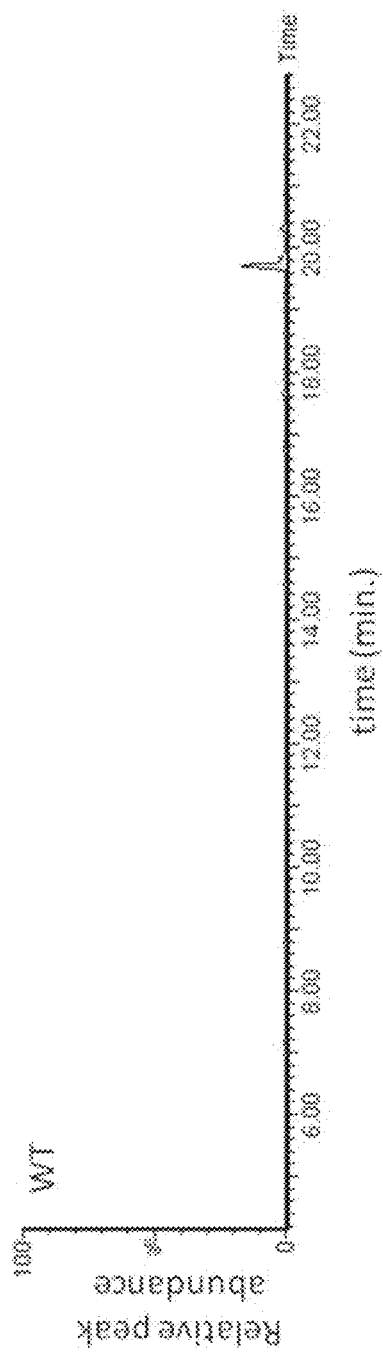
Figures 10C, 10D:
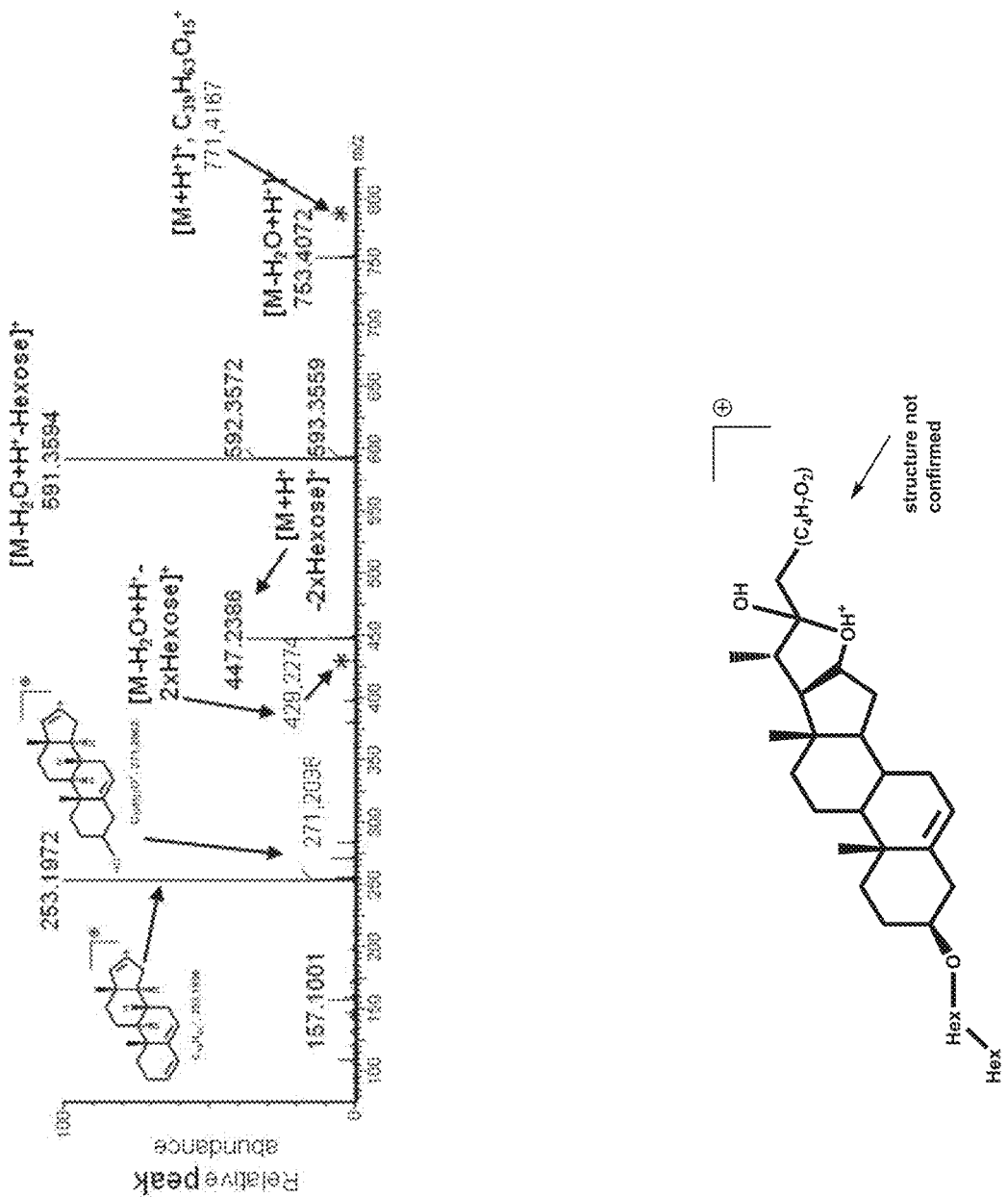

GAME12 Silenced Plants
Silencing of GAME12 transaminase in tomato resulted in accumulation of a furastanol-type steroidal saponin (FIG. 4D). FIG. 10A shows that GAME12-silenced leaves accumulate an STS (m/z=753.4), while it exists in only minor quantities in wild type leaf FIG. 10B. FIG. 10C shows MS/MS spectrum of m/z=753.4 at 19.71 min. with interpretation of the fragments. Suggested structure of the STS at 19.71 min. is depicted in FIG. 10D, concluded from the characteristic mass fragments observed in the MS/MS experiment.

Function of GAME7 and GAME8

Figure 11A:
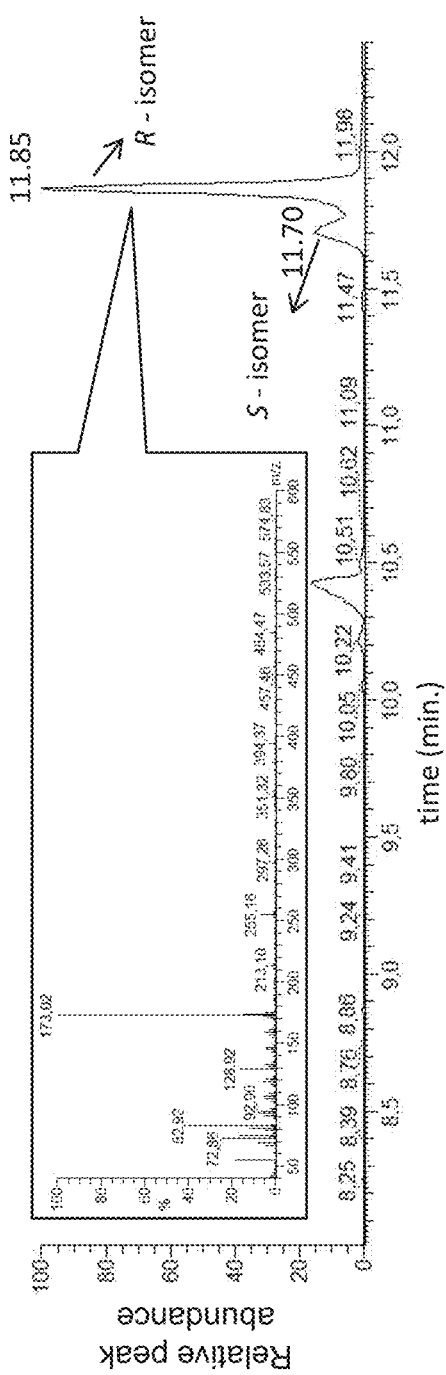
FIGS. 11A-11D show the effect silencing of GAME8 in tomato plants. GAME8-silenced leaves accumulated 22-(S) and -(R)-cholesterol (FIG. 11A). Chromatograms (mass range 172.5-173.5) acquired via EI-GC/MS, MS spectra and structures (tri-methyl-silyl derivatives) of the compounds are shown. Commercial standards of 22-(R)-(FIG. 11B) and 22-(S)-cholesterol (FIG. 11C) were used to verify the putative identification.
Figure 11B:
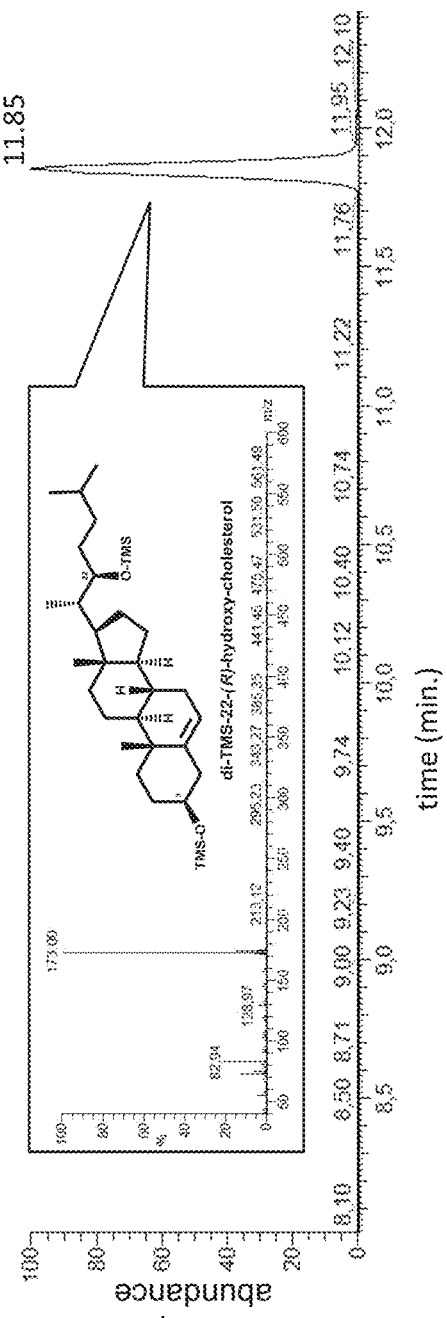
Figures 11C, 11D:
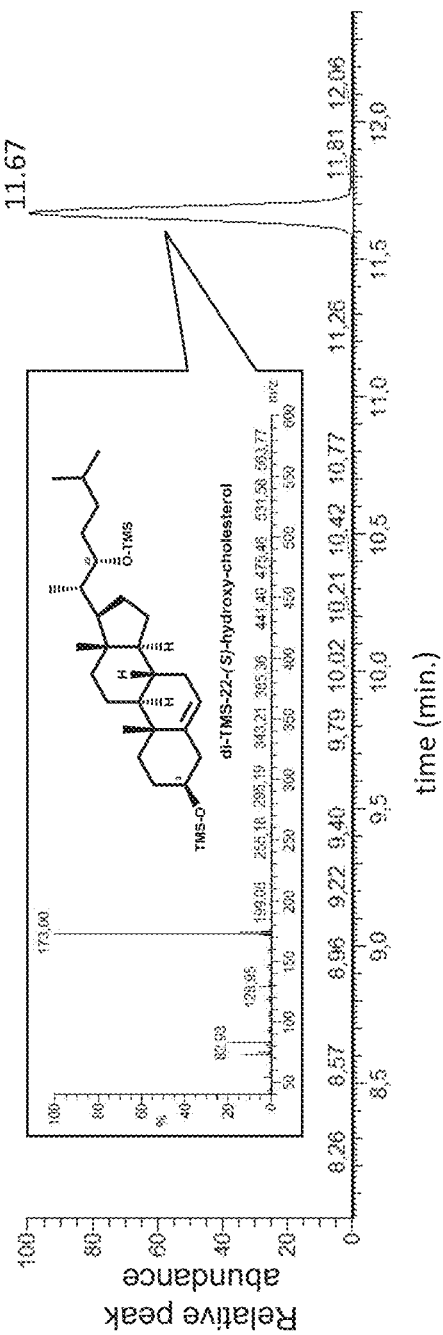

Genes that were tightly co-expressed and positioned elsewhere in the genome were also functionally examined. Two genes, designated GAME7 and GAME8 belong to the CYP72 subfamily of cytochrome P450s. GAME7 was co-expressed in both species (potato and tomato) while StGAME8a and StGAME8b were strongly co-expressed with StSGT1 and StGAME4 in potato. At present, we could not demonstrate SGA-related activity for GAME7 although as for GAME6 it was suggested to be involved in SGA metabolism (US 20120159676). Yet, GAME8-silenced tomato leaves accumulated 22-(R)-hydroxycholesterol (FIGS. 11A-11D), a proposed intermediate in the SGA biosynthetic pathway (FIG. 1). GAME8-silenced line accumulates both isomers in comparison to wild type (FIG. 11D). The (R)-isomer is more abundant and hence most likely to be the substrate of GAME8.

FIG. 12 shows the phylogenetic tree of GAME genes in the plant CYP450 protein family. The numbers on the branches indicate the fraction of bootstrap iterations supporting each node.

Example 4: Proposed Biosynthetic Pathway in Solanaceous Plants

Figure 13:
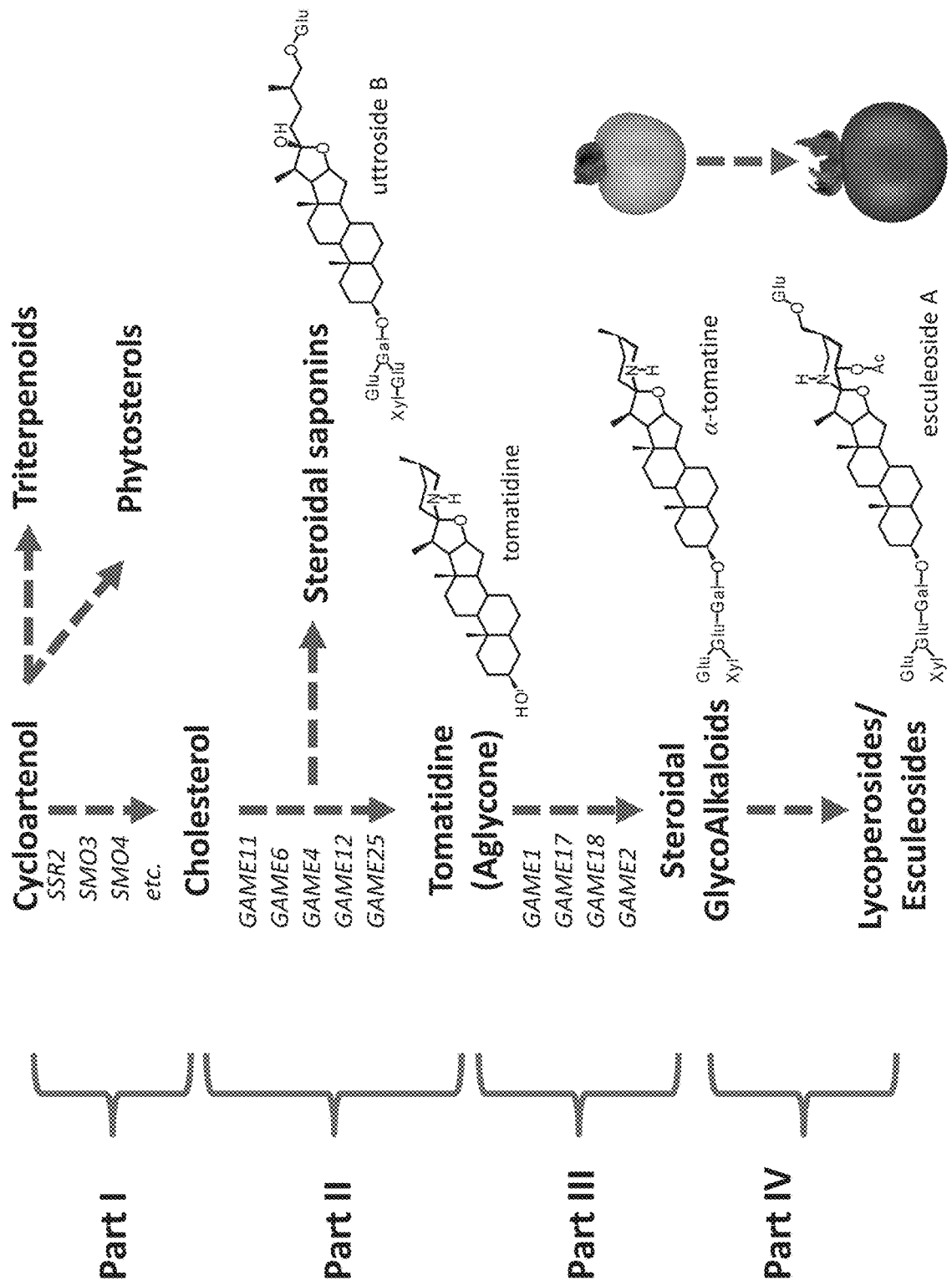
FIG. 13 shows a proposed expanded biosynthetic pathway in Solanaceous plants from Cycloartenol (Part I), through Cholesterol (Part II), through Tomatidine (Part III), through Steroidal Glycoalkaloids including α-tomatine to Lycoperosides/Esculeoside (Part IV). Dashed arrows represent multiple enzymatic reactions in the pathway.

An expanded biosynthetic pathway in Solanaceous plants has been proposed, as depicted in the schematic of FIG. 13 (dashed arrows represent multiple enzymatic reactions in the pathway) with respect to the tomato. This pathway can be broken down into four parts for convenience. In Part I, a series of reactions (catalyzed, e.g., by SSR2, SMO3, SMO4) converts cylcoartenol to cholesterol. Byproducts include triterpenoids and phytosterols. In Part II, a series of reactions (catalyzed, e.g., by GAME11, GAME6, GAME4, GAME12, GAME25) converts cholesterol to tomatidine (aglycone). Byproducts include steroidal saponins (e.g., uttroside B). In Part III, a series of reactions (catalyzed, e.g., by GAME1, GAME 17, GAME18, GAME2) converts tomatidine to steroidal glycoalkaloids (e.g., α-tomatine). In Part IV, a series of reactions converts steroidal glycoalkaloids (e.g., α-tomatine) of a green tomato to lycoperosides and/or esculeosides (e.g., esculeoside A) of a red tomato.

Figure 14A:
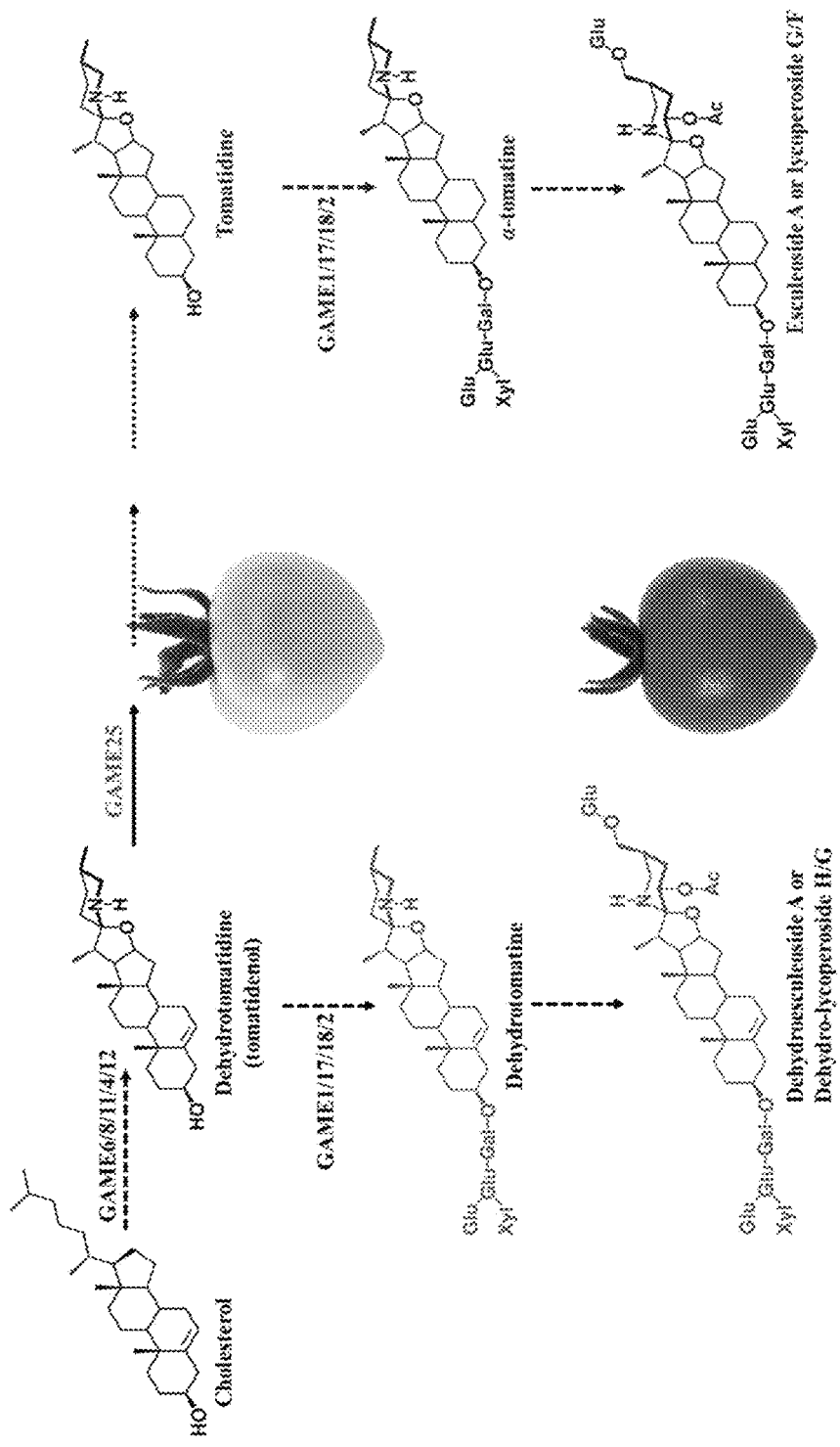
FIGS. 14A-14C show an overview of SGA biosynthesis in (FIG. 14A) tomato, (FIG. 14B) potato, and (FIG. 14C) eggplant.
Figure 14B:
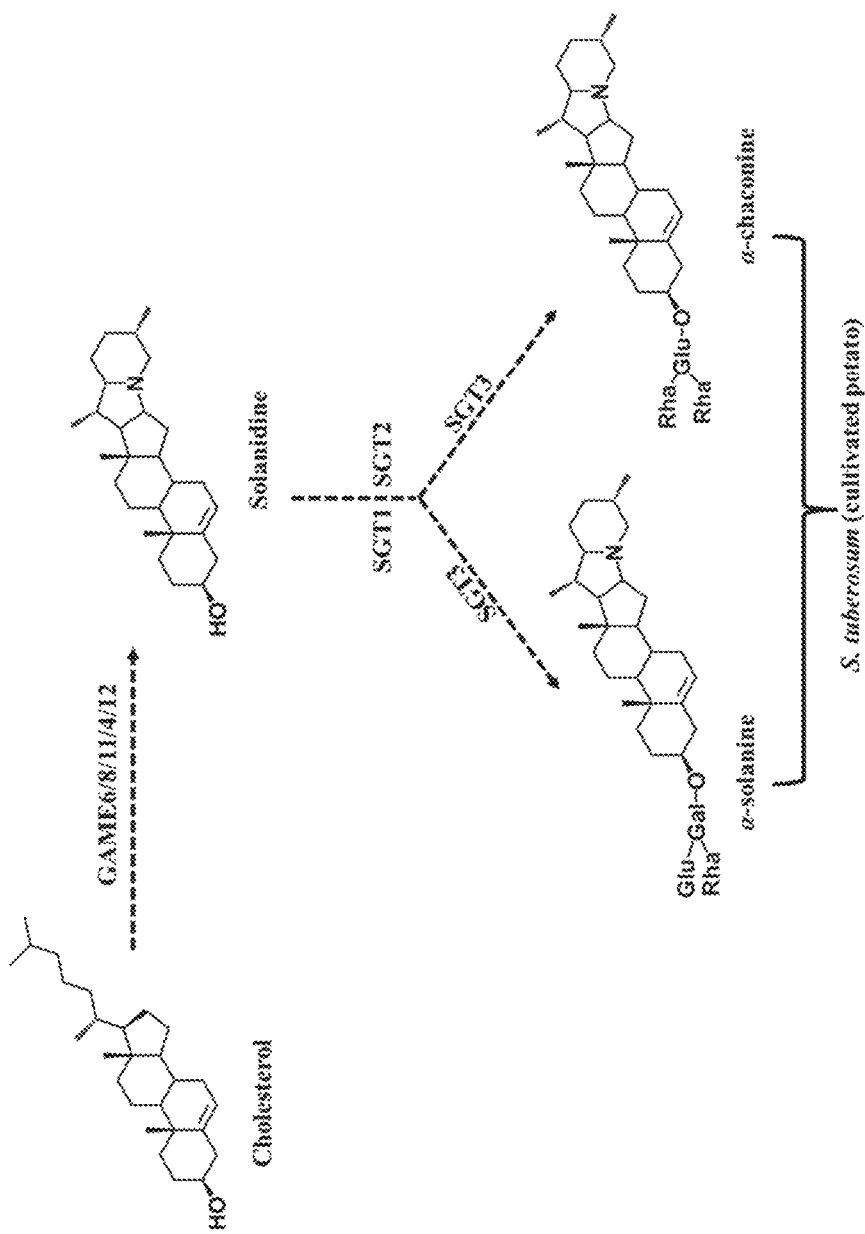
Figure 14C:
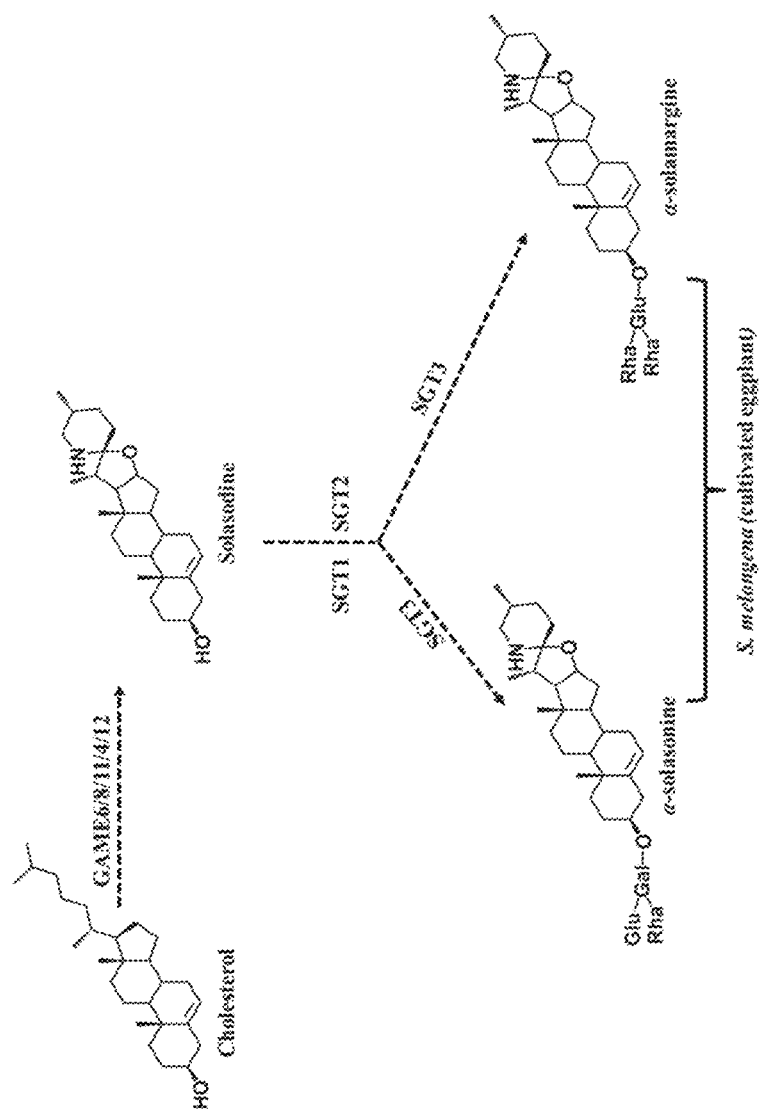

Example 5: Pathways Involving Steroidal Glycoalkaloid (SGA) Biosynthesis in Tomato, Potato, and Eggplant A cellulose synthase-like gene (GAME15) in tomato, potato, and eggplant has been identified as being associated with steroidal glycoalkaloid (SGA) biosynthesis (FIGS. 14A-14C). This gene has been shown to have been strongly co-expressed with other SGA biosynthesis genes (e.g., GAME4, GAME12) and also with regulators of SGA biosynthesis (e.g., GAME9).

Sequences were identified as follows:

```
>cellulose synthase like_tomato
                              [SEQ ID NO: 32]
ATGAAAAAAACCATGGAGCTCAACAAAAGCACTGT

TCCACAACCTATCACCACCGTATACCGACTCCACA

TGTTCATCCACTCAATAATCATGCTTGCATTAATA
```

-continued
```
TACTACCGTGTATCTAATTTGTTTAAATTCGAAAA

CATTCTCAGTTTACAAGCACTTGCTTGGGCGCTCA

TCACTTTTGGTGAATTTAGTTTCATTCTCAAGTGG

TTCTTCGGACAAGGTACTCGTTGGCGCCCCGTTGA

ACGAGATGTTTTCCCTGAAAACATTACTTGCAAAG

ATTCCGATCTACCGCCAATTGACGTAATGGTATTC

ACTGCCAATCCTAAGAAAGAGCCAATTGTAGATGT

CATGAACACTGTGATATCCGCAATGGCTCTTGATT

ATCCCACCGATAAATTGGCTGTGTATCTCGCTGAT

GATGGAGGATGTCCATTGTCGTTGTACGCCATGGA

ACAAGCGTGTTTGTTTGCAAAGCTATGGTTACCTT

TCTGTAGAAACTATGGAATTAAAACGAGATGCCCA

AAAGCATTTTTTCTCCGTTAGGAGATGATGACCG

TGTTCTTAAGAATGATGATTTTGCTGCTGAAATGA

AAGAAATTAAATTGAAATATGAAGAGTTCCAGCAG

AAGGTGGAACATGCTGGTGAATCTGGAAAAATCAA

TGGTAACGTAGTGCCTGATAGAGCTTCGCTTATTA

AGGTAATAAACGAGAGGGAGAACGAAAAGAGTGTG

GATGATATGACGAAAATGCCCTTGCTAGTTTATGT

ATCCCGTGAAAGAAGATTCAACCGTCTTCATCATT

TCAAGGGTGGATCTGCAAATGCTCTACTTCGAGTT

TCTGGAATAATGAGTAATGCCCCCTATGTACTGGT

GTTAGATTGTGATTTCTTCTGTCATGATCCAATAT

CAGCTAGGAAGGCAATGTGTTTTCATCTTGATCCA

AAGCTATCATCTGATTTAGCCTATGTTCAGTTCCC

TCAAGTCTTTTACAATGTCAGCAAGTCAGATATTT

ATGATGTCAAAATTAGACAGGCTTACAAGACAATA

TGGCATGGAATGGATGGTATCCAAGGCCCAGTGTT

ATCTGGGACTGGTTATTTTCTCAAGAGGAAAGCGT

TATACACAAGTCCAGGAGTAAAAGAGGCGTATCTT

AGTTCACCGGAAAAGCATTTTGGAAGGAGTAAAAG

GTTTCTTGCTTCATTAGAGGAGAAAAATGGTTATG

TTAAGGCAGATAAAGTCATATCAGAAGATATCATA

GAGGAAGCTAAGATGTTAGCTACTTGTGCATATGA

GGATGGCACACATTGGGGTCAAGAGATTGGTTATT

CATACGATTGTCATTTGGAGAGCACTTTTACTGGT

TATCTATTACACTGCAAAGGGTGGACATCTACTTA

TTTGTATCCAGACAGGCCATCTTTCTTGGGTTGTG

CCCCAGTTGATATGCAAGGTTTCTCATCACAGCTC

ATCAAATGGGTTGCTGCACTTACACAAGCTGGTTT

ATCACATCTCAATCCCATCACTTATGGTTTGAGTA
```

-continued

```
GTAGGATGAGGACTCTCCAATGCATGTGCTATGCC

TATTTGATGTATTTCACTCTTTATTCTTGGGGAAT

GGTTATGTATGCTAGTGTTCCTTCTATTGGCCTTT

TGTTTGACTTCCAAGTCTATCCTGAGGTACATGAT

CCGTGGTTTGCAGTGTATGTGATTGCTTTCATATC

GACAATTTTGGAGAATATGTCGGAGTCAATTCCAG

AAGGGGGATCAGTTAAAACGTGGTGGATGGAATAC

AGGGCATTGATGATGATGGGAGTTAGCGCAATATG

GTTAGGAGGATTGAAAGCTATATATGACAAGATAG

TCGGAACACAAGGAGAGAAATTGTATTTGTCGGAC

AAGGCAATTGACAAGGAAAAGCTCAAGAAATACGA

GAAGGGCAAATTTGATTTCCAAGGAATAGGGATAC

TTGCTCTGCCACTGATAGCATTTTCCGTGTTGAAC

CTCGTAGGCTTCATTGTTGGAGCTAATCATGTCTT

TATTACTATGAACTACGCAGGCGTGCTGGGCCAAC

TCCTCGTATCATCGTTCTTCGTCTTTGTTGTCGTC

ACTGTTGTCATTGATGTTGTATCTTTCTTAAAGGT

TTCTTAA
```

>cellulose synthase like_tomato [SEQ ID NO: 33]

```
MKKTMELNKSTVPQPITTVYRLHMFIHSIIMLALI
YYRVSNLFKFENILSLQALAWALITFGEFSFILKW
FFGQGTRWRPVERDVFPENITCKDSDLPPIDVMVF
TANPKKEPIVDVMNTVISAMALDYPTDKLAVYLAD
DGGCPLSLYAMEQACLFAKLWLPFCRNYGIKTRCP
KAFFSPLGDDDRVLKNDDFAAEMKEIKLKYEEFQQ
KVEHAGESGKINGNVVPDRASLIKVINERENEKSV
DDMTKMPLLVYVSRERRFNRLHHFKGGSANALLRV
SGIMSNAPYVLVLDCDFFCHDPISARKAMCFHLDP
KLSSDLAYVQFPQVFYNVSKSDIYDVKIRQAYKTI
WHGMDGIQGPVLSGTGYFLKRKALYTSPGVKEAYL
SSPEKHFGRSKRFLASLEEKNGYVKADKVISEDII
EEAKMLATCAYEDGTHWGQEIGYSYDCHLESTFTG
YLLHCKGWTSTYLYPDRPSFLGCAPVDMQGFSSQL
IKWVAALTQAGLSHLNPITYGLSSRMRTLQCMCYA
YLMYFTLYSWGMVMYASVPSIGLLFDFQVYPEVHD
PWFAVYVIAFISTILENMSESIPEGGSVKTWWMEY
RALMMMGVSAIWLGGLKAIYDKIVGTQGEKLYLSD
KAIDKEKLKKYEKGKFDFQGIGILALPLIAFSVLN
LVGFIVGANHVFITMNYAGVLGQLLVSSFFVFVVV
TVVIDVVSFLKVS
```

>cellulose synthase like_solanum pennellii [SEQ ID NO: 34]

```
ATGAAAAAAACCATGGAGCTCAACAAAAGCACTGT

TCCACAACCTATCACCACCGTATACCGACTCCACA

TGTTCATCCACTCAATAATCATGCTTGCATTAATA

TACTACCGTGTATCTAATTTGTTTAAATTCGAAAA

CATTCTCAGTTTACAAGCACTTGCTTGGCTACTCA

TCACTTTTGGTGAATTTAGTTTCATTCTCAAGTGG

TTCTTCGGACAAGGAACTCGTTGGCGCCCCGTTGA

ACGAGATGTTTTCCCTGAAAACATTACTTGCAAAG

ATTCCGATCTACCGCCAATTGACGTAATGGTGTTC

ACTGCCAATCCTAAGAAAGAGCCAATTGTAGATGT

CATGAACACTGTGATATCCGCAATGGCTCTTGATT

ATCCCACCGATAAATTGGCTGTGTATCTGGCCGAT

GATGGAGGATGTCCATTGTCCTTGTACGCCATGGA

ACAAGCATGTTTGTTTGCAAAGCTATGGTTACCTT

TCTGTAGAAAGTATGGAATTAAAACGAGATGCCCA

AAAGCATTTTTTCTCCGTTAGGAGATGATGACCG

TGTTCTTAAGAATGATGATTTTGCTGCTGAAATGA

AAGAAATTAAATTGAAATATGAAGAGTTCCAGCAG

AACGTGGAACATGCTGGTGAATCTGGAAAAATCAA

TGGCAACGTAGTGCCTGACAGAGCTTCGCTTATTA

AGGTAATAAACGAGAGGGAGAACGAAAAGAGTGTC

GATGATTTAACGAAAATGCCCTTGCTAGTTTATGT

ATCCCGTGAAAGAAGATTCAACCGTCTTCATCATT

TCAAGGGTGGATCTGCAAATGCTCTACTTCGAGTT

TCTGGAATAATGAGTAATGCCCCCTATGTACTGGT

GTTAGATTGTGATTTCTTCTGTCATGATCCGATAT

CAGCTAGGAAAGCAATGTGTTTTCATCTTGATCCA

AAGCTATCATCTGATTTAGCCTATGTTCAGTTCCC

TCAAGTCTTTTACAATGTCAGCAAGTCCGATATTT

ATGATGTCAAAATTAGACAGGCTTACAAGACAATA

TGGCATGGAATGGATGGTATCCAAGGCCCAGTGTT

ATCTGGAACTGGTTATTTTCTCAAGAGGAAGGCGT

TATACACAAGTCCAGGAGTAAAAGAGGCGTATCTT

AGTTCACCGGAAAAGCATTTTGGAAGGAGTAAAAA

GTTCCTTGCTTCATTAGAGGAGAAAAATGGTTATG

TTAAGGCAGATAAAGTCATATCAGAAGATATCATA

GAGGAAGCTAAGATCTTAGCTACTTGTGCATATGA

GGATGGCACACATTGGGGTCAAGAGATTGGTTATT

CATACGATTGTCATTTGGAGAGCACTTTTACTGGT

TATCTATTACACTGCAAAGGGTGGACATCTACTTA
```

-continued
TTTGTATCCAGACAGGCCATCTTTCTTGGGTTGTG
CCCCAGTTGATATGCAAGGTTTCTCATCACAGCTC
ATAAAATGGGTTGCTGCACTTACACAAGCTGGTCT
ATCACATCTCAATCCCATCACTTATGGTTTGAGTA
GTAGGATGAGAACTCTCCAATGCATGTGCTATGCC
TATTTGATGTATTTCACTCTTTATTCTTGGGGAAT
GGTTATGTATGCTAGTGTTCCTTCTATTGGCCTTT
TGTTTGGCTTCCAAGTCTACCCTGAGGTACATGAT
CCATGGTTTGCAGTGTATGTGATTGCTTTCATATC
GACAATTTTGGAGAATATGTCGGAGTCAATTCCAG
AAGGGGGATCAGTTAAAACGTGGTGGATGGAATAC
AGGGCATTGATGATGATGGGAGTTAGCGCAATATG
GTTAGGAGGATTGAAAGCTATATATGACAAGATAG
TCGGAACACAAGGAGAGAAATTGTATTTGTCGGAC
AAGGCAATTGACAAGGAAAAGCTCAAGAAATACGA
GAAGGGCAAATTTGATTTCCAAGGAATAGGGATAC
TTGCTCTGCCATTGATAGCATTTTCCGTGTTGAAC
CTCGTAGGCTTCATTGTTGGAGCTAATCATGTCTT
TATTACTATGAACTACGCAGGCGTGCTGGGCCAAC
TCCTCGTATCATCATTCTTCGTCTTTGTTGTCGTC
ACTGTTGTCATTGATGTTGTATCTTTCTTAAAGGT
TCCTTAA >cellulose synthase like_solanum pennellii
[SEQ ID NO: 35]
MKKTMELNKSTVPQPITTVYRLHMFIHSIIMLALI
YYRVSNLFKFENILSLQALAWLLITFGEFSFILKW
FFGQGTRWRPVERDVFPENITCKDSDLPPIDVMVF
TANPKKEPIVDVMNTVISAMALDYPTDKLAVYLAD
DGGCPLSLYAMEQACLFAKLWLPFCRKYGIKTRCP
KAFFSPLGDDDRVLKNDDFAAEMKEIKLKYEEFQQ
NVEHAGESGKINGNVVPDRASLIKVINERENEKSV
DDLTKMPLLVYVSRERRFNRLHHFKGGSANALLRV
SGIMSNAPYVLVLDCDFFCHDPISARKAMCFHLDP
KLSSDLAYVQFPQVFYNVSKSDIYDVKIRQAYKTI
WHGMDGIQGPVLSGTGYFLKRKALYTSPGVKEAYL
SSPEKHFGRSKKFLASLEEKNGYVKADKVISEDII
EEAKILATCAYEDGTHWGQEIGYSYDCHLESTFTG
YLLHCKGWTSTYLYPDRPSFLGCAPVDMQGFSSQL
IKWVAALTQAGLSHLNPITYGLSSRMRTLQCMCYA
YLMYFTLYSWGMVMYASVPSIGLLFGFQVYPEVHD
PWFAVYVIAFISTILENMSESIPEGGSVKTWWMEY
RALMMMGVSAIWLGGLKAIYDKIVGTQGEKLYLSD -continued
KAIDKEKLKKYEKGKFDFQGIGILALPLIAFSVLN
LVGFIVGANHVFITMNYAGVLGQLLVSSFFVFVVV
TVVIDVVSFLKVS >cellulose synthase like_potato
[SEQ ID NO: 36]
ATGAAAAAACCATGGAGCTCAACAAAAGCACTGT
TCCACAACCTATCACCACCATATACCGACTCCACA
TGTTTATCCACTCTATAATCATGGTTGCATTAATA
TACTACCGTGTATCTAATTTGTTTAAATTCGAAAA
CATTCTGAGTTTACAAGCACTTGCTTGGGTACTCA
TCACTTTTGGTGAATTTAGTTTCATTCTCAAGTGG
TTCTTCGGACAAGGAACTCGTTATCGCCCTGTTGA
AAGAGATGTTTTCCCTGAAAACATAACTTGCAAAG
ATTCCGATCTACCACCAATTGACGTAATGGTATTC
ACTGCCAATCCTAAGAAAGAGCCAATTGTGGATGT
CATGAACACTGTGATATCCGCAATGGCTCTTGATT
ATCCTACGGATAAATTGGCTGTGTATCTGGCTGAT
GATGGAGGATGTCCTTTGTCATTGTACGCCATGGA
AGAAGCATGTGTGTTTGCAAAGCTGTGGCTACCTT
TCTGTAGGAAGTATGGAATTAAAACTAGATGCCCT
AAAGCGTTTTTTCTCCTTTAGGAGATGATGAACG
TGTTCTTAAGAATGATGATTTTGATGCTGAAATGA
AGAAATTAAATTGAAATATGAAGAGTTCCAGCAG
AATGTGGAACGTGCTGGTGAATCTGGAAAAATCAA
TGGTAACGTAGTGCCTGATAGAGCCTCGTTTATTA
AGGTAATAAACGACAGAAAAGCGGAGAGCGAAAAG
AGTGCCGATGATTTAACGAAAATGCCCTTGCTAGT
TTATGTATCCCGTGAAAGAAGATTCAACCGTCTTC
ATCACTTCAAGGGTGGATCTGCAAATGCTCTTCTT
CGAGTTTCTGGAATAATGAGTAATGCCCCCTATAT
ACTGGTGTTAGATTGTGATTTCTTCTGTCATGATC
CAATATCAGCTAGGAAGGCAATGTGTTTTCATCTT
GATCCAAAGCTATCATCTGATTTAGCTTATGTTCA
GTTCCCTCAAGTCTTTTACAATGTCAGCAAGTCCG
ATATTTATGATGTCAAAATTAGACAGGCTTACAAG
ACAATATGGCATGGAATGGATGGTATCCAAGGCCC
AGTGTTATCAGGAACTGGTTATTTTCTGAAGAGGA
AGGCGTTATACACGAGTCCAGGAGTAAAGGAGGAG
TATCTTAGTTCACCGGAAAAGCATTTTGGAAGGAG
TAAAAAGTTCCTTGCTTCACTAGAGGAGAAAAATG
GTTATGTTAAGGCAGAGAAAGTCATATCAGAAGAT
ATCGTAGAGGAAGCTAAGACCTTAGCTACTTGTGC ATATGAGGATGGCACACATTGGGGTCAAGAGATTG
GTTATTCATACGATTGTCATTTGGAGAGCACTTTT
ACTGGTTATCTATTACACTGCAAAGGGTGGAGATC
GACTTATTTGTATCCAGACAGGCCATCTTCTTGG
GTTGTGCCCCAGTTGATATGCAAGGTTTCTCCTCA
CAGCTCATAAAATGGGTTGCTGCACTTACACAAGC
TGGTTTATCACATCTCAATCCCATCACTTATGGCT
TTAGTAGCAGGATGAAAACTCTCCAATGCATGTGC
TATGCCTATTTGATATATTTCACTCTTTATTCTTG
GGGAATGGTTCTATATGCTAGTGTTCCTTCTATTG
GCCTTTTGTTTGGCTTCCAAGTCTATCCCGATGTA
CATGGATCCATGGTTTGCAGTGTATGTGATTGCTTT
CATATCGGCAATTTTGGAGAATATGTCGGAGTCAA
TTCCTGATGGGGATCATTTAAATCTTGGTGGATG
GAATACAGGGCACTGATGATGATGGGAGTTAGTGC
AATATGGTTAGGAGGATTGAAAGCTATATTAGACA
GGATAATCGGAACAGAAGGAGAGAAATTGTATTTA
TCGGACAAGGCAATTGACAAGGAAAAGCTCAAGAA
ATACGAGAAGGGGAAATTTGATTTCCAAGGAATAG
GGATACTTGCTGTACCATTGATAGCATTTTCCTTG
TTGAACCTCGTAGGCTTCATTGTTGGAGCTAATCA
TGTCTTTATTACTATGAACTACGCAGGTGTGCTTG
GCCAACTCCTCGTATCATCCTTCTTCGTCTTTGTC
GTGGTCACTGTTGTCATTGATGTCGTTTCTTTCTT
AAAGGTTTCTTAA
>cellulose synthase like_potato
[SEQ ID NO: 37]
MELNKSTVPQPITTIYRLHMFIHSIIMVALIYYRV
SNLFKFENILSLQALAWVLITFGEFSFILKWFFGQ
GTRYRPVERDVFPENITCKDSDLPPIDVMVFTANP
KKEPIVDVMNTVISAMALDYPTDKLAVYLADDGGC
PLSLYAMEEACVFAKLWLPFCRKYGIKTRCPKAFF
SPLGDDERVLKNDDFDAEMKEIKLKYEEFQQNVER
AGESGKINGNVVPDRASFIKVINDRKAESEKSADD
LTKMPLLVYVSRERRFNRLHHFKGGSANALLRVSG
IMSNAPYILVLDCDFFCHDPISARKAMCFHLDPKL
SSDLAYVQFPQVFYNVSKSDIYDVKIRQAYKTIWH
GMDGIQGPVLSGTGYFLKRKALYTSPGVKEEYLSS
PEKHFGRSKKFLASLEEKNGYVKAEKVISEDIVEE
AKTLATCAYEDGTHWGQEIGYSYDCHLESTFTGYL
LHCKGWRSTYLYPDRPSFLGCAPVDMQGFSSQLIK
WVAALTQAGLSHLNPITYGFSSRMKTLQCMCYAYL IYFTLYSWGMVLYASVPSIGLLFGFQVYPDVHDPW
FAVYVIAFISAILENMSESIPDGGSFKSWWMEYRA
LMMMGVSAIWLGGLKAILDRIIGTEGEKLYLSDKA
IDKEKLKKYEKGKFDFQGIGILAVPLIAFSLLNLV
GFIVGANHVFITMNYAGVLGQLLVSSFFVFVVVTV
VIDVVSFLKVS >cellulose synthase like_solanum chacoense
[SEQ ID NO: 38]
ATGAAAAAAACCATGGAGCTCAACAAAAGCACTGT
TCCACAACCTATCACCACCATATACCGACTCCACA
TGTTCGTCCATTCTATAATCATGGCTGCATTAATA
TACTACCGTGTATCTAATTTGTTTAAATTCGAAAA
CATTCTGAGTTTACAAGCACTTGCTTGGGTACTCA
TCACTTTTGGTGAATTTAGTTTCATTCTCAAGTGG
TTCTTCGGACAAGGAACTCGTTGGCGCCCTGTTGA
AAGAGATGTTTTCCCTGAAAACATAACTTGCAAAG
ATTCCGATCTACCACCAATTGACGTAATGGTATTC
ACTGCCAATCCTAAGAAAGAGCCAATTGTGGATGT
CATGAACACTGTGATATCCGCAATGGCTCTAGATT
ATCCTACGGATAAATTGGCTGTGTATCTGGCTGAT
GATGGAGGATGTCCTTTGTCATTGTACGCCATGGA
AGAAGCATGTGTGTTTGCAAAGCTGTGGCTACCTT
TCTGTAGGAAGTATGGAATTAAAACCAGATGCCCT
AAAGCGTTTTTTTCTCCTTTAGGAGATGATGACCG
TGTTCTTAAGAATGATGATTTTGATGCTGAAATGA
AAGAAATTAAATTGAAATATGAAGAGTTCCAGCAG
AATGTGGAACGTGCTGGTGAATCTGGAAAAATCAA
TGGTAACGTAGTGCCTGATAGAGCCTCGTTTATTA
AGGTAATAAACGACAGAAAAACGGAGAGCGAAAAG
AGTGCCGATGATTTAACGAAAATGCCCTTGCTAGT
TTATGTATCCCGTGAAAGAAGATTCAACCGTCTTC
ATCACTTCAAGGGTGGATCTGCAAATGCTCTTCTT
CGAGTTTCTGGAATAATGAGTAATGCCCCCTATAT
ACTGGTGTTAGATTGTGATTTCTTCTGTCATGATC
CAATATCAGCTAGGAAGGCAATGTGTTTTCATCTT
GATCCAAAGCTATCATCTGATTTAGCTTATGTTCA
GTTCCCTCAAGTCTTTTACAATGTCAGCAAGTCCG
ATATTTATGATGTCAAAATTAGACAGGCTTACAAG
ACAATATGGCATGGAATGGATGGTATCCAAGGCCC
AGTGTTATCAGGAACTGGTTATTTTCTGAAGAGGA
AGGCGTTATACACGAGTCCAGGAGTAAAGGAGGAG
TATCTTAGTTCACCGGAAAAGCATTTTGGAAGGAG -continued
```
TAAAAAGTTCCTTGCTTCACTAGAGGAGAAAAATG
GTTATGTTAAGGCAGAGAAAGTCATATCAGAAGAT
ATCGTAGAGGAAGCTAAGACCTTAGCTACTTGTGC
ATATGAGGATGGTACACATTGGGGTCAAGAGATCG
GTTATTCATACGATTGTCATTTGGAGAGCACTTTT
ACTGGTTATCTATTACACTGCAAAGGGTGGACATC
GACTTATTTGTATCCAGACAGGCCATCTTTCTTGG
GTTGTGCTCCAGTTGATATGCAAGGTTTCTCCTCA
CAGCTCATAAAATGGGTTGCTGCACTTACACAAGC
TGGTTTATCACATCTCAATCCCATCACTTATGGCT
TGAGTAGCAGGATGAAAACTCTCCAATGCATGTGC
TATGCCTATTTGATATATTTCACTCTTTATTCTTG
GGGAATGGTTCTATATGCTAGTATTCCTTCTATTG
GTCTTTTGTTTGGCTTCCAAGTCTATCCGGAGGTA
CATGATCCATGGTTTGCAGTGTATGTGATTGCTTT
CATATCGACAATTTTGGAGAATATGTCGGAGTCAA
TTCCAGAAGGGGATCATTTAAATCGTGGTGGATG
GAATACAGGGCACTGATGATGATGGGAGTTAGTGC
AATATGGTTAGGAGGATTGAAAGCTATATTAGACA
AGATAATCGGAACAGAAGGAGAGAAATTGTATTTG
TCAGACAAGGCAATTGACAAGGAAAAGCTCAAGAA
ATACGAGAAGGGGAAATTTGATTTCCAAGGAATAG
GGATACTTGCTGTACCATTGATAGCATTTTCCCTG
TTGAACCTGGTAGGCTTCATTGTTGGAGCTAATCA
TGTCTTTATTACTATGAACTACGCAGGTGTGCTTG
GCCAACTCCTCGTATCATCCTTCTTCGTCTTTGTC
GTGGTCACTGTTGTCATTGATGTCGTTTCTTTCTT
AAAGGTTTCTTAA
```
>cellulose synthase like_solanum chacoense
[SEQ ID NO: 39]
```
MKKTMELNKSTVPQPITTIYRLHMFVHSIIMAALI
YYRVSNLFKFENILSLQALAWVLITFGEFSFILKW
FFGQGTRWRPVERDVFPENITCKDSDLPPIDVMVF
TANPKKEPIVDVMNTVISAMALDYPTDKLAVYLAD
DGGCPLSLYAMEEACVFAKLWLPFCRKYGIKTRCP
KAFFSPLGDDDRVLKNDDFDAEMKEIKLKYEEFQQ
NVERAGESGKINGNVVPDRASFIKVINDRKTESEK
SADDLTKMPLLVYVSRERRFNRLHHFKGGSANALL
RVSGIMSNAPYILVLDCDFFCHDPISARKAMCFHL
DPKLSSDLAYVQFPQVFYNVSKSDIYDVKIRQAYK
TIWHGMDGIQGPVLSGTGYFLKRKALYTSPGVKEE
YLSSPEKHFGRSKKFLASLEEKNGYVKAEKVISED
```

-continued
```
IVEEAKTLATCAYEDGTHWGQEIGYSYDCHLESTF
TGYLLHCKGWTSTYLYPDRPSFLGCAPVDMQGFSS
QLIKWVAALTQAGLSHLNPITYGLSSRMKTLQCMC
YAYLIYFTLYSWGMVLYASIPSIGLLFGFQVYPEV
HDPWFAVYVIAFISTILENMSESIPEGGSFKSWWM
EYRALMMMGVSAIWLGGLKAILDKIIGTEGEKLYL
SDKAIDKEKLKKYEKGKFDFQGIGILAVPLIAFSL
LNLVGFIVGANHVFITMNYAGVLGQLLVSSFFVFV
VVTVVIDVVSFLKVS
```
>cellulose synthase like_eggplant
[SEQ ID NO: 40]
```
ATGAAAAAACAAATGGAGCTCAACAGAAGTGTTGT
ACCGCAACCTATCACCACCATTTACCGTCTCCACA
TGTTTATCCATGCCCTAATCATGCTAGCACTAATA
TACTACCGTGTCTCTAATTTGGCCAAATTCGAAAA
CATCCTCAGTTTACAAGCACTTGCTTGGGCTCTTA
TCACGTTAGGTGAACTTTGTTTCATAGTCAAGTGG
TTCTTCGGACAAGGGACTCGTTGGCGTCCTGTTGA
TAGGGATGTCTTCCCTGAAAACATCACTTGTCCAG
ATTCCGAGCTACCCCCATTGATGTCATGGTTTTC
ACTGCAAATCCTAAGAAAGAGCCAATTGTGGATGT
CATGAACACTGTCATATCCGCAATGGCTCTTGATT
ACCCGACCGACAAATTGGCCGTTTATTTGTCTGAT
GATGGAGGATGCCCCTTGACGTTGTACGCAATGGA
GGAAGCTTGTTCCTTTGCCAAGTTGTGGCTACCTT
TTTGTAGGAAGTATGGAATCAAAACAAGGTGCCCT
AAGGCGTTTTTTTCTCCATTAGGAGAAGATGACCG
TGTATTGAAGAGTGATGACTTTGTTTCTGAAATGA
AAGAAATGAAGTCAAAATATGAAGAGTTCCAGCAG
AACGTGGACCGTGCTGGTGAATCCGGAAAAATCAA
AGGTGACGTAGTGCCTGATAGACCCGCGTTTCTTA
AGGTACTAAATGACAGGAAGACGGAGAACGAGAAG
AGTGCAGACGATTTAACTAAAATGCCTTTGCTAGT
ATACGTATCCCGTGAAAGAAGAACTCACCGTCGCC
ATCACTTCAAGGGTGGATCTGCAAATGCTCTTCTT
CGAGTTTCTGGGATAATCAGTAATGCCCCCTATAT
ACTGGTTTTAGATTGTGATTTCTTCTGTCATGATC
CAATATCAGCTCGGAAGGCAATGTGTTTCCATCTT
GATCCAAAACTATCACCTGACTTAGCTTACGTGCA
GTTCCCTCAAGTGTTTTACAATGTTAGCAAGTCCG
ATATTTACGACGTCAAAATTAGACAGGCTTACAAG
ACAATATGGCACGGGATGGATGGTATCCAAGGCCC
```

-continued
AGTGTTATCGGGAACTGGTTATTTTTAAAAAGA
AGGCGTTGTACACGAGTCCAGGTCTAAAGATGAG
TATCTTAGTTCACCGGAAAAGCATTTCGGAACGAG
TAGAAAGTTCATTGCTTCACTAGAGGAGAATAATT
ATGTTAAGCAAGAGAAAGTCATATCAGAAGATATC
ATAGAGGAAGCTAAGAGACTGGCTACTTGTGCATA
CGAGGATGGCACACATTGGGGTCAAGAGGCAAACA
GGCCATCTTCTTGGGTTGTGCCCCAGTTGATATG
CAAGGTTTCTCCTCACAGCTCATAAAATGGGTTGC
TGCACTCACACAAGCAGGTCTATCACATCTCAATC
CCATCACTTACGGCTTCAAGAGCAGAATGAGAACT
CTCCAAGTCTTGTGTTATGCCTATTTGATGTATTT
CTCTCTTTATTCTTGGGGAATGGTTCTACATGCTA
GTGTTCCTTCTATTGGCCTTCTCTCTGGCATTAAA
ATCTACCCGGAGGTGTATGATCCATGGTTTGTTGT
GTATGTGATTGCTTTCATATCAACAATTTTGGAGA
ATATGTCGGAATCAATTCCGGAAGGGGATCGGTT
AAAACGTGGTGGATGGAATACAGGGCACTGATGAT
GATGGGAGTTAGTGCAATATGGCTAGGAGGAGTGA
AAGCCATAGTAGACAAGATCATCGGAACGCAAGGA
GAGAAATTGTATTTGTCGGACAAAGCAATTGACAA
GGAAAAGCTCAAGAAATACGAGAAGGGGAAATTTG
ATTTCCAAGGAATAGGAATACTTGCTGTACCATTG
ATAACATTTTCTGTGTTGAACCTGGTAGGCTTCTT
GGTTGGAATTAATCAAGTGTTGATAACGATGAAGT
TCGCAGGCGTGCTGGGCCAACTCCTCGTATCATCC
TTCTTCGTCTTTGTCGTCGTTACTGTTGTCATTGA
TGTCGTATCTTTCTTAAAGGATTCTTAA
>cellulose synthase like_eggplant
[SEQ ID NO: 41]
MKKQMELNRSVVPQPITTIYRLHMFIHALIMLALI
YYRVSNLAKFENILSLQALAWALITLGELCFIVKW
FFGQGTRWRPVDRDVFPENITCPDSELPPIDVMVF
TANPKKEPIVDVMNTVISAMALDYPTDKLAVYLSD
DGGCPLTLYAMEEACSFAKLWLPFCRKYGIKTRCP
KAFFSPLGEDDRVLKSDDFVSEMKEMKSKYEEFQQ
NVDRAGESGKIKGDVVPDRPAFLKVLNDRKTENEK
SADDLTKMPLLVYVSRERRTHRRHHFKGGSANALL
RVSGIISNAPYILVLDCDFFCHDPISARKAMCFHL
DPKLSPDLAYVQFPQVFYNVSKSDIYDVKIRQAYK
TIWHGMDGIQGPVLSGTGYFLKKKALYTSPGLKDE
YLSSPEKHFGTSRKFIASLEENNYVKQEKVISEDI -continued
IEEAKRLATCAYEDGTHWGQEANRPSFLGCAPVDM
QGFSSQLIKWVAALTQAGLSHLNPITYGFKSRMRT
LQVLCYAYLMYFSLYSWGMVLHASVPSIGLLSGIK
IYPEVYDPWFVVYVIAFISTILENMSESIPEGGSV
KTWWMEYRALMMMGVSAIWLGGVKAIVDKIIGTQG
EKLYLSDKAIDKEKLKKYEKGKFDFQGIGILAVPL
ITFSVLNLVGFLVGINQVLITMKFAGVLGQLLVSS
FFVFVVVTVVIDVVSFLKDS
>cellulose synthase like_capsicum annuum
[SEQ ID NO: 42]
ATGGAGCTCAACAGATGTACGGTGCAGCAACCTAC
CACTGCCATATACCGACTACACATGTTTCTCCACT
CTCTAATCATGCTTGCATTAGTATACTATCGTTTG
TCTAATCTGTTTTACTTCGAAAACGTCCTCACTTT
ACAAGCATTTGCATGGGGGCTTATCACCTTAGGTG
AAATTTGTTTCATTGTCAAGTGGTTCTTTGGTCAA
GGGACTCGTTGGCGCCCCGTTGTCAGGGAAGTGTT
CCTGGACAATATTACTTGCCAAGATTCCGAGCTGC
CCGCACTAGATGTGATGGTTTTCACTGCCAATCCC
AAGAAAGAGCCAATTGTGGATGTCATGAACACTGT
GATATCCGCAATGGCTCTTGATTACCCGACGGATA
AATTGGCTGTGTATCGGCTGATGATGGAGGATGC
CCCTTGACGTTGTACGCCATGGAGGAGGCCTGTTC
TTTTGCCAAGTTGTGGCTACCTTTCTGTAGGAAGT
ATGGAATCAAAACAAGGTGCCCCAAAGCGTTTTTT
TCTCCATTAGGAGAAGATGATCGTATCCTTAAGAA
CGATGACTTTGTAGCTGAAATGAAAGAAATTAAAT
TAAAATATGAGGAGTTCCAGCAGAATGTAAACCTT
GCTGGTGAATCCGGAAAAATCAAAGGTGACGTAGT
GCCTGATAGAGCCTCGTTTATTAAGGTAATAAATG
ACAGGAAAATGGAGAACAAGAAGAGTGCCGACGAT
ATAACGAAAATGCCTTTGCTAGTATACGTATCCCG
TGAAAGAAGATTTAACAGTCGTCATCACTTCAAGG
GTGGATCTGCAAATGCTCTTCTTCGAGTTTCAGGG
ATAATGAGTAATGCCCCCTATTTACTGGTCTTAGA
TTGTGATTTCTTCTGTCATGATCCAACATCAGCTC
GGAAGGCAATGTGTTTCCATCTTGATCCAAAACTA
TCACCTTCCTTAGCTTATGTGCAGTTCCCTCAAGT
GTTTTACAATGTCAGCAAGTCCGATATATACGATG
TCAAAATTAGACAGGCTTACAAGACAATATGGCAC
GGAATGGATGGTATCCAAGGCCCAGTGTTATCGGG
AACTGGGTATTTTCTGAAGAGGAAAGCGTTATACA

```
CGAGTCCAGGTCTAAAGGATGAGTATCTTATTTCA
CCGGAAAAGCATTTCGGATCAAGTAGAAAGTTCAT
TGCTTCTCTAGAGGAGAACAATGGTTATGTTAAGC
AAGAGAAACTCATAACAGAAGATATTATAGAGGAA
GCGAAGACCTTGTCTACTTGTGCATACGAGGATGG
TACACGATGGGCGAAGAGATCGGTTATACCTACA
ATTGCCATTTGGAGAGCACTTTTACCGGCTATCTT
TTGCACTGCAAAGGGTGGACATCAACATATTTGTA
TCCAGAAAGGCCATCTTTCTTGGGTTGTGCCCCAG
TTGATATGCAAGGATTCTCCTCACAACTCACAAAA
TGGGTTGCTGCACTCACACAAGCTGGTCTATCACA
TCTCAATCCCATCACTTACGGCATGAAGAGCAGGA
TTAAGACTATCCAATGCTTGTGCTATGCCTATTTG
ATGTATTTCTCTCTCTATTCTTGGGGAATGGTTCT
GCATGCTAGTGTTCCTTCTATTAGCCTTTTGCTTG
GCATTCAAGTCTACCCCGAGGTCTATGATCCATGG
TTTGCAGTGTATGTGCTTGCTTTCATATCGACAAT
TTTGGAGAACATGTCAGAGTCAATTCCAGAAGGCG
GTTCAGTTAAAACTTGGTGGATGGAATACAGGGCA
CTGATGATGATGGGAGTTAGTGCAATATGGTTAGG
AGGAGTGAAAGCTATAGTAGAAAAGATCATCGGAA
CTCAAGGAGAGAAATTATATTTGTCGGACAAAGCA
ATTGACAAGGAAAAGCTCAAGAAATATGAGAAGGG
GAAATTTGATTTCCAAGGGATAGGGATACTTGCTG
TTCCATTGATAACATTCTCAGCGTTGAATTTGGTA
GGCTTCATGGTTGGAGCTAATCAAGTGATTCTTAC
TATGAAGTTCGAAGCTTTGCTAGGCCAACTCCTTG
TGTCATCCTTCTTCGTCTTTGTGGTGGTCACCGTT
GTCATAGATGTCCTATCTTTCTTAAAAGACTCTTA
A
>cellulose synthase like_capsicum annuum
                                 [SEQ ID NO: 43]
MELNRCTVQQPTTAIYRLHMFLHSLIMLALVYYRL
SNLFYFENVLTLQAFAWGLITLGEICFIVKWFFGQ
GTRWRPVVREVFLDNITCQDSELPALDVMVFTANP
KKEPIVDVMNTVISAMALDYPTDKLAVYLADDGGC
PLTLYAMEEACSFAKLWLPFCRKYGIKTRCPKAFF
SPLGEDDRILKNDDFVAEMKEIKLKYEEFQQNVNL
AGESGKIKGDVVPDRASFIKVINDRKMENKKSADD
ITKMPLLVYVSRERRFNSRHHFKGGSANALLRVSG
IMSNAPYLLVLDCDFFCHDPTSARKAMCFHLDPKL
SPSLAYVQFPQVFYNVSKSDIYDVKIRQAYKTIWH
GMDGIQGPVLSGTGYFLKRKALYTSPGLKDEYLIS
PEKHFGSSRKFIASLEENNGYVKQEKLITEDIIEE
AKTLSTCAYEDGTRWGEEIGYTYNCHLESTFTGYL
LHCKGWTSTYLYPERPSFLGCAPVDMQGFSSQLTK
WVAALTQAGLSHLNPITYGMKSRIKTIQCLCYAYL
MYFSLYSWGMVLHASVPSISLLLGIQVYPEVYDPW
FAVYVLAFISTILENMSESIPEGGSVKTWWMEYRA
LMMMGVSAIWLGGVKAIVEKIIGTQGEKLYLSDKA
IDKEKLKKYEKGKFDFQGIGILAVPLITFSALNLV
GFMVGANQVILTMKFEALLGQLLVSSFFVFVVVTV
VIDVLSFLKDS
```

The following sequences were generated for silencing GAME15 in their respective plants:

```
Region used for GAME15 silencing in Tomato
                                 [SEQ ID NO: 44]
GGCTCTTGATTATCCCACCGATAAATTGGCTGTGT
ATCTCGCTGATGATGGAGGATGTCCATTGTCGTTG
TACGCCATGGAACAAGCGTGTTTGTTTGCAAAGCT
ATGGTTACCTTTCTGTAGAAACTATGGAATTAAAA
CGAGATGCCCAAAAGCATTTTTTTCTCCGTTAGGA
GATGATGACCGTGTTCTTAAGAATGATGATTTTGC
TGCTGAAATGAAAGAAATTAAATTGAAATATGAAG
AGTTCCAGCAGAAGGTGGAACATGC Region used for GAME15 silencing in Potato
                                 [SEQ ID NO: 45]
GGCTCTTGATTATCCTACGGATAAATTGGCTGTGT
ATCTGGCTGATGATGGAGGATGTCCTTTGTCATTG
TACGCCATGGAAGAAGCATGTGTGTTTGCAAAGCT
GTGGCTACCTTTCTGTAGGAAGTATGGAATTAAAA
CTAGATGCCCTAAAGCGTTTTTTTCTCCTTTAGGA
GATGATGAACGTGTTCTTAAGAATGATGATTTTGA
TGCTGAAATGAAAGAAATTAAATTGAAATATGAAG
AGTTCCAGCAGAATGTGGAACGTGCTGGTG Region used for GAME15 silencing in Eggplant
                                 [SEQ ID NO: 46]
GGCTCTTGATTACCCGACCGACAAATTGGCCGTTT
ATTTGTCTGATGATGGAGGATGCCCCTTGACGTTG
TACGCAATGGAGGAAGCTTGTTCCTTTGCCAAGTT
GTGGCTACCTTTTTGTAGGAAGTATGGAATCAAAA
CAAGGTGCCCTAAGGCGTTTTTTCTCCATTAGGA
GAAGATGACCGTGTATTGAAGAGTGATGACTTTGT
TTCTGAAATGAAAGAAATGAAGTCAAAATATGAAG
AGTTCCAGCAGAACGTGGACCGTGCTGGTGAATCC
```

```
-continued
GGAAAAATCAAAGGTGACGTAGTGCCTGATAGACC

CGCGTTTCTTAAGGTACTAAATGACAGGAAGACGG

AGAACGAGAAGAGTGCAGACGATTTAACTAAAATG

CCTTTGCTAGTATACGTATCCCGTGAAAGAAGAAC

TCACCGTCGCCATCACTTCAAGGGTGG
```

RNAi lines for the GAME15 gene in tomato and potato were generated. GAME15-RNAi transgenic tomato plants showed severe reduction in α-tomatine and downstream SGAs in leaves; α-tomatine was not detected in GAME15-silenced green fruit. Furthermore, no esculeosides or other SGAs were detected during tomato fruit developmental stages (e.g., breaker and red fruit). In addition, a 15-20 fold increase in cholesterol, which is a precursor for SGAs was observed in leaves and green fruit of GAME15-RNAi tomato plants. In potato, silencing of GAME15 resulted in a major reduction in α-chaconine and α-solanine, while the cholesterol pool in these lines increased.

Example 6: Generation of GAME15-RNAi Transgenic Tomato Potato and Eggplant Plants The GAME15-RNAi construct was generated by introducing a selected fragment (silencing sequences SEQ ID NO: 44 (tomato), SEQ ID NO: 45 (potato), and SEQ ID NO: 46 (eggplant)) to pENTR/D-TOPO (Invitrogen) (by NodI and AscI) and further subcloning of this fragment to the pK7GWIWG2 (II) binary vector using the Gateway LR Clonase II enzyme mix (Invitrogen). The vector was transformed into tomato, potato and eggplant as described previously (Itkin et al. 2011. The Plant Cell 23:4507-25; Sonawane et al. 2018. PNAS 115(23): E5418-E5428). Positive GAME25-downregulated lines were further used for LC-MS analysis.

Example 7: Game15-Silenced Tomato Plants Showed Severely Reduced SGA Profile In order to determine the precise role of GAME15 in SGA metabolism, GAME15-RNAi (GAME15i) transgenic tomato lines (#21, #22 and #23) were generated using the tomato silencing sequence above (SEQ ID NO: 44).

Figure 15A:
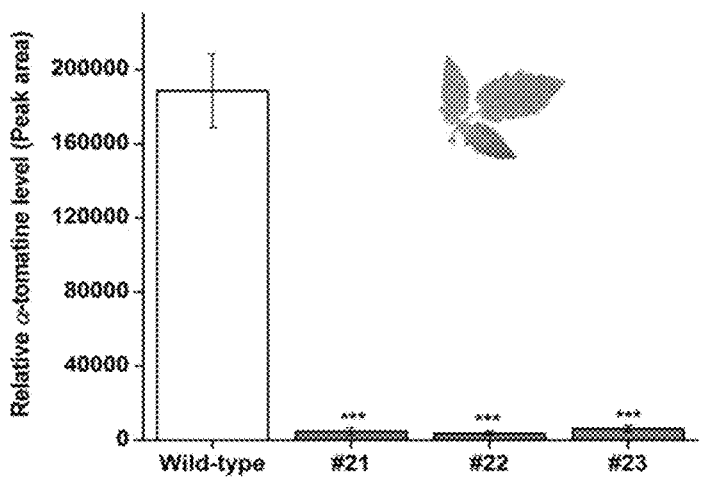
FIGS. 15A-15C show major SGA levels in (FIG. 15A) leaves and (FIG. 15B) green fruit and (FIG. 15C) red fruit of wild type (non-transformed) and GAME15-RNAi tomato lines determined by LC-MS. #21, #22 and #23 are three independent GAME15-RNAi transgenic tomato lines. Values indicate means of three biological replicates ±standard error. Asterisks indicate significant changes from wild-type samples as calculated by a Student's t-test (*P-value <0.05; P-value <0.01; *P-value <0.001).

GAME15-RNAi leaves showed severe reduction in α-tomatine, compared with wild-type tomato leaves (FIG. 15A). Furthermore, the SGAs profile of GAME15i fruit was subsequently compared to wild-type ones at different stages of development and ripening. During the transition from green to red fruit in tomato, α-tomatine is converted to esculeosides and lycoperosides, while dehydrotomatine is converted to dehydroesculeosides and dehydrolycoperosides (FIG. 14A).

Figure 15B:
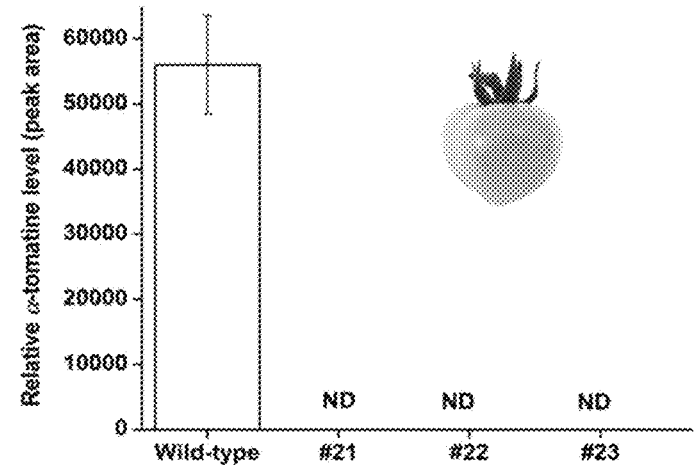
Figure 15C:
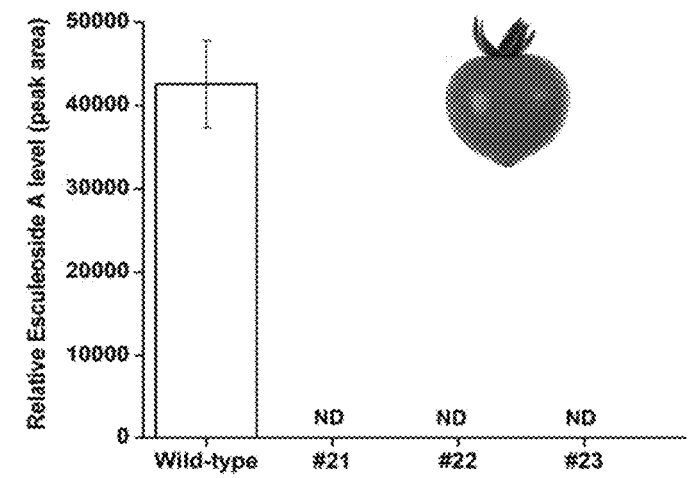

GAME15i green and red fruits did not show any trace of SGAs (e.g., α-tomatine or Esculeoside A) suggesting complete loss of SGAs in tomato fruits due to GAME15i silencing (FIGS. 15B and 15C).

Example 8: Altering GAME15 Expression has Major Impact on SGAs in Potato

Similar to tomato, GAME15i was also silenced in potato (#1, #2, and #3) to determine its effect on potato SGAs metabolism, using the potato silencing sequence above (SEQ ID NO: 45).

Figure 16:
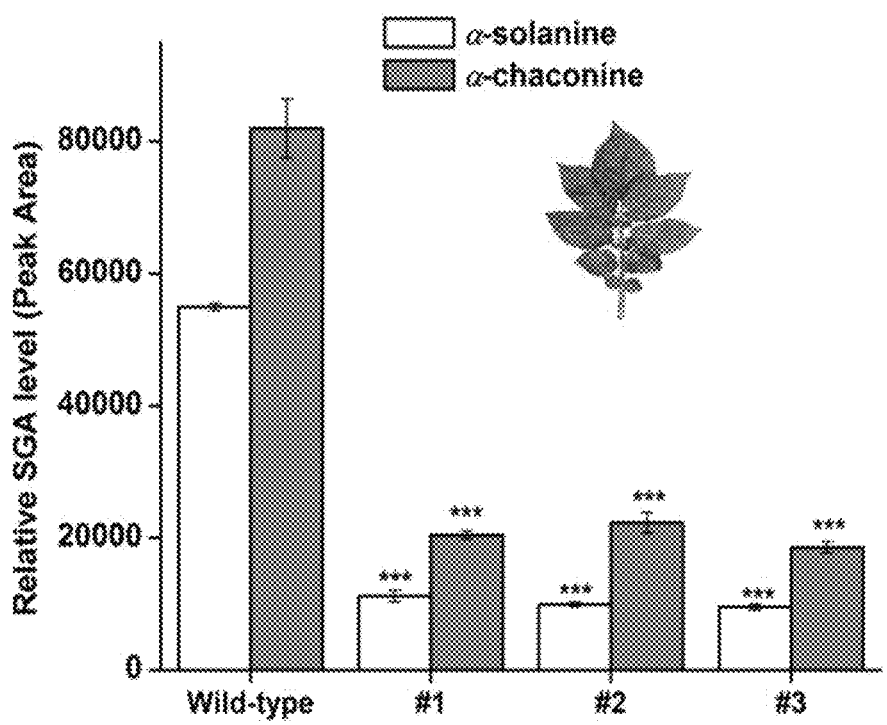
FIG. 16 shows levels of α-solanine and α-chaconine in leaves of GAME15-RNAi lines as determined by LC-MS. #1, #2 and #3 are three independent GAME15i transgenic potato lines. Values represent mean±standard error (n=3). Student's t-test was used to assess whether the transgenic lines significantly differ from wild-type plants: (*P-value <0.05; P-value <0.01; *P-value <0.001).

Silencing of GAME15 in potato resulted in drastic reduction in α-chaconine (shaded bars) and α-solanine (open bars), major SGAs in potato leaf tissue (FIG. 16), in comparison with potato leaf tissue of the wild-type.

Example 9: High Cholesterol Accumulation in GAME15-Silenced Tomato Leaves

Figure 17:
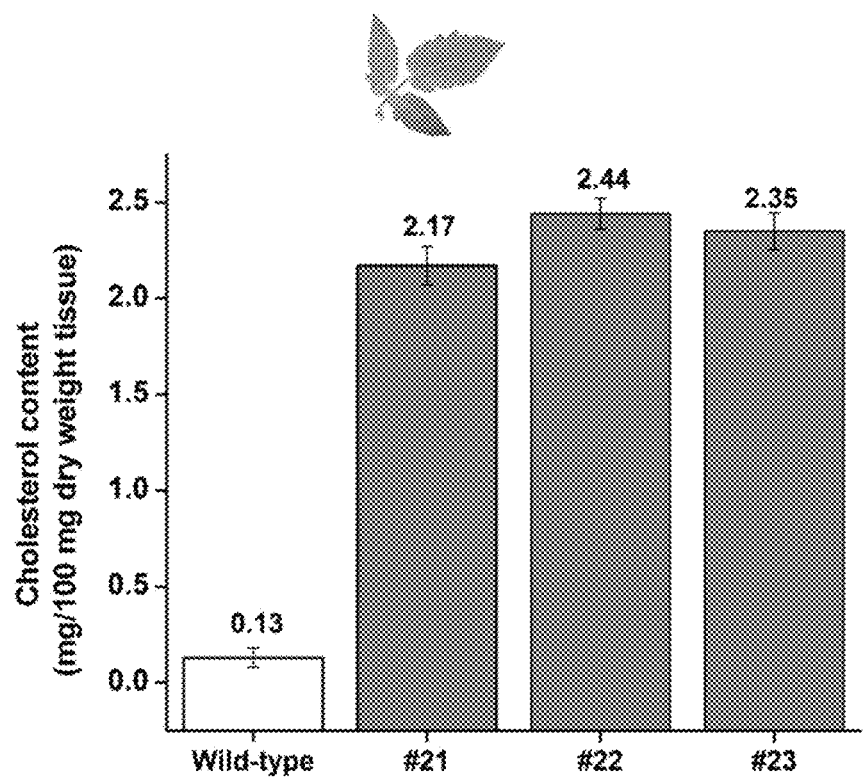
FIG. 17 shows the cholesterol content of tomato leaves derived from GAME15 silenced plants. Values represent mean of three biological replicates ±standard error. Asterisks indicate significant changes in leaves of the three independent transgenes (#21, #22 and #23) as compared to wild-type leaves (i.e. non-transformed) calculated by a Student's t-test (*P-value <0.05; P-value <0.01; *P-value <0.001). Epicholesterol was used as an internal standard in sample preparations and relative cholesterol level is expressed as ratios of cholesterol peak areas in sample compared to internal standard. The analysis was performed using GC-MS.

Cholesterol serves as a key precursor in the biosynthesis of SGAs (Sonawane et al., 2016, Nat. Plants 3: 16205). As severe reduction and subsequent complete loss of SGAs was observed in GAME/5i-silenced tomato plants, the cholesterol levels in these plants were examined. An ~15-20-fold increase in cholesterol (SGA precursor) was observed in leaves of GAME/5i-silenced tomato plants compared to the leaves of wild-type tomato plants (FIG. 17).

Example 10: Altering GAME15 Expression and Observing its Impact on SGAs in Eggplant Similar to potato, GAME15i is also silenced in eggplant to determine its effect on potato SGAs metabolism, using the eggplant silencing sequence above (SEQ ID NO: 46).

The effect of silencing of GAME15 in eggplant is observed with respect to reduced levels of α-solasonine and/or α-solamargine in comparison with wild-type eggplant (FIG. 14C).

Example 11: Overexpression of GAME15 in Tomato, Potato, and Eggplant

Alternatively, tomato, potato, and/or eggplant plants are genetically modified or gene edited to overexpress GAME15.

To increase production of α-tomatine and esculeosides and/or lycoperosides in tomato plants (FIG. 14A), tomato plants are genetically modified or gene edited to overexpress GAME15.

To increase production of α-solanine and/or α-chaconine in potato plants (FIG. 14B), potato plants are genetically modified or gene edited to overexpress GAME15.

To increase production of α-solasonine and/or α-solamargine in eggplant (FIG. 14C), eggplant plants are genetically modified, or gene edited to overexpress GAME15.

Example 12: Plants and Crops with Modified Levels and Compositions of SGAs

Based on the foregoing, Solanaceous plants (e.g., tomato, potato, eggplant, and/or pepper plants) and/or crops are prepared, such as through classical breeding or genetic engineering (e.g., genetically modified or transgenic plants, gene edited plants, and the like), with modified levels and compositions of SGAs, conferring on the plant a chemical barrier against a broad range of insects and other pathogens and/or removing anti-nutritional compounds (e.g., chaconine and/or solanine from potato).

Furthermore, high cholesterol or high phytosterol tomato lines are used to engineer high value steroidal compounds (e.g., pro-vitamin D and/or diosgenin), such as through synthetic biology tools.

In addition, high phytosterol (e.g., phytocholesterol) lines are used to produce components used in cosmetic products.

In other instances, Solanaceous plants (e.g., tomato, potato, eggplant, and/or pepper plants) and/or crops are prepared with increased levels of SGAs and/or decreased levels of phytosterols.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A genetically modified plant comprising at least one cell having altered expression of a gene encoding a GAME15 cellulose synthase like protein compared to its expression in a corresponding unmodified plant, wherein the genetically modified plant has an altered content of at least one steroidal alkaloid or a glycosylated derivative thereof, or of at least one steroidal saponin or a glycosylated derivative thereof, compared to the corresponding unmodified plant, wherein (a) the amino acid sequence of the cellulose synthase like protein of the corresponding unmodified plant comprises amino acid sequence set forth in any one of SEQ ID NOS: 33, 35, 37, 39, 42, or 43; or (b) the polynucleotide encoding the cellulose synthase like protein of the corresponding unmodified plant comprises the nucleic acid sequence set forth in any one of SEQ ID NOS: 32, 34, 36, 38, 40, or 42.

2. The genetically modified plant of claim 1, wherein the expression of the GAME15 protein is altered, the altering comprising mutagenizing the gene, wherein the mutagenesis comprises introduction of one or more point mutations, or genome editing, or use of a bacterial CRISPR/CAS system, or a combination thereof.

3. The genetically modified plant of claim 1, wherein expression of the gene encoding the cellulose synthase like protein is reduced compared to its expression in the corresponding unmodified plant, thereby the genetically modified plant comprises reduced content at least one steroidal alkaloid or a glycosylated derivative thereof, or of at least one steroidal saponin or a glycosylated derivative thereof, compared to the corresponding unmodified plant.

4. The genetically modified plant of claim 3, wherein the genetically modified plant is a transgenic plant comprising cell comprising at least one silencing molecule targeted to a polynucleotide encoding the cellulose synthase like protein, or wherein the transgenic plant comprises a polynucleotide encoding the cellulose synthase like protein, wherein expression of the polynucleotide is selectively silenced, repressed, or reduced.

5. The genetically modified plant of claim 4, wherein the transgenic plant comprises a polynucleotide encoding the cellulose synthase like protein, wherein the polynucleotide has been selectively edited by deletion, insertion, or modification to silence, repress, or reduce expression thereof, or wherein the genetically modified plant is a progeny of the gene edited plant.

6. The genetically modified plant of claim 4, wherein the transgenic plant comprises at least one cell comprising at least one silencing molecule targeted to the GAME15 gene.

7. The genetically modified plant of claim 4, wherein:
(a) the silencing molecule comprises a polynucleotide having a nucleic acid sequence complementary to a region of the GAME15 gene having the nucleic acid sequence set forth in any one SEQ ID NOS: 32, 34, 36, 38, 40, or 42 or a complementary sequence thereof; or
(b) the silencing molecule is selected from the group consisting of an RNA interference molecule and an antisense molecule, or wherein the silencing molecule is a component of a viral induced gene silencing system.

8. The genetically modified plant of claim 7, wherein:
a. the silencing molecule is targeted to a GAME'S fragment having the nucleic acid sequence set forth in SEQ ID NO: 44 or a complementary sequence thereof;
b. the silencing molecule is targeted to a GAME'S fragment having the nucleic acid sequence set forth in SEQ ID NO: 45 or a complementary sequence thereof; or
c. the silencing molecule is targeted to a GAME'S fragment having the nucleic acid sequence set forth in SEQ ID NO: 46 or a complementary sequence thereof.

9. The genetically modified plant of claim 4, wherein the genetically modified plant is a Solanaceae plant having a reduced content of at least one steroidal glycoalkaloid selected from the group consisting of α-tomatine, α-omatidine, α-chaconine, α-solanine, α-solasonine, α-solmargine, and derivatives thereof, compared to a corresponding unmodified plant.

10. The genetically modified plant of claim 4, wherein the genetically modified plant further comprises an elevated content of a phytosterol or a derivative thereof, a cholesterol or a derivative thereof, a phytocholesterol or a derivative thereof, a cholestenol or a derivative thereof, a phytocholestanol or a derivative thereof, or a steroidal saponin or a derivative thereof compared to a corresponding unmodified plant.

11. The genetically modified plant of claim 9, wherein the plant is a Solanaceae plant selected from the group consisting of tomato, potato, eggplant, and pepper.

12. The genetically modified plant of claim 11, wherein the plant is a Solanaceae plant:
(a) the plant is a tomato plant comprising a reduced content of α-tomatine, α-omatidine, or derivatives thereof or an elevated content of a phytosterol, a phytocholesterol or cholesterol, a phytocholestenol or cholestenol, a steroidal saponin, or derivative thereof;
(b) the plant is a potato plant comprising a reduced content of α-chaconine, α-solanine, or derivatives thereof; or
(c) the plant is an eggplant plant comprising a reduced content of α-solasonine, α-solamargine, or derivatives thereof.

13. The genetically modified plant of claim 1, wherein expression of the gene encoding the cellulose synthase like protein is elevated compared to its expression in the corresponding unmodified plant, thereby the genetically modified plant comprises elevated content at least one steroidal alkaloid or a glycosylated derivative thereof, or of at least one steroidal saponin or a glycosylated derivative thereof, compared to the corresponding unmodified plant.

14. The genetically modified plant of claim 13, wherein the transgenic plant comprises a polynucleotide encoding the cellulose synthase like protein, wherein expression of the polynucleotide is selectively increased.

15. The genetically modified plant of claim 14, wherein the transgenic plant comprising at least one cell comprising at least one transcribable polynucleotide encoding at least one protein selected from the group consisting of at least one a cellulose synthase like protein, wherein:
(a) the cellulose synthase like protein is a GAME15 protein; or
(b) the transcribable polynucleotide comprises the nucleic acid sequence set forth in any one of SEQ ID NOS: 32, 34, 36, 38, 40, or 42.

16. The genetically modified plant of claim 13, wherein the genetically modified plant is a Solanaceae plant having an elevated content of at least one steroidal glycoalkaloid selected from the group consisting of α-tomatine, α-omatidine, α-chaconine, α-solanine, α-solasonine, α-solmargine, and derivatives thereof, compared to a corresponding unmodified plant.

17. The genetically modified plant of claim 13, wherein the genetically modified plant further comprises a reduced content of a phytosterol or a derivative thereof, a cholesterol or a derivative thereof, a phytocholesterol or a derivative thereof, a cholestenol or a derivative thereof, a phytocholestanol or a derivative thereof, or a steroidal saponin or a derivative thereof compared to a corresponding unmodified plant.

18. The genetically modified plant of claim 16, wherein the plant is a Solanaceae plant selected from the group consisting of tomato, potato, eggplant, and pepper.

19. A method of reducing the content of at least one steroidal alkaloid or a glycosylated derivative thereof, or of at least one steroidal saponin or a glycosylated derivative thereof, in a modified plant, the method comprising (a) transforming at least one plant cell with at least one silencing molecule targeted to a nucleic acid sequence encoding a GAME15 cellulose synthase like protein; or
(b) mutagenizing at least one gene or a combination of genes, the genes encoding the GAME15 cellulose synthase like proteins, wherein the mutagenesis comprises introduction of one or more point mutations into the gene, or genome editing, or use of a bacterial CRISPR/CAS system, or a combination thereof, wherein expression of the gene encoding the cellulose synthase like protein is reduced in the modified plant compared to its expression in a corresponding unmodified plant, thereby the modified plant comprises reduced content at least one steroidal alkaloid or a glycosylated derivative thereof, or of at least one steroidal saponin or a glycosylated derivative thereof, compared to the corresponding unmodified plant.

20. The method of claim 19, wherein:
(a) the amino acid sequence of the cellulose synthase like protein of the corresponding unmodified plant comprises the amino acid sequence set forth in any one of SEQ ID NOS: 33, 35, 37, 39, 42, or 43; or
(b) the polynucleotide encoding the cellulose synthase like protein of the corresponding unmodified plant comprises the nucleic acid sequence set forth in any one of SEQ ID NOS: 32, 34, 36, 38, 40, or 42.

21. The method of claim 19, wherein:
(a) the silencing molecule is targeted to a GAMED fragment having the nucleic acid sequence set forth in SEQ ID NO: 44 or a complementary sequence thereof;
(b) the silencing molecule is targeted to a GAMED fragment having the nucleic acid sequence set forth in SEQ ID NO: 45 or a complementary sequence thereof; or
(c) the silencing molecule is targeted to a GAMED fragment having the nucleic acid sequence set forth in SEQ ID NO: 46 or a complementary sequence thereof.

22. The method of claim 19, wherein the modified plant is a Solanaceae plant having a reduced content of at least one steroidal glycoalkaloid selected from the group consisting of α-tomatine, α-omatidine, α-chaconine, α-solanine, α-solasonine, α-solmargine, and derivatives thereof, compared to the corresponding unmodified plant.

23. The method of claim 19, wherein the modified plant further comprises an elevated content of a phytosterol or a derivative thereof, a cholesterol or a derivative thereof, a phytocholesterol or a derivative thereof, a cholestenol or a derivative thereof, a phytocholestanol or a derivative thereof, or a steroidal saponin or a derivative thereof compared to a corresponding unmodified plant.

24. The method of claim 22, wherein the modified plant is a Solanaceae plant selected from the group consisting of tomato, potato, eggplant, and pepper.

25. The method of claim 22, wherein:
(a) the plant is a tomato plant comprising a reduced content of α-tomatine, α-omatidine, or derivatives thereof or an elevated content of a phytosterol, a phytocholesterol or cholesterol, a phytocholestenol or cholestenol, a steroidal saponin, or derivative thereof;
(b) the plant is a potato plant comprising a reduced content of α-chaconine, α-solanine, or derivatives thereof; or
(c) the plant is an eggplant plant comprising a reduced content of α-solasonine, α-solamargine, or derivatives thereof.

26. A method of producing at least one phytosterol in a modified plant, the method comprising
(a) transforming at least one plant cell with at least one silencing molecule targeted to a nucleic acid sequence encoding a GAME15 cellulose synthase like factor; or
(b) mutagenizing at least one gene or a combination of genes, the genes encoding the GAME15 cellulose synthase like factors, wherein the mutagenesis comprises introduction of one or more point mutations into the gene, or genome editing, or use of a bacterial CRISPR/CAS system, or a combination thereof, wherein expression of the gene encoding the cellulose synthase like protein is reduced in the modified plant compared to its expression in a corresponding unmodified plant, thereby the modified plant comprises reduced content at least one steroidal alkaloid or a glycosylated derivative thereof, or of at least one steroidal saponin or a glycosylated derivative thereof, compared to the corresponding unmodified plant; and wherein the modified plant further comprises an elevated content of a phytosterol or a derivative thereof, a cholesterol or a derivative thereof, a phytocholesterol or a derivative thereof, a cholestenol or a derivative thereof, a phytocholestanol or a derivative thereof, or a steroidal saponin or a derivative thereof compared to a corresponding unmodified plant.

27. The method of claim 26, wherein:
(a) the amino acid sequence of the cellulose synthase like protein of the corresponding unmodified plant comprises the sequence set forth in any one of SEQ ID NOS: 33, 35, 37, 39, 42, or 43; or
(b) wherein the polynucleotide encoding the cellulose synthase like protein of the corresponding unmodified plant comprises the nucleic acid sequence set forth in any one of SEQ ID NOS: 32, 34, 36, 38, 40, or 42.

28. The method of claim 26, further comprising purifying the phytosterol extracted from the transformed plant.

29. The method of claim 26, wherein the phytosterol comprises phytocholesterol.

30. The method of claim 26, wherein:
(a) the silencing molecule is targeted to a GAMED fragment having the nucleic acid sequence set forth in SEQ ID NO: 44 or a complementary sequence thereof;
(b) the silencing molecule is targeted to a GAMED fragment having the nucleic acid sequence set forth in SEQ ID NO: 45 or a complementary sequence thereof; or
(c) the silencing molecule is targeted to a GAMED fragment having the nucleic acid sequence set forth in SEQ ID NO: 46 or a complementary sequence thereof.

31. The method of claim 26, wherein the modified plant is a Solanaceae plant.

32. The method of claim 31, wherein the Solanaceae plant is selected from the group consisting of tomato, potato, eggplant, and pepper.

* * * * *